United States Patent
Hong et al.

(10) Patent No.: US 12,289,994 B2
(45) Date of Patent: Apr. 29, 2025

(54) PHOTOELECTRIC CONVERSION DEVICE AND SENSOR AND ELECTRONIC DEVICE

(71) Applicant: Samsung Electronics Co., Ltd., Suwon-si (KR)

(72) Inventors: Hye Rim Hong, Suwon-si (KR); Taejin Choi, Suwon-si (KR); Chul Joon Heo, Busan (KR); Kyung Bae Park, Hwaseong-si (KR); Seon-Jeong Lim, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 1106 days.

(21) Appl. No.: 16/999,130

(22) Filed: Aug. 21, 2020

(65) Prior Publication Data

US 2021/0135125 A1     May 6, 2021

(30) Foreign Application Priority Data

Nov. 6, 2019 (KR) .................. 10-2019-0141158

(51) Int. Cl.
    *H01L 51/00*     (2006.01)
    *C07D 209/86*     (2006.01)
    *H10K 85/60*     (2023.01)
    *H10K 30/30*     (2023.01)
    *H10K 30/82*     (2023.01)
    *H10K 39/32*     (2023.01)

(52) U.S. Cl.
    CPC ....... *H10K 85/6572* (2023.02); *C07D 209/86* (2013.01); *H10K 30/30* (2023.02); *H10K 30/82* (2023.02); *H10K 39/32* (2023.02)

(58) Field of Classification Search
None
See application file for complete search history.

(56) References Cited

U.S. PATENT DOCUMENTS

| | | | |
|---|---|---|---|
| 6,660,410 B2 | 12/2003 | Hosokawa | |
| 6,979,414 B2 | 12/2005 | Hosokawa | |
| 7,226,546 B2 | 6/2007 | Hosokawa | |
| 8,378,339 B2 | 2/2013 | Nomura et al. | |
| 8,513,657 B2 | 8/2013 | Suzuki et al. | |
| 8,637,860 B2 | 1/2014 | Nomura et al. | |
| 8,753,757 B2 | 6/2014 | Hosokawa | |
| 8,847,141 B2 | 9/2014 | Fukuzaki et al. | |
| 8,847,208 B2 | 9/2014 | Mitsui et al. | |
| 9,085,537 B2 | 7/2015 | Nomura et al. | |
| 9,419,230 B2 | 8/2016 | Kim et al. | |
| 9,537,107 B2 | 1/2017 | Nagao et al. | |
| 9,564,607 B2 | 2/2017 | Hosokawa | |
| 10,312,457 B2 | 6/2019 | Obana et al. | |
| 10,672,994 B2 | 6/2020 | Obana et al. | |
| 10,886,335 B2 | 1/2021 | Ujiie et al. | |
| 11,018,308 B2 | 5/2021 | Obana et al. | |
| 11,716,896 B2 | 8/2023 | Obana et al. | |
| 2010/0308311 A1 | 12/2010 | Mitsui et al. | |
| 2012/0205636 A1 | 8/2012 | Kim et al. | |
| 2014/0339518 A1 | 11/2014 | Yamamoto et al. | |
| 2015/0243894 A1 | 8/2015 | Zeng et al. | |
| 2016/0351830 A1 | 12/2016 | Hanaki et al. | |
| 2017/0077431 A1 | 3/2017 | Mizuno et al. | |
| 2018/0212155 A1 | 7/2018 | Hung et al. | |
| 2019/0148650 A1 | 5/2019 | Kwak et al. | |
| 2019/0165284 A1 | 5/2019 | Chen | |
| 2019/0288040 A1 | 9/2019 | Ujiie | |
| 2021/0134887 A1 | 5/2021 | Ujiie et al. | |
| 2023/0354627 A1 | 11/2023 | Ujiie et al. | |

FOREIGN PATENT DOCUMENTS

| | | |
|---|---|---|
| JP | 201182507 A | 4/2011 |
| JP | 2011176259 A | 9/2011 |
| JP | 4916078 B2 | 4/2012 |
| JP | 2015233117 A | 12/2015 |
| JP | 2018085427 A | 5/2018 |
| KR | 20110079402 A | 7/2011 |
| KR | 20120013173 A | 2/2012 |
| KR | 20120122812 A | 11/2012 |
| KR | 20140017556 A | 2/2014 |
| KR | 20150010387 A | 1/2015 |
| KR | 20150043669 A | 4/2015 |
| KR | 20150099395 A | 8/2015 |

(Continued)

OTHER PUBLICATIONS

Hokuto Seo et al., 'Color Sensors with Three Vertically Stacked Organic Photodetectors' *Japanese Journal of Applied Physics*, vol. 46, No. 49, Dec. 2007, pp. L1240-L1242.

Satoshi Aihara et al., 'Stacked Image Sensor With Green- and Red-Sensitive Organic Photoconductive Films Applying Zinc Oxide Thin-Film Transistors to a Signal Readout Circuit' *IEEE Transactions on Electron Devices*, vol. 56, No. 11, Nov. 2009, pp. 2570-2576.

(Continued)

*Primary Examiner* — Po-Chih Chen

(74) *Attorney, Agent, or Firm* — HARNESS, DICKEY & PIERCE, P.L.C.

(57) ABSTRACT

Disclosed are a photoelectric conversion device includes a first electrode and a second electrode, a photoelectric conversion layer between the first electrode and the second electrode, the photoelectric conversion layer including a p-type semiconductor and an n-type semiconductor, and an organic buffer layer between the first electrode and the photoelectric conversion layer, the organic buffer layer including an organic buffer material, wherein a difference between a LUMO energy level of the organic buffer material and a LUMO energy level of the n-type semiconductor is greater than or equal to about 1.2 eV and the organic buffer material includes at least three carbazole moieties, and a sensor, and an electronic device including the same.

31 Claims, 14 Drawing Sheets

(56) References Cited

FOREIGN PATENT DOCUMENTS

| KR | 20160080090 A | 7/2016 |
|---|---|---|
| KR | 20170070359 A | 6/2017 |
| KR | 20170134163 A | 12/2017 |
| KR | 20180012193 A | 2/2018 |
| KR | 20190070064 A | 6/2019 |
| WO | 2015-056965 A1 | 4/2015 |
| WO | 2017-204594 A1 | 11/2017 |
| WO | WO-2019-066242 A1 | 4/2019 |
| WO | 2019-117440 A1 | 6/2019 |

OTHER PUBLICATIONS

Seon-Jeong Lim et al., 'Organic-on-silicon complementary metal-oxide-semiconductor colour image sensors' *Scientific Reports*, 5:7708, Jan. 2015.

Extended European Search Report dated Mar. 19, 2021, issued in corresponding European Patent Application No. 20204869.0.

Paul Sullivan et al., 'Halogenated Boron Subphthalocyanines as Light Harvesting Electron Acceptors in Organic Photovoltaics' *Advanced Energy Materials*, vol. 1, No. 3, May 2011, pp. 352-355.

Mikio Ihama et al., 'CMOS Image Sensor with a Thin Overlaid Panchromatic Organic Photoconductive Layer for Sensors with Reduced Pixel Size' *IDW*, 2009, INP 1-4, pp. 2123-2126.

Japanese Office Action dated Aug. 27, 2024 for corresponding Japanese Patent Application No. 2020-185692 and its English-language translation.

PHOTOELECTRIC CONVERSION DEVICE AND SENSOR AND ELECTRONIC DEVICE

CROSS-REFERENCE TO RELATED APPLICATION

This application claims priority to and the benefit of Korean Patent Application No. 10-2019-0141158, filed in the Korean Intellectual Property Office on Nov. 6, 2019, the entire contents of which are incorporated herein by reference.

BACKGROUND

1. Field

A photoelectric conversion device, a sensor, and an electronic device are disclosed.

2. Description of Related Art

A photoelectric conversion device converts light into an electrical signal using photoelectric effects. The photoelectric conversion device includes a photodiode and a photo transistor, and the like, and it may be applied to a sensor or a photodetector.

Sensors are increasingly demanding higher resolution, resulting in smaller pixel sizes. At present, a silicon photodiode is widely used, but it may have deteriorated sensitivity since silicon photodiodes have a smaller absorption area due to small pixels. Accordingly, an organic material that is capable of replacing silicon has been researched.

The organic material may have a high extinction coefficient and be configured to selectively absorb light in a particular wavelength region depending on a molecular structure, and thus may simultaneously replace a photodiode and a color filter and resultantly improve sensitivity and contribute to high integration.

However, the organic material may differ from silicon due to its high binding energy and recombination behavior. It may be difficult to accurately predict the characteristics of organic materials, which may make it difficult to easily control properties required for photoelectric conversion devices.

SUMMARY

Embodiment embodiments provide a photoelectric conversion device capable of reducing remaining charge carriers and dark current and improving photoelectric conversion efficiency, charge carrier extraction characteristics, and thermal stability.

Example embodiments provide a sensor including the photoelectric conversion device.

Example embodiments provide an electronic device including the photoelectric conversion device or the sensor.

According to example embodiments, a photoelectric conversion device includes a first electrode and a second electrode, a photoelectric conversion layer between the first electrode and the second electrode, the photoelectric conversion layer including a p-type semiconductor and an n-type semiconductor, and an organic buffer layer between the first electrode and the photoelectric conversion layer. The organic buffer layer includes an organic buffer material. A difference between a LUMO energy level of the organic buffer material and a LUMO energy level of the n-type semiconductor is greater than or equal to about 1.2 eV and the organic buffer material includes at least three carbazole moieties.

In some embodiments, the LUMO energy level of the organic buffer material may be about 1.2 eV to about 3.0 eV, and the LUMO energy of the n-type semiconductor may be about 3.6 eV to about 4.8 eV.

In some embodiments, a difference between a HOMO energy level of the organic buffer material and a HOMO energy level of the p-type semiconductor may be less than or equal to about 0.5 eV.

In some embodiments, the HOMO energy level of the organic buffer material and the HOMO energy level of the p-type semiconductor may be within about 5.0 eV to about 6.0 eV, respectively.

In some embodiments, a difference between the HOMO energy level of the organic buffer material and the HOMO energy level of the p-type semiconductor may be about 0 eV to about 0.5 eV, and a difference between the LUMO energy level of the organic buffer material and the LUMO energy level of the n-type semiconductor is about 1.2 eV to about 3.6 eV.

In some embodiments, the organic buffer material may be represented by Chemical Formula 1.

[Chemical Formula 1]

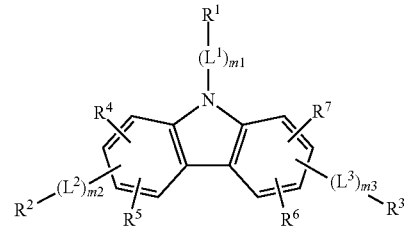

In Chemical Formula 1, $L^1$ to $L^3$ are independently a substituted or unsubstituted C6 to C20 arylene group, $R^1$ to $R^7$ are independently hydrogen, a substituted or unsubstituted C1 to C30 alkyl group, a substituted or unsubstituted C1 to C30 alkoxy group, a substituted or unsubstituted C6 to C20 aryl group, a substituted or unsubstituted C3 to C20 heteroaryl group, a substituted or unsubstituted carbazolyl group, a halogen, a cyano group, or a combination thereof, at least two of $R^1$ to $R^3$ are a substituted or unsubstituted carbazolyl group, and $m^1$ to $m^3$ are independently 0 or 1.

In some embodiments, the organic buffer material may be represented by one of Chemical Formulae 1A to 1C.

[Chemical Formula 1A]

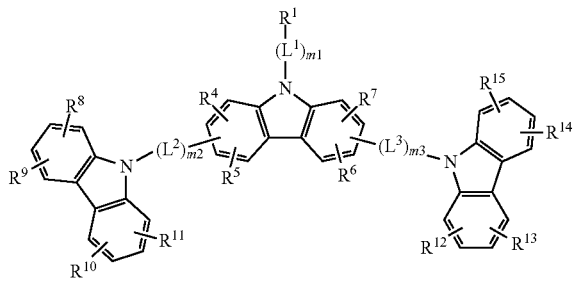

-continued

[Chemical Formula 1B]

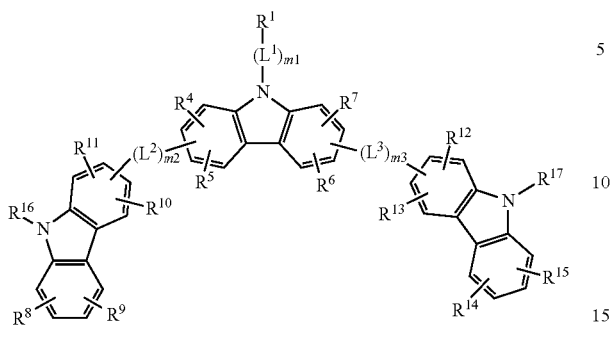

[Chemical Formula 1C]

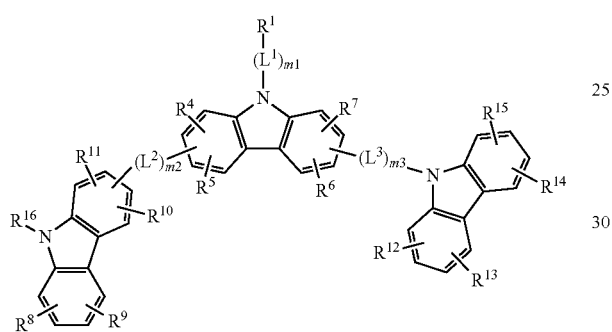

[Chemical Formula 1D]

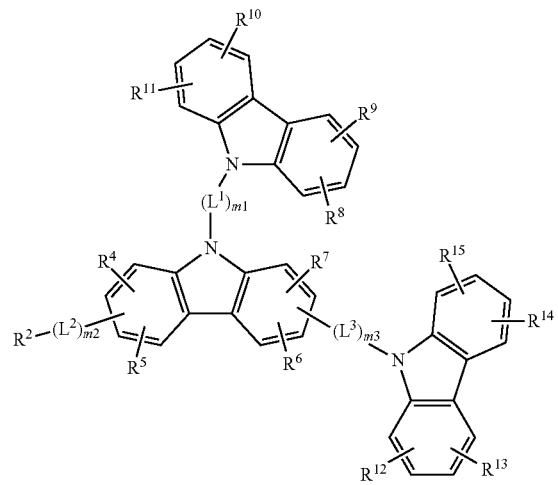

[Chemical Formula 1E]

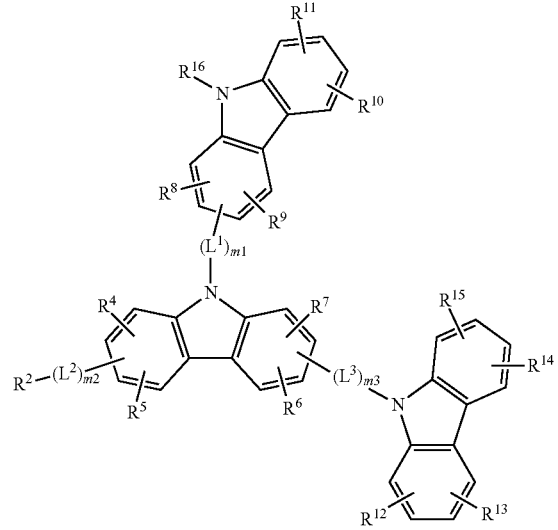

[Chemical Formula 1F]

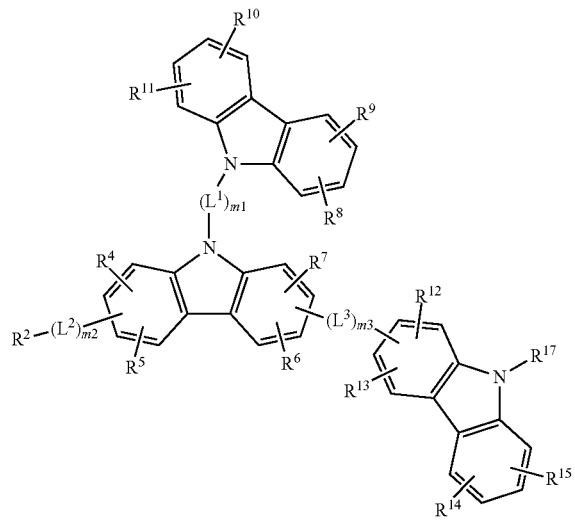

In Chemical Formulae 1A to 1C, $L^1$ to $L^3$ are independently a substituted or unsubstituted C6 to C20 arylene group, $R^1$ and $R^4$ to $R^{17}$ are independently hydrogen, a substituted or unsubstituted C1 to C30 alkyl group, a substituted or unsubstituted C1 to C30 alkoxy group, a substituted or unsubstituted C6 to C20 aryl group, a substituted or unsubstituted C3 to C20 heteroaryl group, a substituted or unsubstituted carbazolyl group, a halogen, a cyano group, or a combination thereof, and $m^1$ to $m^3$ are independently 0 or 1.

In some embodiments, in Chemical Formulae 1A to 1C, $R^1$ and $R^4$ to $R^{17}$ may independently be hydrogen, a substituted or unsubstituted phenyl group, a substituted or unsubstituted biphenyl group, or a substituted or unsubstituted naphthyl group.

In some embodiments, in Chemical Formulae 1A to 1C, $L^1$ to $L^3$ may independently be a substituted or unsubstituted phenylene group, a substituted or unsubstituted biphenylene group, or a substituted or unsubstituted naphthylene group.

In some embodiments, in Chemical Formulae 1A to 1C, three of $R^1$, $R^4$ to $R^{17}$ and $L^1$ to $L^3$ may be a substituted or unsubstituted phenyl group or a substituted or unsubstituted phenylene group.

In some embodiments, the organic buffer material may be represented by one of Chemical Formulae 1D to 1G.

[Chemical Formula 1G]

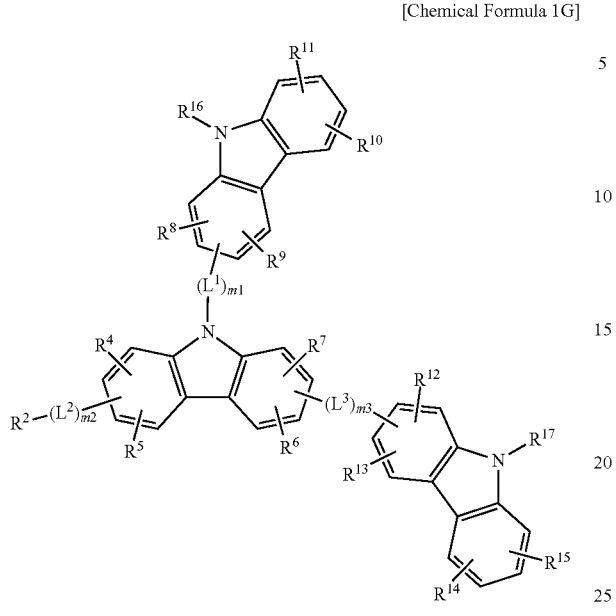

[Chemical Formula 1-1]

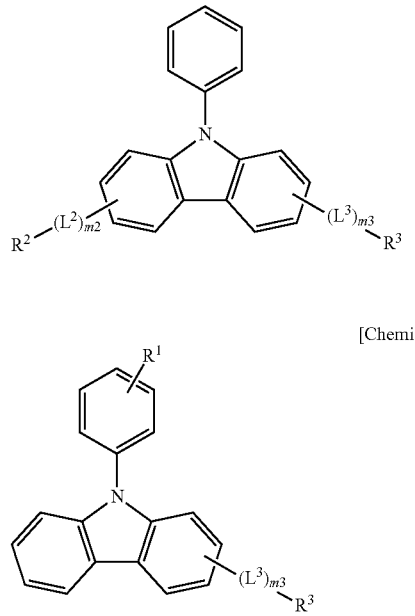

[Chemical Formula 1-2]

[Chemical Formula 1-3]

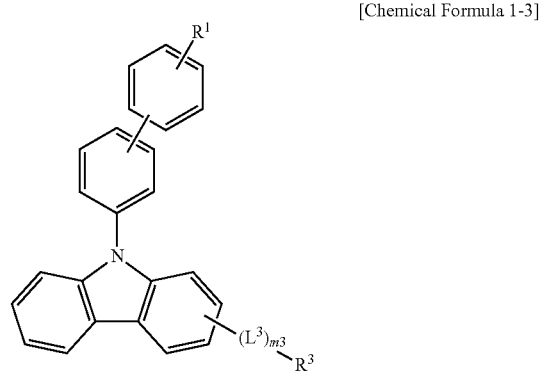

[Chemical Formula 1-4]

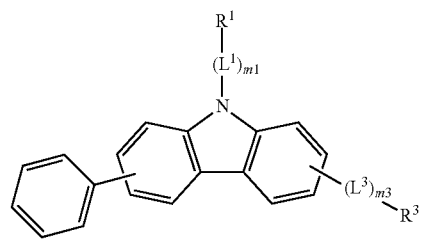

In Chemical Formulae 1D to 1G, $L^1$ to $L^3$ are independently a substituted or unsubstituted C6 to C20 arylene group, $R^2$ and $R^4$ to $R^{17}$ are independently hydrogen, a substituted or unsubstituted C1 to C30 alkyl group, a substituted or unsubstituted C1 to C30 alkoxy group, a substituted or unsubstituted C6 to C20 aryl group, a substituted or unsubstituted C3 to C20 heteroaryl group, a substituted or unsubstituted carbazolyl group, a halogen, a cyano group, or a combination thereof, and $m^1$ to $m^3$ are independently 0 or 1.

In some embodiments, in Chemical Formulae 1D to 1G, $R^2$ and $R^4$ to $R^{17}$ may independently be hydrogen, a substituted or unsubstituted phenyl group, a substituted or unsubstituted biphenyl group, or a substituted or unsubstituted naphthyl group.

In some embodiments, in Chemical Formulae 1D to 1G, $L^1$ to $L^3$ may independently be a substituted or unsubstituted phenylene group, a substituted or unsubstituted biphenylene group, or a substituted or unsubstituted naphthylene group.

In some embodiments, in Chemical Formulae 1D to 1G, three of $R^2$, $R^4$ to $R^{17}$ and $L^1$ to $L^3$ may be a substituted or unsubstituted phenyl group or a substituted or unsubstituted phenylene group.

In some embodiments, in Chemical Formula 1, two of $R^1$ to $R^3$ may be a substituted or unsubstituted carbazolyl group and a remaining one of $R^1$ to $R^3$ may be hydrogen, a substituted or unsubstituted phenyl group, a substituted or unsubstituted biphenyl group, or a substituted or unsubstituted naphthyl group.

In some embodiments, the organic buffer material may include three carbazole moieties and three phenyl moieties.

In some embodiments, the organic buffer material may be represented by one of Chemical Formulae 1-1 to 1-4.

In Chemical Formulae 1-1 to 1-4, $L^1$ to $L^3$ are independently a phenyl group, $m^1$ to $m^3$ are independently 0 or 1, and $R^1$ to $R^3$ are independently a carbazolyl group or a phenyl-substituted carbazolyl group.

In some embodiments, in Chemical Formulae 1-1 to 1-4, $R^1$ to $R^3$ may independently be one of the groups listed in Group 1.

[Group 1]

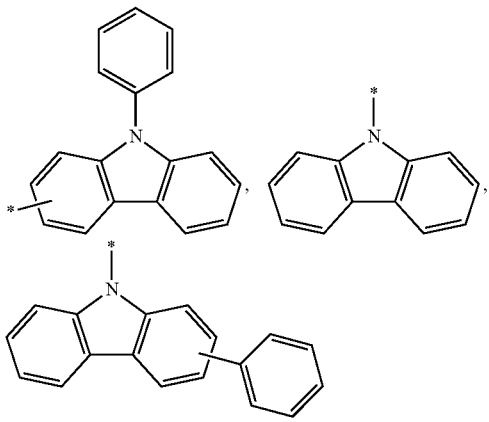

In Group 1, * is a linking point.

In some embodiments, the organic buffer material may be represented by Chemical Formula 1-2-1 or 1-3-1.

[Chemical Formula 1-2-1]

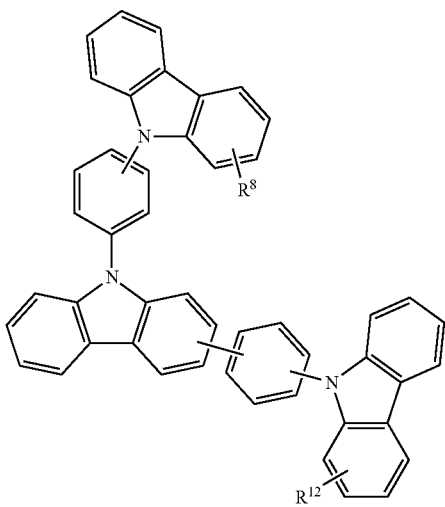

[Chemical Formula 1-3-1]

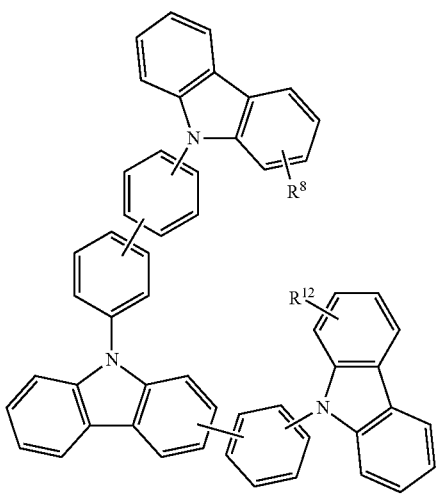

In Chemical Formula 1-2-1 or 1-3-1, $R^8$ and $R^{12}$ are independently hydrogen or a phenyl group.

In some embodiments, the p-type semiconductor, the n-type semiconductor, or both the p-type semiconductor and the n-type semiconductor independently may be a light-absorbing material having a maximum absorption wavelength in one of a red wavelength spectrum, a green wavelength spectrum, a blue wavelength spectrum, and an infra-red wavelength spectrum.

According to example embodiments, a photoelectric conversion device includes a photoelectric conversion layer including a light-absorbing material, the photoelectric conversion layer being configured to convert light absorbed by the light-absorbing material into an electrical signal; and an organic buffer layer adjacent to the photoelectric conversion layer. An absorption spectrum of the photoelectric conversion layer has a maximum absorption wavelength in one of a red wavelength spectrum, a green wavelength spectrum, a blue wavelength spectrum, and an infra-red wavelength spectrum. The organic buffer layer includes an organic buffer material including at least three carbazole moieties and has an energy bandgap of greater than or equal to about 2.8 eV.

In some embodiments, the organic buffer material may include three carbazole moieties and three phenyl moieties.

According to example embodiments, a sensor including the photoelectric conversion device is provided.

In some embodiments, the sensor may be an organic CMOS image sensor.

In some embodiments, the organic CMOS image sensor may further include a semiconductor substrate under the photoelectric conversion device.

According to example embodiment, an electronic device including the photoelectric conversion device or the sensor is provided.

According to example embodiments, a compound represented by Chemical Formula 1D-1 is provided.

[Chemical Formula 1D-1]

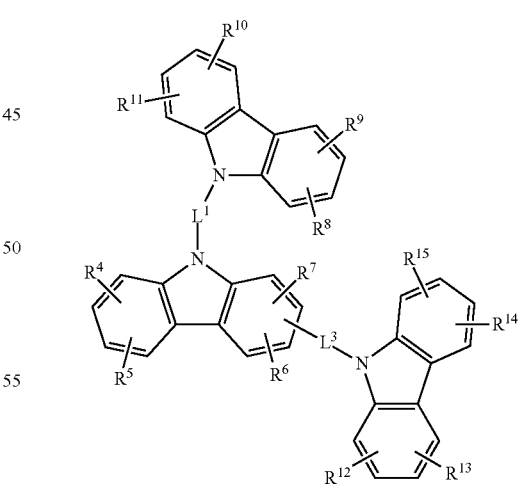

In Chemical Formula 1D-1,
$L^1$ and $L^3$ are independently a substituted or unsubstituted C6 to C20 arylene group, and
$R^4$ to $R^{15}$ are independently hydrogen, a substituted or unsubstituted C1 to C30 alkyl group, a substituted or unsubstituted C1 to C30 alkoxy group, a substituted or unsubstituted C6 to C20 aryl group, a substituted or unsubstituted C3 to C20 heteroaryl group, a substituted or unsubstituted carbazolyl group, a halogen, a cyano group, or a combination thereof.

In some embodiments, in Chemical Formula 1D-1, $R^4$ to $R^{15}$ may independently be hydrogen, a substituted or unsubstituted phenyl group, a substituted or unsubstituted biphenyl group, or a substituted or unsubstituted naphthyl group.

In Chemical Formula 1D-1, $L^1$ and $L^3$ may independently be a substituted or unsubstituted phenylene group, a substituted or unsubstituted biphenylene group, or a substituted or unsubstituted naphthylene group.

In some embodiments, the compound may include three phenyl moieties.

The compound may be represented by Chemical Formula 1-2-1 or 1-3-1.

[Chemical Formula 1-2-1]

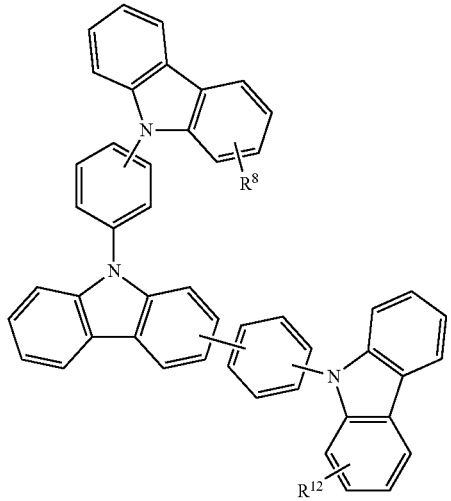

[Chemical Formula 1-3-1]

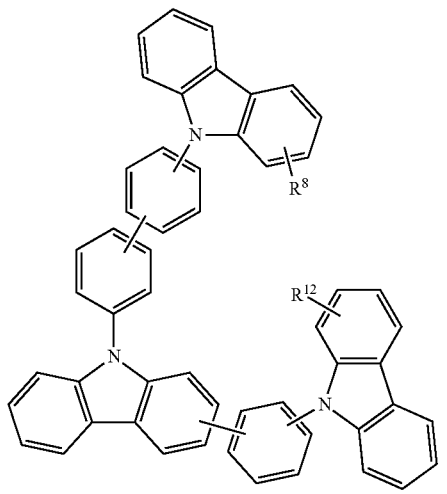

In Chemical Formula 1-2-1 or 1-3-1, $R^8$ and $R^{12}$ are independently hydrogen or a phenyl group.

Remaining charge carriers at an interface of two layers and dark current may be efficiently reduced and photoelectric conversion efficiency, charge carrier extraction characteristics and thermal stability may be improved.

According to example embodiments, a photoelectric conversion device includes a first electrode; a second electrode on the first electrode; a photoelectric conversion layer between the first electrode and the second electrode; and an organic buffer layer between the first electrode and the photoelectric conversion layer. The organic buffer layer may include an organic buffer material represented by Chemical Formula 1.

[Chemical Formula 1]

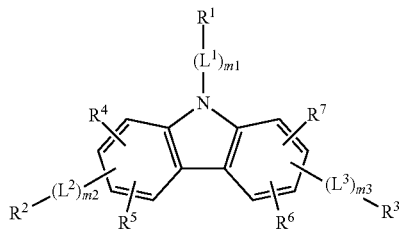

In Chemical Formula 1,
$L^1$ to $L^3$ are independently a substituted or unsubstituted C6 to C20 arylene group,
$R^1$ to $R^7$ are independently hydrogen, a substituted or unsubstituted C1 to C30 alkyl group, a substituted or unsubstituted C1 to C30 alkoxy group, a substituted or unsubstituted C6 to C20 aryl group, a substituted or unsubstituted C3 to C20 heteroaryl group, a substituted or unsubstituted carbazolyl group, a halogen, a cyano group, or a combination thereof, at least two of $R^1$ to $R^3$ are a substituted or unsubstituted carbazolyl group, and $m^1$ to $m^3$ are independently 0 or 1.

In some embodiments, the organic buffer material may have a LUMO energy level in a range of about 1.2 eV to about 3.0 eV and a HOMO energy level of about 5.0 eV to about 6.0 eV, the photoelectric conversion layer may include a p-type semiconductor and an n-type semiconductor, the LUMO energy of the n-type semiconductor may be about 3.6 eV to about 4.8 eV, and the HOMO energy level of the p-type semiconductor may be about 5.0 eV to about 6.0 eV.

In some embodiments, in Chemical Formula 1, two of $R^1$ to $R^3$ may be a substituted or unsubstituted carbazolyl group. A remaining one of $R^1$ to $R^3$ may be hydrogen, a substituted or unsubstituted phenyl group, a substituted or unsubstituted biphenyl group, or a substituted or unsubstituted naphthyl group.

In some embodiments, a sensor may include the photoelectric conversion device.

In some embodiments, an electronic device may include the sensor.

DETAILED DESCRIPTION

Figure 1:
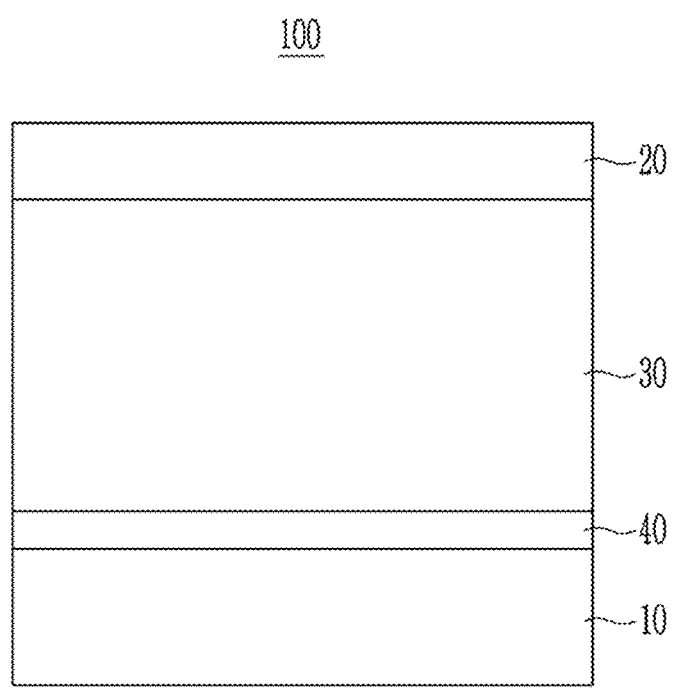
FIG. 1 is a cross-sectional view showing an example of a photoelectric conversion device according to example embodiments.

Example embodiments will hereinafter be described in detail, and may be easily performed by a person skilled in the related art. However, this disclosure may be embodied in many different forms and is not to be construed as limited to the example embodiments set forth herein.

In the drawings, the thickness of layers, films, panels, regions, etc., are exaggerated for clarity.

It will be understood that when an element such as a layer, film, region, or substrate is referred to as being "on" another element, it may be directly on the other element or intervening elements may also be present. In contrast, when an element is referred to as being "directly on" another element, there are no intervening elements present.

Hereinafter, as used herein, when a definition is not otherwise provided, "substituted" refers to replacement of hydrogen of a compound by a substituent selected from a halogen atom, a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a silyl group, a C1 to C20 alkyl group, a C2 to C20 alkenyl group, a C2 to C20 alkynyl group, a C6 to C30 aryl group, a C7 to C30 arylalkyl group, a C1 to C30 alkoxy group, a C1 to C20 heteroalkyl group, a C3 to C20 heteroaryl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and a combination thereof.

As used herein, when specific definition is not otherwise provided, "hetero" refers to one including 1 to 4 heteroatoms selected from N, O, S, Se, Te, Si, and P.

Hereinafter, "combination" refers to a mixture or a stacked structure of two or more.

As used herein, when specific definition is not otherwise provided, an energy level refers to the highest occupied molecular orbital (HOMO) energy level and/or the lowest unoccupied molecular orbital (LUMO) energy level.

Hereinafter, a work function or an energy level is expressed as an absolute value from a vacuum level (0 V). In addition, when the work function or the energy level is referred to be deep, high, or large, it may have a large absolute value based on "0 eV" of the vacuum level, while when the work function or the energy level is referred to be shallow, low, or small, it may have a small absolute value based on "0 eV" of the vacuum level.

Hereinafter, a photoelectric conversion device according to an embodiment is described with reference to the drawings.

FIG. 1 is a cross-sectional view showing an example of a photoelectric conversion device according to some embodiments.

Referring to FIG. 1, a photoelectric conversion device 100 according to some embodiments includes a first electrode 10, a second electrode 20, a photoelectric conversion layer 30, and an organic buffer layer 40.

A substrate (not shown) may be disposed at the side of the first electrode 10 or the second electrode 20. The substrate may be, for example, an inorganic substrate such as a glass plate or a silicon wafer, or an organic substrate made of an organic material such as polycarbonate, polymethyl methacrylate, polyethylene terephthalate, polyethylene naphthalate, polyamide, polyethersulfone, or a combination thereof. The substrate may be omitted.

One of the first electrode 10 and the second electrode 20 is an anode and the other is a cathode. For example, the first electrode 10 may be an anode and the second electrode 20 may be a cathode. For example, the first electrode 10 may be a cathode and the second electrode 20 may be an anode.

At least one of the first electrode 10 and the second electrode 20 may be a transparent electrode. Herein, the transparent electrode may have a high light transmittance of greater than or equal to about 80%. The transparent electrode may include for example at least one of an oxide conductor, a carbon conductor, and a metal thin film. The oxide conductor may include for example at least one of indium tin oxide (ITO), indium zinc oxide (IZO), zinc tin oxide (ZTO), aluminum tin oxide (AITO), and aluminum zinc oxide (AZO), the carbon conductor may include at least one of graphene and carbon nanostructures, and the metal thin film may be a very thin film including aluminum (Al), magnesium (Mg), silver (Ag), gold (Au), an alloy thereof, or a combination thereof.

One of the first electrode 10 and the second electrode 20 may be a reflective electrode. Herein, the reflective electrode may have, for example, a light transmittance of less than about 10% or high reflectance of greater than or equal to about 5%. The reflective electrode may include a reflective conductor such as a metal and may include, for example aluminum (Al), silver (Ag), gold (Au), or an alloy thereof.

For example, each of the first electrode 10 and the second electrode 20 may be a transparent electrode, and one of the first electrode 10 and the second electrode 20 may be a light-receiving electrode disposed at a light receiving side.

For example, the first electrode 10 may be a transparent electrode, the second electrode 20 may be a reflective electrode, and the first electrode 10 may be a light-receiving electrode.

For example, the first electrode 10 may be a reflective electrode, the second electrode 20 may be a transparent electrode, and the second electrode 20 may be a light-receiving electrode.

The photoelectric conversion layer 30 may be disposed between the first electrode 10 and the second electrode 20.

The photoelectric conversion layer 30 may be configured to absorb light in at least one part in a wavelength spectrum and may be configured to convert the absorbed light into an electrical signal. It may be configured to convert, for example, a portion of light in a blue wavelength spectrum (hereinafter, referred to as "blue light"), light in a green wavelength spectrum (hereinafter, referred to as "green light"), light in a red wavelength spectrum (hereinafter, referred to as "red light"), and light in an infra-red wavelength spectrum (hereinafter, referred to as "infra-red light") into an electrical signal.

For example, the photoelectric conversion layer 30 may be configured to selectively absorb at least one of the blue light, the green light, the red light, and the infra-red light and to convert the absorbed light into an electrical signal. Herein, the selective absorption of at least one of the blue light, the green light, the red light, and the infra-red light means that a absorption spectrum has a maximum absorption wavelength (λmax) in one of greater than or equal to about 380 nm and less than about 500 nm, about 500 nm to about 600 nm, greater than about 600 nm and less than or equal to about 700 nm, and greater than about 700 nm and less than or equal to about 3000 nm, and a absorption spectrum in the corresponding wavelength spectrum is remarkably higher than those in the other wavelength regions. Herein "significantly high" means that about 70% to about 100%, about 75% to about 100%, about 80% to about 100%, about 85% to about 100%, about 90% to about 100%, or about 95% to about 100% relative to a total area of the absorption spectrum may belong to the corresponding wavelength spectrum.

The photoelectric conversion layer 30 may include at least one p-type semiconductor and at least one n-type semiconductor, and the at least one p-type semiconductor and the at least one n-type semiconductor may form a pn junction. The photoelectric conversion layer 30 may receive light from the outside to generate excitons, and the generated excitons may be separated into holes and electrons.

The p-type semiconductor and the n-type semiconductor may be light-absorbing materials, and for example, at least one of the p-type semiconductor and the n-type semiconductor may be an organic light-absorbing material.

For example, at least one of the p-type semiconductor and the n-type semiconductor may be a light-absorbing material having wavelength selectivity which configured to selectively absorb light in a desired and/or alternatively predetermined wavelength spectrum. For example, at least one of the p-type semiconductor and the n-type semiconductor may be an organic light-absorbing material having wavelength selectivity. The p-type semiconductor and the n-type semiconductor may have maximum absorption wavelengths ($\lambda_{max}$) in the same or different wavelength spectrums.

For example, at least one of the p-type semiconductor and the n-type semiconductor may be a light-absorbing material having a maximum absorption wavelength ($\lambda_{max}$) in the wavelength spectrum of about 500 nm to about 600 nm, and for example, a light-absorbing material having a maximum absorption wavelength ($\lambda_{max}$) in the wavelength spectrum of about 520 nm to about 580 nm.

For example, at least one of the p-type semiconductor and the n-type semiconductor may be an organic light-absorbing material having a maximum absorption wavelength ($\lambda_{max}$) in a wavelength spectrum of about 500 nm to about 600 nm, for example, an organic light-absorbing material having a maximum absorption wavelength ($\lambda_{max}$) in a wavelength spectrum of about 520 nm to about 580 nm.

For example, the p-type semiconductor may be an organic light-absorbing material having a maximum absorption wavelength ($\lambda_{max}$) in a wavelength spectrum of about 500 nm to about 600 nm, for example, an organic light-absorbing material having a maximum absorption wavelength ($\lambda_{max}$) in a wavelength spectrum of about 520 nm to about 580 nm.

For example, the HOMO energy level of the p-type semiconductor may be about 5.0 eV to about 6.0 eV, within the range, about 5.1 eV to about 5.9 eV, about 5.2 eV to about 5.8 eV, or about 5.3 eV to about 5.8 eV. For example, the LUMO energy level of the p-type semiconductor may be about 2.7 eV to about 4.3 eV, within the range, about 2.8 eV to about 4.1 eV, or about 3.0 eV to about 4.0 eV. For example, the energy band gap of the p-type semiconductor may be about 1.7 eV to about 2.3 eV, within the range, about 1.8 eV to about 2.2 eV, or about 1.9 eV to about 2.1 eV.

For example, the p-type semiconductor may be an organic material having a core structure including an electron donating moiety (EDM), a π-conjugated linking moiety (LM), and an electron accepting moiety (EMA).

For example, the p-type semiconductor may be represented by Chemical Formula A, but is not limited thereto.

EDM1-LM1-EAM1      [Chemical Formula A]

In Chemical Formula A,
EDM1 may be an electron donating moiety,
EAM1 may be an electron accepting moiety, and
LM1 may be a π-conjugated linking moiety that links the electron donating moiety with the electron accepting moiety.

For example, the p-type semiconductor represented by Chemical Formula A may be, for example, represented by Chemical Formula A-1.

[Chemical Formula A-1]

$$\begin{array}{c}\text{Ar}^{1a}\\\diagdown\\\text{N}\\\diagup\\\text{Ar}^{2a}\end{array}\begin{array}{c}R^{3a}\\|\\\diagup\diagdown\\\text{X}\diagdown\diagup\diagdown\\|\quad\quad\text{Ar}\\\diagup\diagdown\diagup\\\text{O}\\R^{1a}\quad R^{2a}\end{array}$$

In Chemical Formula A-1,
X may be O, S, Se, Te, SO, SO$_2$, or SiR$^a$R$^b$,
Ar may be a substituted or unsubstituted C6 to C30 arylene group, a substituted or unsubstituted C3 to C30 heterocyclic group, or a fused ring of the foregoing two or more,
Ar$^{1a}$ and Ar$^{2a}$ are independently a substituted or unsubstituted C6 to C30 aryl group or a substituted or unsubstituted C3 to C30 heteroaryl group,
Ar$^{1a}$ and Ar$^{2a}$ may independently be present alone or may be linked with each other to form a fused ring, and
R$^{1a}$ to R$^{3a}$, R$^a$ and R$^b$ may independently be hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, or a combination thereof.

For example, in Chemical Formula A-1, Ar$^{1a}$ and Ar$^{2a}$ may independently be one of a substituted or unsubstituted phenyl group, a substituted or unsubstituted naphthyl group, a substituted or unsubstituted anthracenyl group, a substituted or unsubstituted phenanthrenyl group, a substituted or unsubstituted pyridinyl group, a substituted or unsubstituted pyridazinyl group, a substituted or unsubstituted pyrimidinyl group, a substituted or unsubstituted pyrazinyl group, a substituted or unsubstituted quinolinyl group, a substituted or unsubstituted isoquinolinyl group, a substituted or unsubstituted naphthyridinyl group, a substituted or unsubstituted cinnolinyl group, a substituted or unsubstituted quinazolinyl group, a substituted or unsubstituted phthalazinyl group, a substituted or unsubstituted benzotriazinyl group, a substituted or unsubstituted pyridopyrazinyl group, a substituted or unsubstituted pyridopyrimidinyl group, or a substituted or unsubstituted pyridopyridazinyl group.

For example, $Ar^{1a}$ and $Ar^{2a}$ of Chemical Formula A-1 may be linked with each other to form a ring, and for example, $Ar^{1a}$ and $Ar^{2a}$ may be linked with each other by one of a single bond, $-(CR^gR^h)_{n2}-$ (n2 is 1 or 2), $-O-$, $-S-$, $-Se-$, $-N=$, $-NR^i-$, $-SiR^jR^k-$ and $-GeR^lR^m-$ to form a ring. Herein, $R^g$ to $R^m$ may independently be hydrogen, a substituted or unsubstituted C1 to C30 alkyl group, a substituted or unsubstituted C6 to C30 aryl group, a substituted or unsubstituted C3 to C30 heteroaryl group, a substituted or unsubstituted C1 to C6 alkoxy group, a halogen, a cyano group, or a combination thereof.

The p-type semiconductor represented by Chemical Formula A may be, for example, represented by Chemical Formula A-2 or A-3.

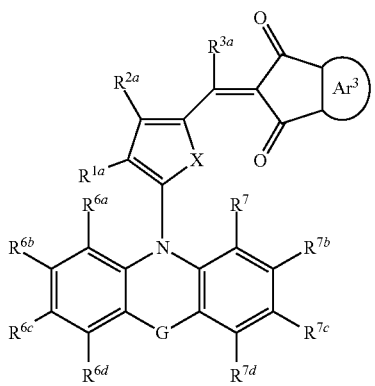
[Chemical Formula A-2]

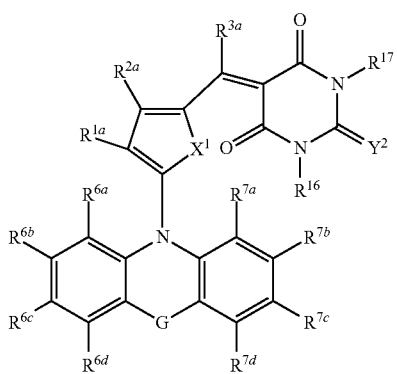
[Chemical Formula A-3]

In Chemical Formula A-2 or A-3,

X may be O, S, Se, Te, SO, $SO_2$, or $SiR^aR^b$, Ara may be a substituted or unsubstituted C6 to C30 arylene group, a substituted or unsubstituted C3 to C30 heterocyclic group, or a fused ring of the foregoing two or more, $R^{1a}$ to $R^{3a}$, $R^a$ and $R^b$ may independently be hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, or a combination thereof, G may be one of a single bond, $-(CR^gR^h)_{n2}-$ (n2 is 1 or 2), $-O-$, $-S-$, $-Se-$, $-N=$, $-NR^i-$, $-SiR^jR^k-$, or $-GeR^lR^m-$, wherein $R^g$ to $R^m$ may independently be hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, or a combination thereof, and $R^g$ and $R^h$, $R^i$ and $R^k$, and $R^l$ and $R^m$ may independently be present alone or linked with each other to form a ring, $Y^2$ may be O, S, Se, Te, or $C(R^q)(CN)$ (wherein $R^q$ is hydrogen, a cyano group (—CN), or a C1 to C10 alkyl group), $R^{6a}$ to $R^{6d}$, $R^{7a}$ to $R^{7d}$, $R^{16}$ and $R^{17}$ may independently be hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, or a combination thereof, $R^{6a}$ to $R^{6d}$ may independently be present alone or adjacent two thereof may be linked with each other to provide a fused ring, and $R^{7a}$ to $R^{7d}$ may independently be present alone or adjacent two thereof may be linked with each other to provide a fused ring.

For example, Ara of Chemical Formula A-2 may be benzene, naphthylene, anthracene, thiophene, selenophene, tellurophene, pyridine, pyrimidine, or a fused ring of the foregoing two or more.

For example, the n-type semiconductor may be an organic material, an inorganic material or organic/inorganic material.

For example, the LUMO energy level of the n-type semiconductor may be about 3.6 eV to about 4.8 eV, within the range, about 3.8 eV to about 4.6 eV, or about 3.9 eV to about 4.5 eV.

For example, the n-type semiconductor may be, for example, a thiophene or a thiophene derivative, a fullerene or a fullerene derivative, but is not limited thereto.

The photoelectric conversion layer 30 may be an intrinsic layer (1 layer) in which a p-type semiconductor and an n-type semiconductor are blended in a bulk heterojunction form. Herein, the p-type semiconductor and the n-type semiconductor may be blended in a volume ratio (thickness ratio) of about 1:9 to about 9:1, and may be blended within the range, for example, in a volume ratio (thickness ratio) of about 2:8 to about 8:2, in a volume ratio (thickness ratio) of about 3:7 to about 7:3, in a volume ratio (thickness ratio) of about 4:6 to 6:4, or in a volume ratio (thickness ratio) of about 5:5.

The photoelectric conversion layer 30 may include a bilayer including a p-type layer including the aforementioned p-type semiconductor and an n-type layer including the aforementioned n-type semiconductor. Herein, a thickness ratio of the p-type layer and the n-type layer may be about 1:9 to about 9:1, for example about 2:8 to about 8:2, about 3:7 to about 7:3, about 4:6 to about 6:4, or about 5:5.

The photoelectric conversion layer 30 may further include a p-type layer and/or an n-type layer in addition to the intrinsic layer. The p-type layer may include the aforementioned p-type semiconductor and the n-type layer may include the aforementioned n-type semiconductor. For example, the p-type layer and the n-type layer may be included in various combinations of p-type layer/I layer, I layer/n-type layer, p-type layer/I layer/n-type layer, and the like.

The photoelectric conversion layer 30 may have a thickness of about 1 nm to about 500 nm, within the range, a thickness of about 5 nm to about 300 nm. When the photoelectric conversion layer 30 has a thickness within the range, the active layer may be configured to effectively absorb light, effectively separate into holes and electrons, and transfer them, thereby effectively improving photoelectronic conversion efficiency.

The organic buffer layer 40 may be disposed between the first electrode 10 and the second electrode 20, and may be disposed between the first electrode 10 and the photoelectric conversion layer 30. For example, the organic buffer layer 40 may be in contact with the photoelectric conversion layer 30. For example, one surface of the organic buffer layer 40 may be in contact with the photoelectric conversion layer 30 and the other surface of the organic buffer layer 40 may be in contact with the first electrode 10.

The organic buffer layer 40 may be configured to effectively extract first charge carriers (for example, holes) separated from the photoelectric conversion layer 30 toward the first electrode 10, while simultaneously prevent second charge carriers (e.g., electrons) from being injected reversely to the photoelectric conversion layer 30 from the first electrode 10 when a voltage is applied. Accordingly, electrical characteristics of the photoelectric conversion device 100 may be improved by increasing the photoelectric conversion efficiency of the photoelectric conversion device 100 and at the same time effectively reducing dark current and remaining charge carriers.

The organic buffer layer 40 may include an organic buffer material capable of implementing the aforementioned properties.

For example, the difference between the HOMO energy level of the organic buffer material and the HOMO energy level of the p-type semiconductor of the photoelectric conversion layer 30 may be relatively small. For example, the difference between the HOMO energy level of the organic buffer material and the HOMO energy level of the p-type semiconductor may be less than or equal to about 0.5 eV, within the range, about 0 eV to about 0.5 eV, about 0 eV to about 0.4 eV, about 0 eV to about 0.3 eV, about 0 eV to about 0.2 eV, or about 0 eV to about 0.1 eV. For example, each of the HOMO energy level of the organic buffer material and the HOMO energy level of the p-type semiconductor may be about 5.0 eV to about 6.0 eV.

Herein, the HOMO energy level may be evaluated by the photoelectron amount emitted by irradiating UV light to the thin film using AC-3 (Riken Keiki Co., LTD.). The HOMO energy level of the organic buffer material and the HOMO energy level of the p-type semiconductor are expressed as absolute values, and the difference between the HOMO energy level of the organic buffer material and the HOMO energy level of the p-type semiconductor may be the large value of the absolute value minus the small value of the absolute value.

For example, the difference between the LUMO energy level of the organic buffer material and the LUMO energy level of the n-type semiconductor of the photoelectric conversion layer 30 may be relatively large, so that it is possible to form a sufficient energy barrier between the organic buffer layer and the photoelectric conversion layer to prevent second charge carriers (for example, electrons) from being reversely injected into the photoelectric conversion layer 30. For example, the difference between the LUMO energy level of organic buffer material and the LUMO energy level of the n-type semiconductor may be greater than or equal to about 1.2 eV, within the range, greater than or equal to about 1.3 eV, greater than or equal to about 1.4 eV, greater than or equal to about 1.5 eV, greater than or equal to about 1.6 eV, greater than or equal to about 1.7 eV, greater than or equal to about 1.9 eV, greater than or equal to about 2.0 eV, greater than or equal to about 2.1 eV, or greater than or equal to about 2.3 eV, within the range, about 1.2 eV to about 4.0 eV, about 1.2 eV to about 3.8 eV, about 1.2 eV to about 3.6 eV, about 1.3 eV to about 4.0 eV, about 1.3 eV to about 3.8 eV, about 1.3 eV to about 3.6 eV, about 1.4 eV to about 4.0 eV, about 1.4 eV to about 3.8 eV, about 1.4 eV to about 3.6 eV, about 1.5 eV to about 4.0 eV, about 1.5 eV to about 3.8 eV, about 1.5 eV to about 3.6 eV, about 1.6 eV to about 4.0 eV, about 1.6 eV to about 3.8 eV, about 1.6 eV to about 3.6 eV, about 1.7 eV to about 4.0 eV, about 1.7 eV to about 3.8 eV, about 1.7 eV to about 3.6 eV, about 1.9 eV to about 4.0 eV, about 1.9 eV to about 3.8 eV, about 1.9 eV to about 3.6 eV, about 2.0 eV to about 4.0 eV, about 2.0 eV to about 3.8 eV, about 2.0 eV to about 3.6 eV, about 2.1 eV to about 4.0 eV, about 2.1 eV to about 3.8 eV, about 2.1 eV to about 3.6 eV, about 2.3 eV to about 4.0 eV, about 2.3 eV to about 3.8 eV, or about 2.3 eV to about 3.6 eV. For example, the LUMO energy level of the organic buffer material may be less than or equal to about 3.0 eV, within the range, less than or equal to about 2.9 eV, less than or equal to about 2.8 eV, less than or equal to about 2.7 eV, less than or equal to about 2.6 eV, less than or equal to about 2.5 eV, less than or equal to about 2.4 eV, or less than or equal to about 2.3 eV, within the range, about 1.1 eV to about 3.0 eV, about 1.1 eV to about 2.9 eV, about 1.1 eV to about 2.8 eV, about 1.1 eV to about 2.7 eV, about 1.1 eV to about 2.6 eV, about 1.1 eV to about 2.5 eV, about 1.1 eV to about 2.4 eV, about 1.1 eV to about 2.3 eV, about 1.2 eV to about 3.0 eV, about 1.2 eV to about 2.9 eV, about 1.2 eV to about 2.8 eV, about 1.2 eV to about 2.7 eV, about 1.2 eV to about 2.6 eV, about 1.2 eV to about 2.5 eV, about 1.2 eV to about 2.4 eV, or about 1.2 eV to about 2.3 eV.

Herein, the LUMO energy level may be evaluated by obtaining an energy bandgap using a UV-Vis spectrometer (Shimadzu Corporation), and then calculating from the measured energy bandgap and the HOMO energy level that is already measured. The LUMO energy level of the organic buffer material and the LUMO energy level of the n-type semiconductor are expressed as absolute values. The difference between the LUMO energy level of the organic buffer material and the LUMO energy level of the n-type semiconductor may be the large value of the absolute value minus the small value of the absolute value.

For example, the energy bandgap of the organic buffer material may be greater than or equal to about 2.8 eV, within the range, greater than or equal to about 3.0 eV, greater than or equal to about 3.2 eV, about 2.8 eV to about 4.0 eV, about 3.0 eV to about 4.0 eV, or about 3.2 eV to about 4.0 eV.

For example, the organic buffer material may be a visible light non-absorbing material. The visible light non-absorbing material may be a material configured to not substantially absorb light in the visible region of about 400 nm to about 700 nm. Accordingly, the organic buffer layer may not affect the optical characteristics of the photoelectric conversion device 100.

In one example, the organic buffer material may be a low molecular weight compound, for example a depositable organic compound. For example, a $Ts_{10}$ temperature of the organic buffer material at which a weight loss of 10% relative to the initial weight occurs during thermogravimetric analysis at a pressure of less than or equal to about 1 Pa may be about 180° C. to about 450° C., about 190° C. to about 450° C., about 200° C. to about 450° C., about 210° C. to about 450° C., or about 220° C. to about 450° C. and a temperature ($Ts_{50}$) at which a weight loss of 50% relative to the initial weight occurs during thermogravimetric analysis at a pressure of less than or equal to about 1 Pa may be about 200° C. to about 500° C., about 220° C. to about 500° C., or about 250° C. to about 500° C. By having such high heat resistance, the organic buffer material may be stably repeatedly deposited and may maintain good performance without deterioration in subsequent high temperature processes.

The organic buffer material may be selected from compounds that meet the aforementioned electrical, optical, and thermal properties.

For example, the organic buffer material may include at least three carbazole moieties. For example, the organic buffer material may include three carbazole moieties.

For example, the organic buffer material may be represented by Chemical Formula 1.

[Chemical Formula 1]

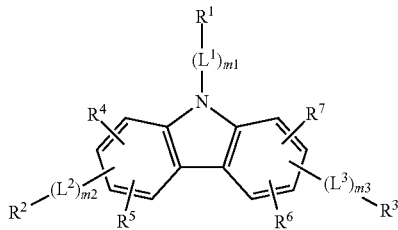

In Chemical Formula 1, $L^1$ to $L^3$ may independently be a substituted or unsubstituted C6 to C20 arylene group, $R^1$ to $R^7$ may independently be hydrogen, a substituted or unsubstituted C1 to C30 alkyl group, a substituted or unsubstituted C1 to C30 alkoxy group, a substituted or unsubstituted C6 to C20 aryl group, a substituted or unsubstituted C3 to C20 heteroaryl group, a substituted or unsubstituted carbazolyl group, a halogen, a cyano group, or a combination thereof, at least two of $R^1$ to $R^3$ may be a substituted or unsubstituted carbazolyl group, and $m^1$ to $m^3$ may independently be 0 or 1.

For example, $L^1$ to $L^3$ may independently be a substituted or unsubstituted phenylene group, a substituted or unsubstituted biphenylene group, a substituted or unsubstituted naphthylene group, or a substituted or unsubstituted terphenylene group.

For example, $L^1$ to $L^3$ may independently be a substituted or unsubstituted phenylene group, a substituted or unsubstituted biphenylene group, or a substituted or unsubstituted naphthylene group.

For example, $L^1$ to $L^3$ may independently be a substituted or unsubstituted phenylene group or a substituted or unsubstituted biphenylene group.

For example, $m^1$ to $m^3$ may independently be 0.

For example, one of $m^1$ to $m^3$ may be 1 and the remaining two may be 0.

For example, two of $m^1$ to $m^3$ may be 1 and the remaining one may be 0.

For example, $m^1$ to $m^3$ may be 1.

For example, two of $R^1$ to $R^3$ may be a substituted or unsubstituted carbazolyl group.

For example, two of $R^1$ to $R^3$ may be a substituted or unsubstituted carbazolyl group and the remaining one of $R^1$ to $R^3$ may be hydrogen, a substituted or unsubstituted phenyl group, a substituted or unsubstituted biphenyl group, or a substituted or unsubstituted naphthyl group.

For example, two of $R^1$ to $R^3$ may be a substituted or unsubstituted carbazolyl group and the remaining one of $R^1$ to $R^3$ may be a substituted or unsubstituted phenyl group.

For example, $R^1$ and $R^2$ or $R^3$ may independently be a substituted or unsubstituted carbazolyl group.

For example, $R^1$ and $R^2$ or $R^3$ may independently be a substituted or unsubstituted carbazolyl group and the remaining one of $R^2$ and $R^3$ may be hydrogen, a substituted or unsubstituted phenyl group, a substituted or unsubstituted biphenyl group, or a substituted or unsubstituted naphthyl group.

For example, $R^1$ and $R^2$ or $R^3$ may independently be a substituted or unsubstituted carbazolyl group and the remaining one of $R^2$ and $R^3$ may be hydrogen or a substituted or unsubstituted phenyl group.

For example, $R^2$ and $R^3$ may independently be a substituted or unsubstituted carbazolyl group.

For example, $R^2$ and $R^3$ may independently be a substituted or unsubstituted carbazolyl group and $R^1$ may be hydrogen, a substituted or unsubstituted phenyl group, a substituted or unsubstituted biphenyl group, or a substituted or unsubstituted naphthyl group.

For example, $R^2$ and $R^3$ may independently be a substituted or unsubstituted carbazolyl group and $R^1$ may be a substituted or unsubstituted phenyl group.

For example, the organic buffer material represented by Formula 1 may be represented by one of Chemical Formulae 1A to 1C.

[Chemical Formula 1A]

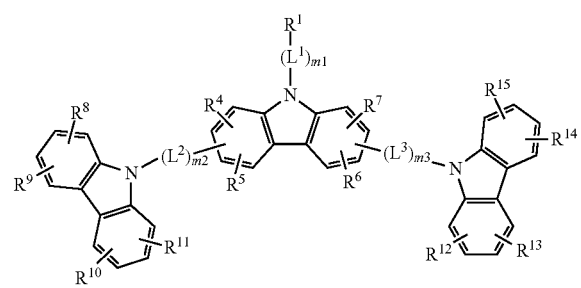

[Chemical Formula 1B]

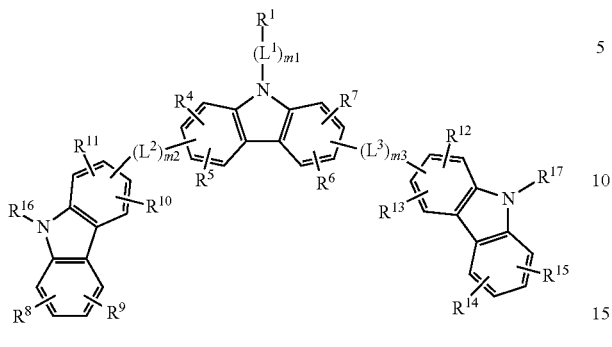

[Chemical Formula 1C]

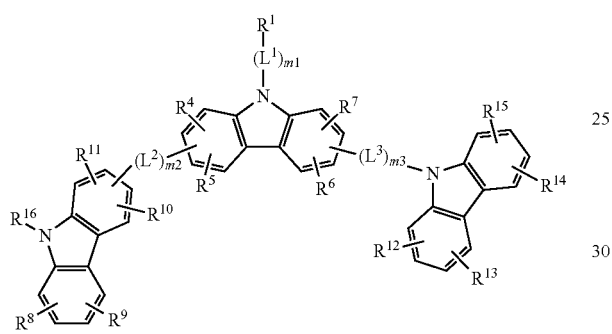

[Chemical Formula 1D]

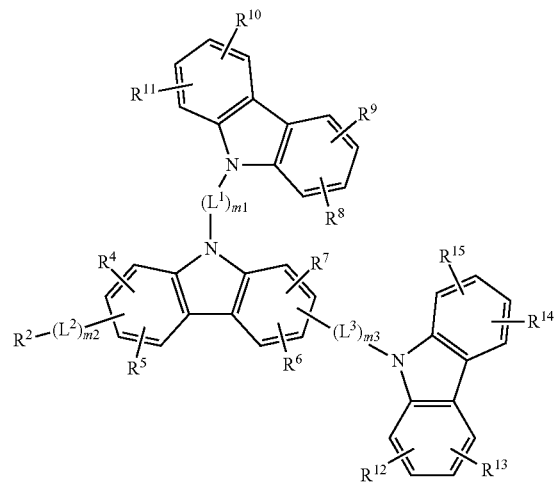

[Chemical Formula 1E]

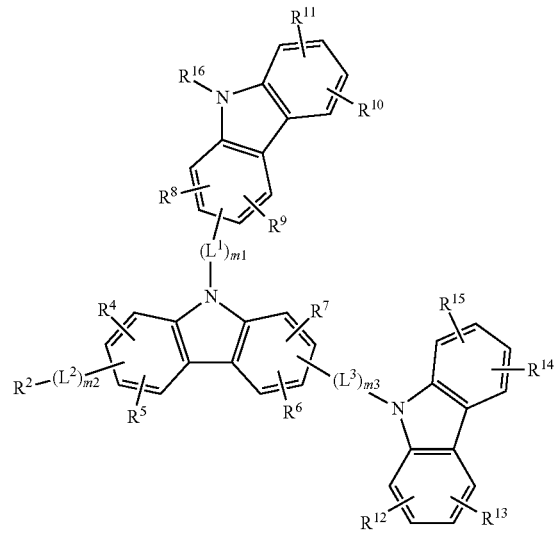

[Chemical Formula 1F]

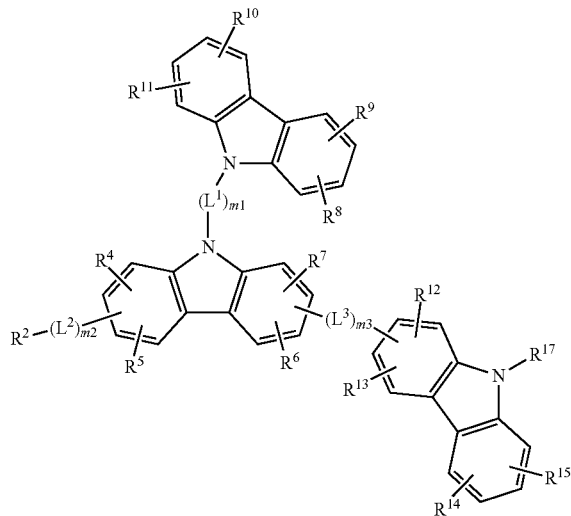

In Chemical Formulae 1A to 1C, $L^1$ to $L^3$, $R^1$, $R^4$ to $R^{17}$ and $m^1$ to $m^3$ are the same as described above.

For example, $R^1$ and $R^4$ to $R^{17}$ may independently be hydrogen, a substituted or unsubstituted phenyl group, a substituted or unsubstituted biphenyl group, or a substituted or unsubstituted naphthyl group.

For example, $R^1$ and $R^4$ to $R^{17}$ may independently be hydrogen or a substituted or unsubstituted phenyl group.

For example, three of $R^1$, $R^4$ to $R^{17}$ and $L^1$ to $L^3$ may be a substituted or unsubstituted phenyl group or a substituted or unsubstituted phenylene group.

For example, three of $R^1$ and $R^4$ to $R^{17}$ may be a substituted or unsubstituted phenyl group, the remaining of $R^1$ and $R^4$ to $R^{17}$ may be hydrogen, and $L^1$ to $L^3$ may independently be a substituted or unsubstituted phenylene group, and $m^1$ to $m^3$ may independently be 0.

For example, two of $R^1$ and $R^4$ to $R^{17}$ may be a substituted or unsubstituted phenyl group, the remaining one of $R^1$ and $R^4$ to $R^{17}$ may be hydrogen, $L^1$ to $L^3$ may independently be substituted or unsubstituted phenylene groups, and one of $m^1$ to $m^3$ may be 1 and the remaining two may be 0.

For example, one of $R^1$ and $R^4$ to $R^{17}$ may be a substituted or unsubstituted phenyl group, the remaining one of $R^1$ and $R^4$ to $R^{17}$ may be hydrogen, $L^1$ to $L^3$ may be independently a substituted or unsubstituted phenylene group, and two of $m^1$ to $m^3$ may be 1 and the remaining one may be 0.

For example, the organic buffer material represented by Chemical Formula 1 may be represented by one Chemical Formula 1D to 1G.

[Chemical Formula 1G]

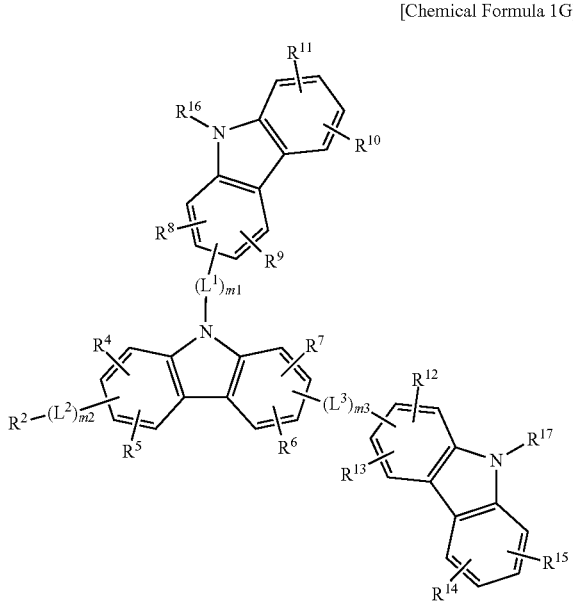

[Chemical Formula 1D-1]

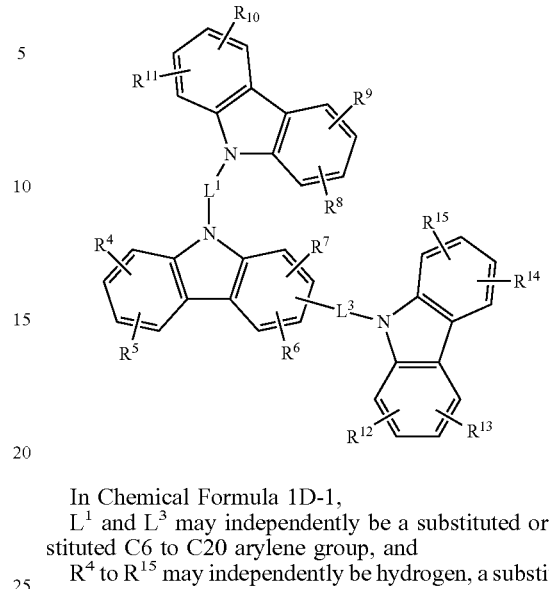

In Chemical Formulae 1D to 1G, $L^1$ to $L^3$, $R^2$, $R^4$ to $R^{17}$ and $m^1$ to $m^3$ are the same as described above.

For example, $R^2$ and $R^4$ to $R^{17}$ may independently be hydrogen, a substituted or unsubstituted phenyl group, a substituted or unsubstituted biphenyl group, or a substituted or unsubstituted naphthyl group.

For example, $R^2$ and $R^4$ to $R^{17}$ may independently be hydrogen or a substituted or unsubstituted phenyl group.

For example, three of $R^2$, $R^4$ to $R^{17}$, and $L^1$ to $L^3$ may be a substituted or unsubstituted phenyl group or a substituted or unsubstituted phenylene group.

For example, three of $R^2$ and $R^4$ to $R^{17}$ may be a substituted or unsubstituted phenyl group, the remaining one of $R^2$ and $R^4$ to $R^{17}$ may be hydrogen, $L^1$ to $L^3$ may independently be a substituted or unsubstituted phenylene group, and each of $m^1$ to $m^3$ may be 0.

For example, two of $R^2$ and $R^4$ to $R^{17}$ may be a substituted or unsubstituted phenyl group, the remaining one of $R^2$ and $R^4$ to $R^{17}$ may be hydrogen, $L^1$ to $L^3$ may independently be a substituted or unsubstituted phenylene group, and one of $m^1$ to $m^3$ may be 1 and the remaining two may be 0.

For example, one of $R^2$ and $R^4$ to $R^{17}$ may be a substituted or unsubstituted phenyl group, the remaining one of $R^2$ and $R^4$ to $R^{17}$ may be hydrogen, $L^1$ to $L^3$ may independently be a substituted or unsubstituted phenylene group, and two of $m^1$ to $m^3$ may be 1 and the remaining one of $m_1$ to $m_3$ may be 0.

For example, the organic buffer material represented by Chemical Formula 1D may be represented by Chemical Formula 1D-1.

In Chemical Formula 1D-1,
$L^1$ and $L^3$ may independently be a substituted or unsubstituted C6 to C20 arylene group, and
$R^4$ to $R^{15}$ may independently be hydrogen, a substituted or unsubstituted C1 to C30 alkyl group, a substituted or unsubstituted C1 to C30 alkoxy group, a substituted or unsubstituted C6 to C20 aryl group, a substituted or unsubstituted C3 to C20 heteroaryl group, a substituted or unsubstituted carbazolyl group, a halogen, a cyano group, or a combination thereof.

For example, $R^4$ to $R^{15}$ may independently be hydrogen, a substituted or unsubstituted phenyl group, a substituted or unsubstituted biphenyl group, or a substituted or unsubstituted naphthyl group.

For example, $L^1$ to $L^3$ may independently be a substituted or unsubstituted phenylene group, a substituted or unsubstituted biphenylene group, or a substituted or unsubstituted naphthylene group.

For example, the organic buffer material represented by Chemical Formula 1D-1 may include three phenyl moieties.

In one example, the organic buffer material may include three carbazole moieties and three phenyl moieties. Herein, the phenyl moiety includes a phenyl group and a phenylene group.

For example, the organic buffer material may be represented by Chemical Formula 1-1.

[Chemical Formula 1-1]

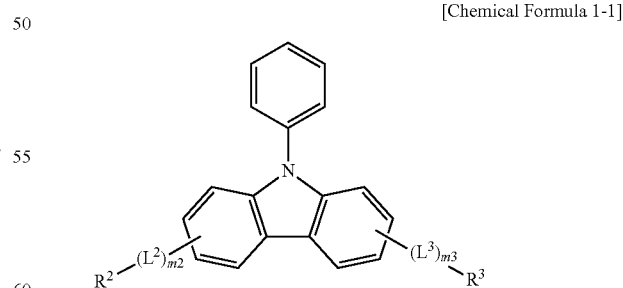

In Chemical Formula 1-1,
each of $L^2$ and $L^3$ may be a phenyl group,
$m_2$ and $m_3$ may be 0 or 1, and
$R^2$ and $R^3$ may independently be a carbazolyl group or a phenyl-substituted carbazolyl group and for example may be independently one of groups listed in Group 1.

[Group 1]

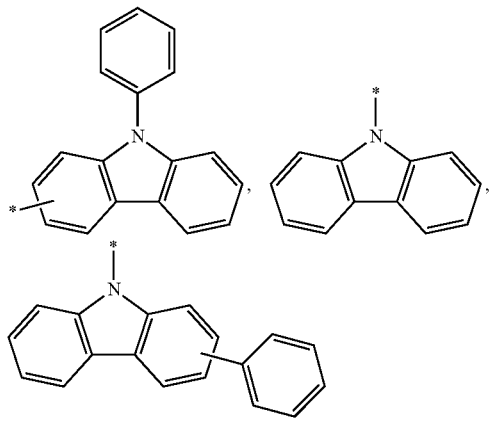

In Group 1, * is a linking point.

The number of phenyl moieties included in Chemical Formula 1-1 may be three.

For example, the organic buffer material represented by Chemical Formula 1 may be represented by Chemical Formulae 1-2 or 1-3.

[Chemical Formula 1-2]

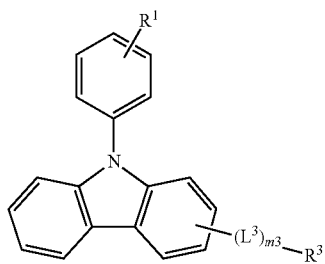

[Chemical Formula 1-3]

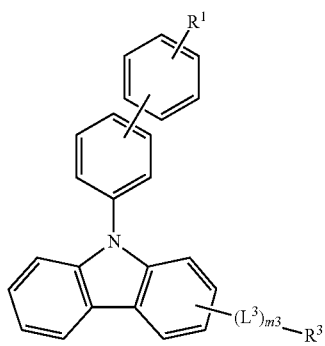

In Chemical Formula 1-2 or 1-3,
$L^3$ may be a phenyl group,
$m^3$ may be 0 or 1, and
$R^1$ and $R^3$ may independently be a carbazolyl group or a phenyl-substituted carbazolyl group, for example $R^1$ and $R^3$ may be independently one of the groups listed in Group 1.

The number of phenyl moieties included in Formula 1-2 or 1-3 may be three.

For example, the organic buffer material represented by Chemical Formula 1 may be represented by Chemical Formula 1-4.

[Chemical Formula 1-4]

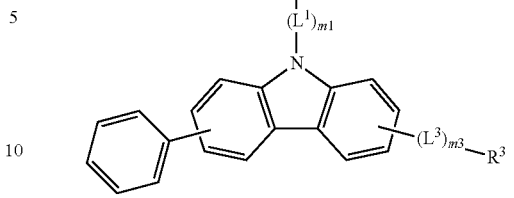

In Chemical Formula 1-4,
$L^1$ and $L^3$ may independently be a phenyl group,
$m^1$ and $m^3$ may independently be 0 or 1, and
$R^1$ and $R^3$ may independently be a carbazolyl group or a phenyl-substituted carbazolyl group, for example and may be independently one of the groups listed in Group 1.

The number of phenyl moieties included in Chemical Formula 1-4 may be three.

For example, the organic buffer material may be represented by Chemical Formula 1-2-1 or 1-3-1.

[Chemical Formula 1-2-1]

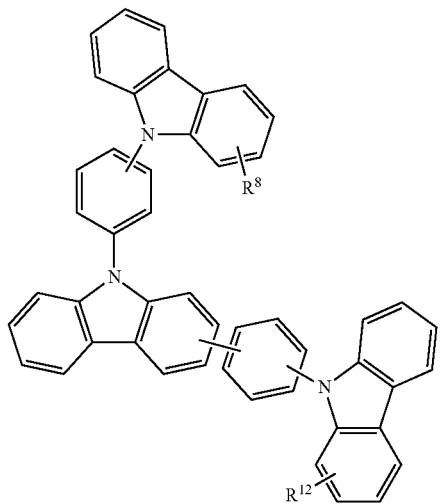

[Chemical Formula 1-3-1]

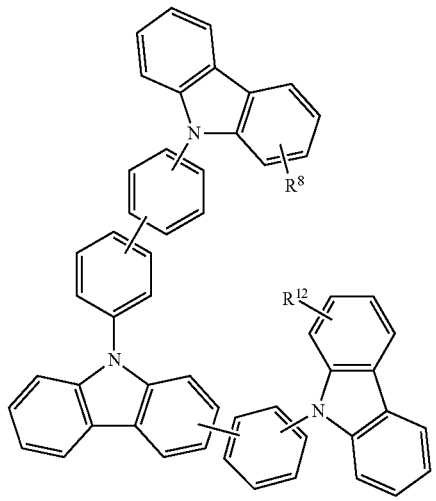

In Chemical Formula 1-2-1 or 1-3-1,
$R^8$ and $R^{12}$ may independently be hydrogen or a phenyl group.
The molecular weight of the organic buffer material may be about 600 g/mol to about 900 g/mol and within the range, may be about 700 g/mol to 800 g/mol.
The organic buffer material may be, for example, one or two or more selected from the compounds listed in Group 2, but is not limited thereto.
[Group 2]
1
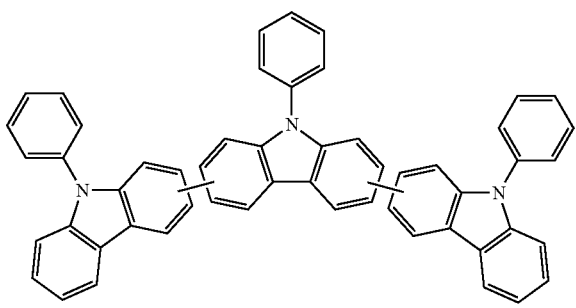
2
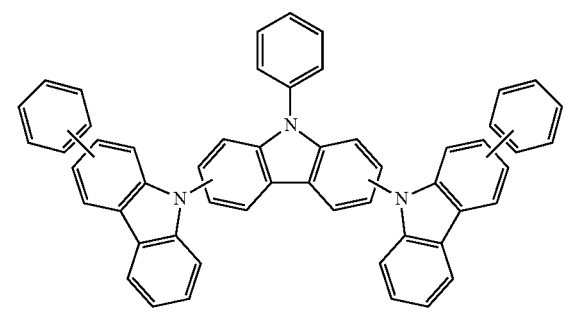
3
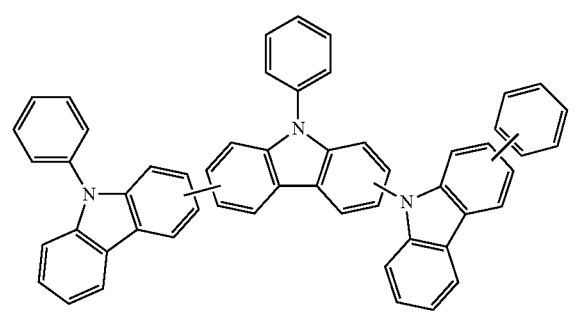
4
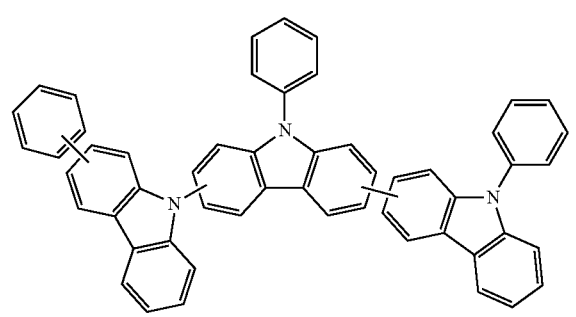
5
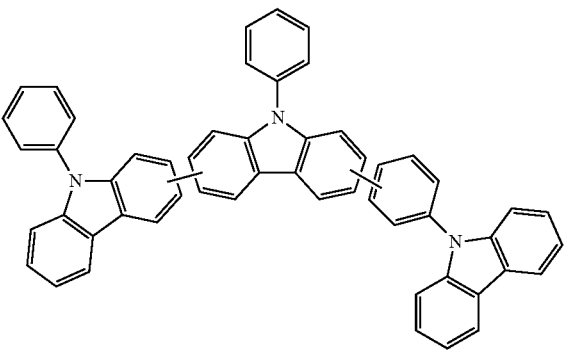
6
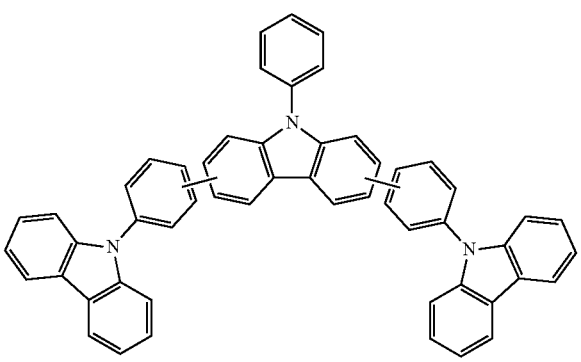
7
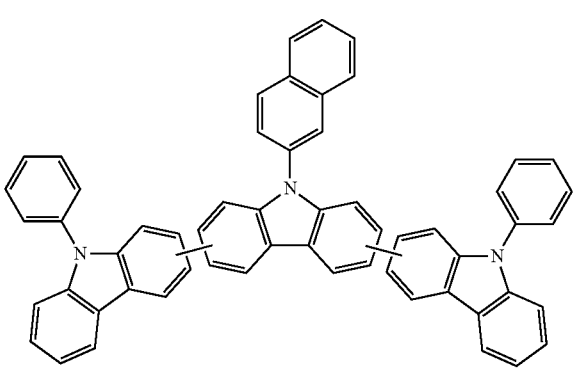
8
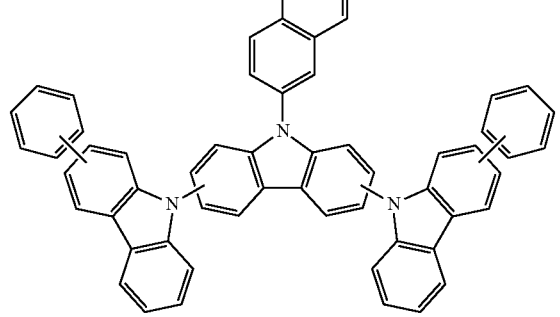

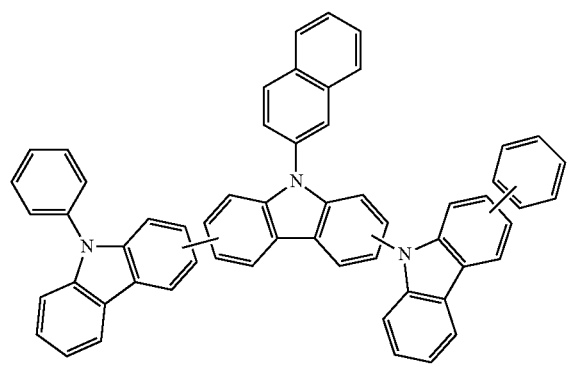
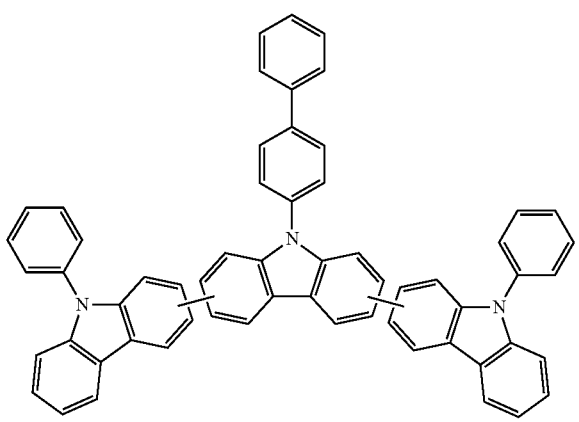
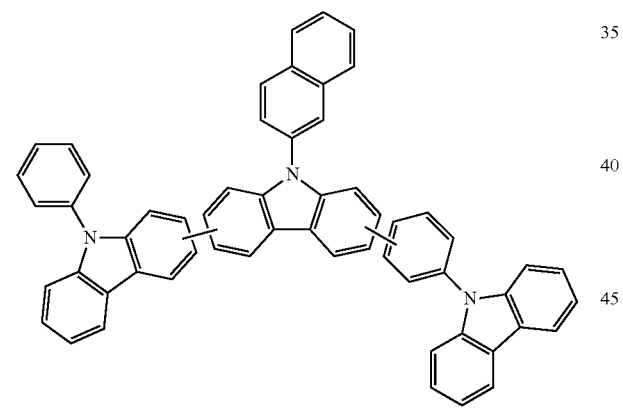
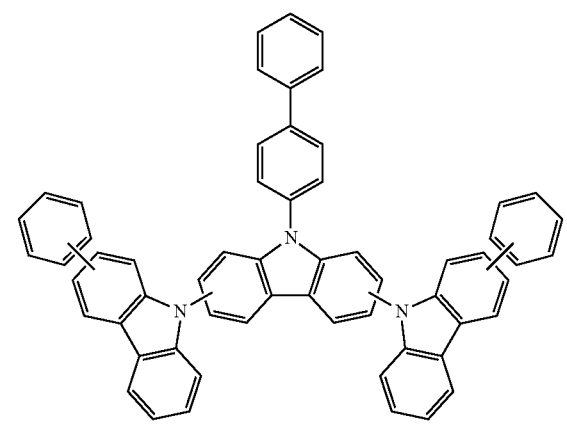
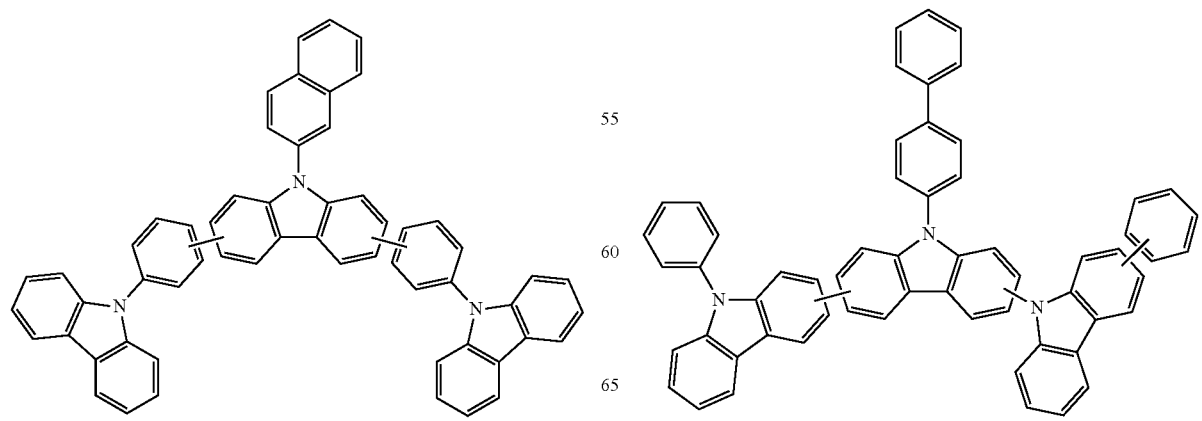

16
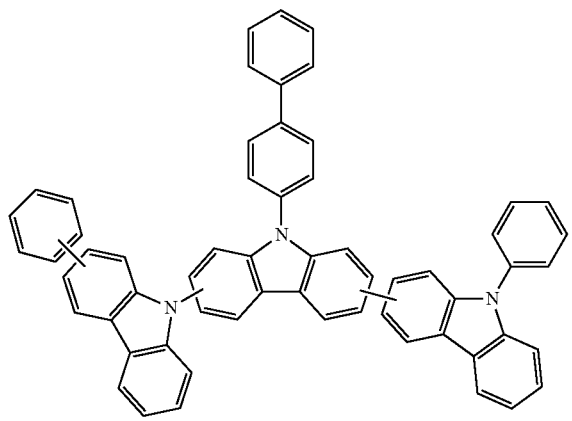
17
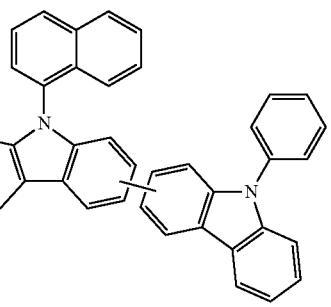
18
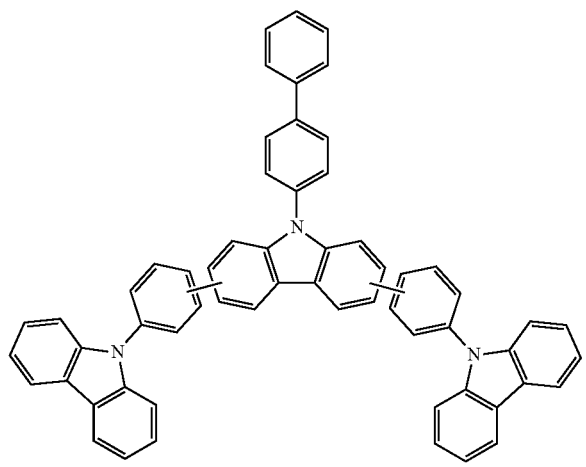
19
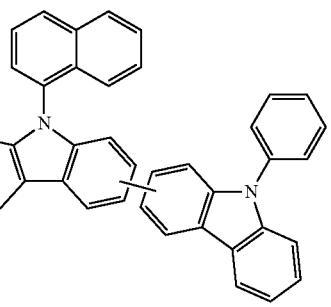
20
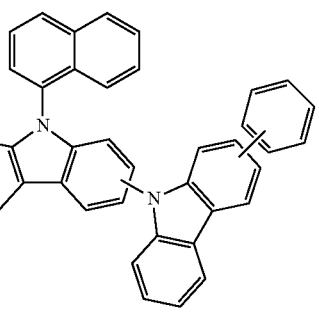
21
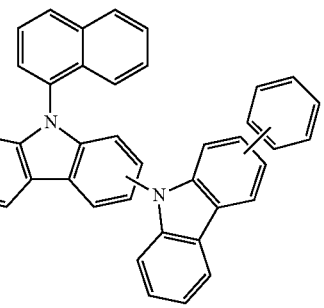
22
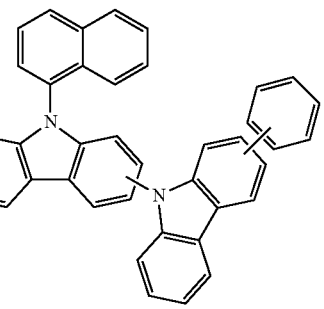

22
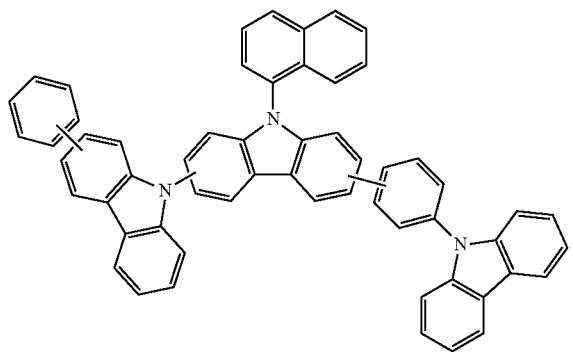
23
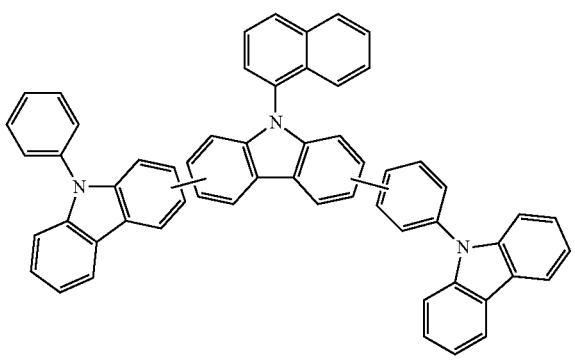
24
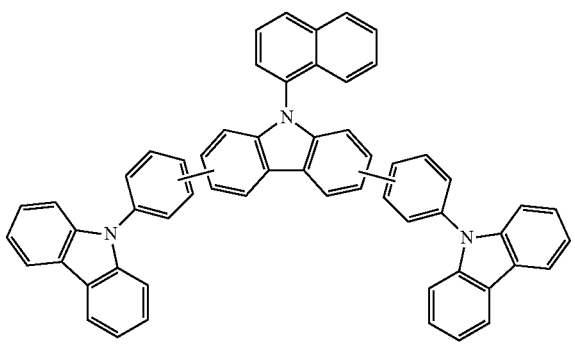
25
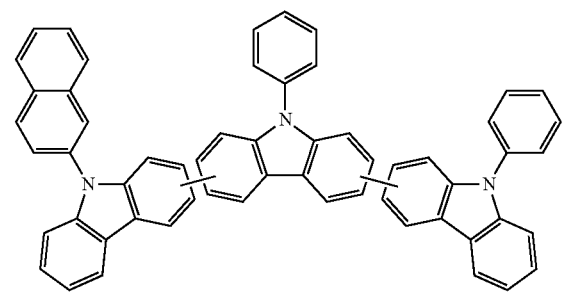
26
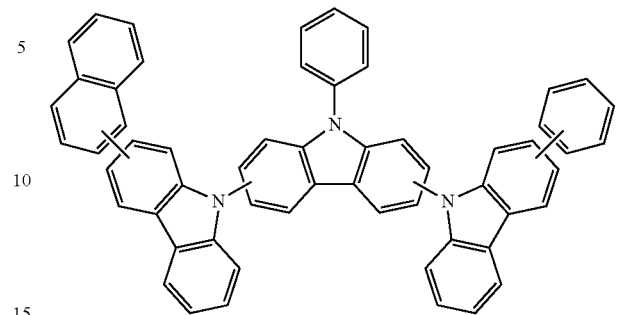
27
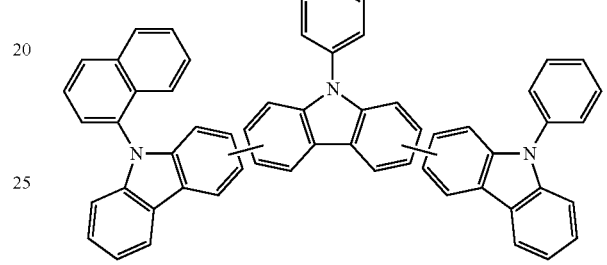
28
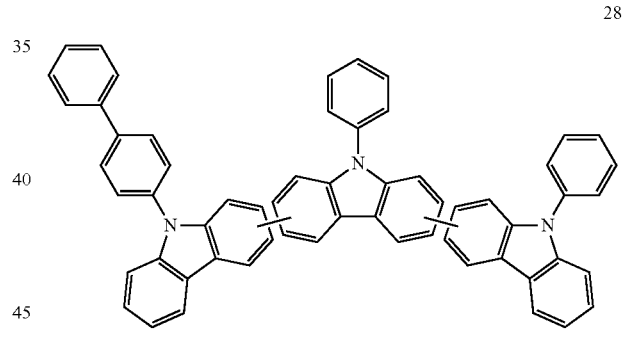
29
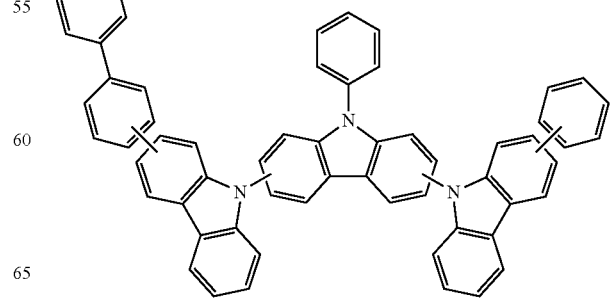

30
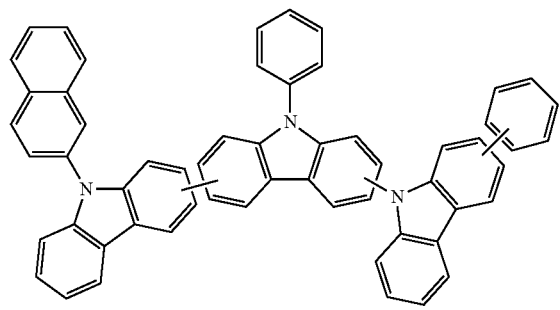
31
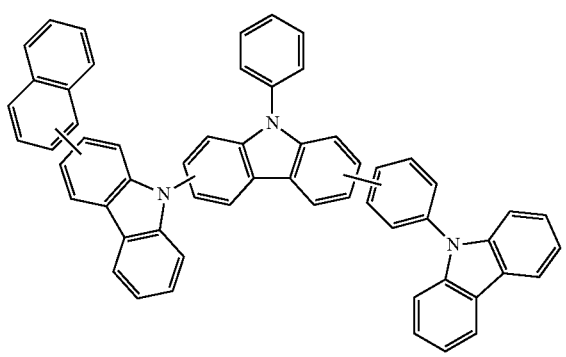
32
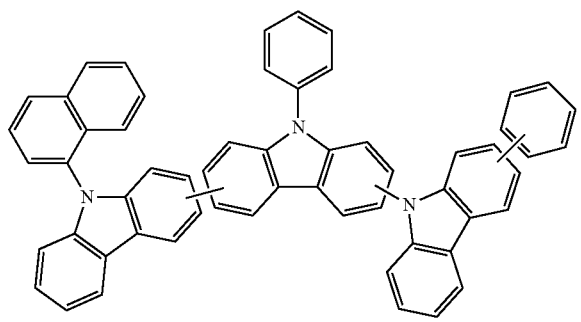
33
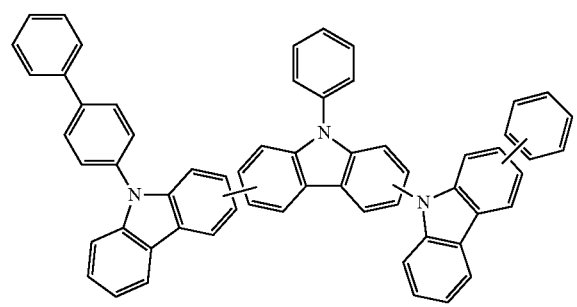
34
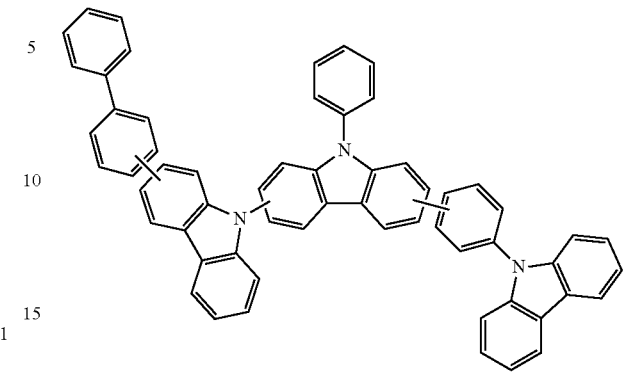
35
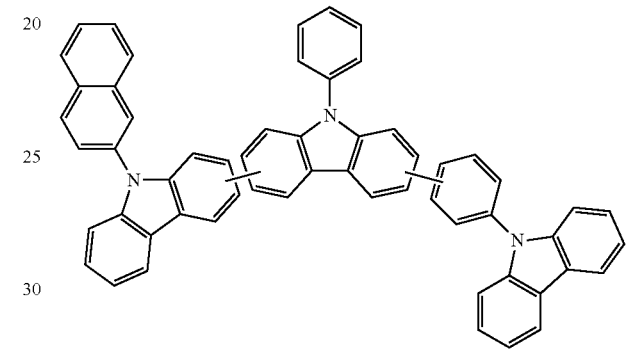
36
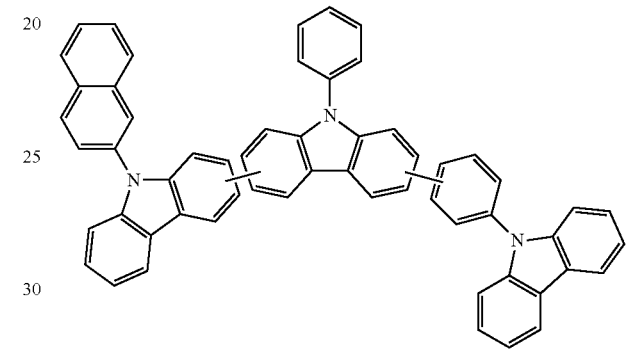
37
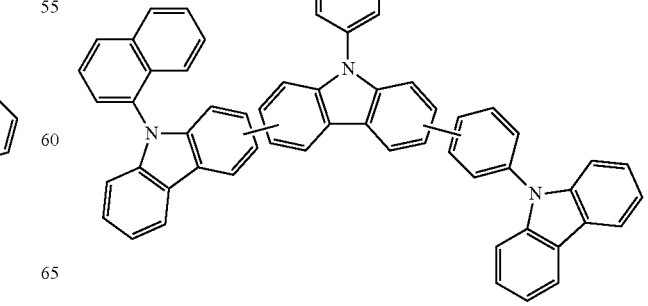

38
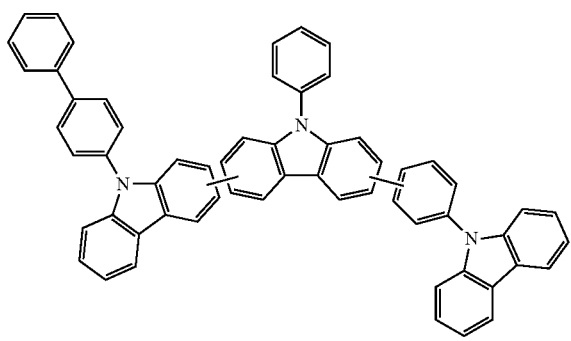
39
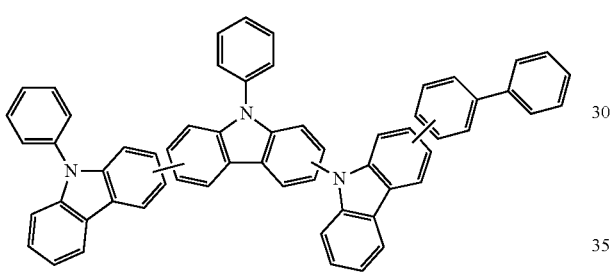
40
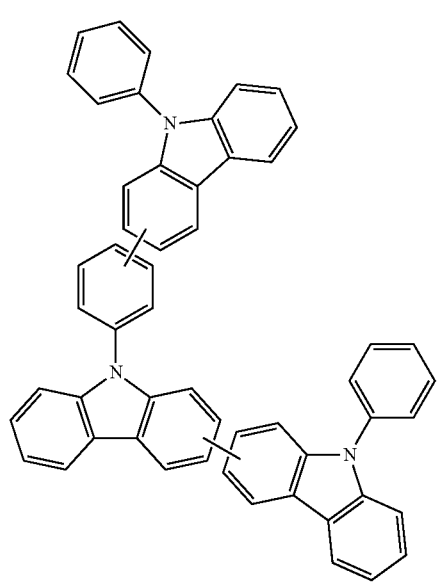
41
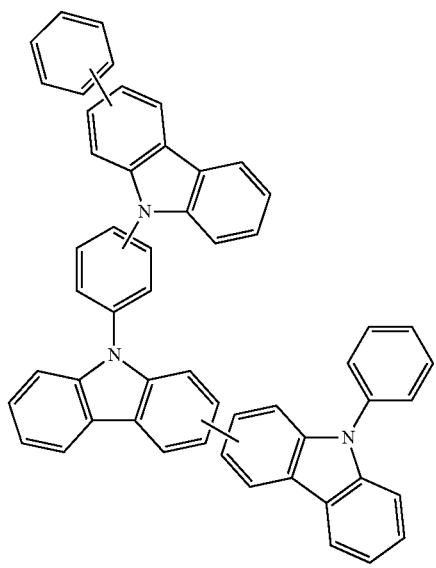
42
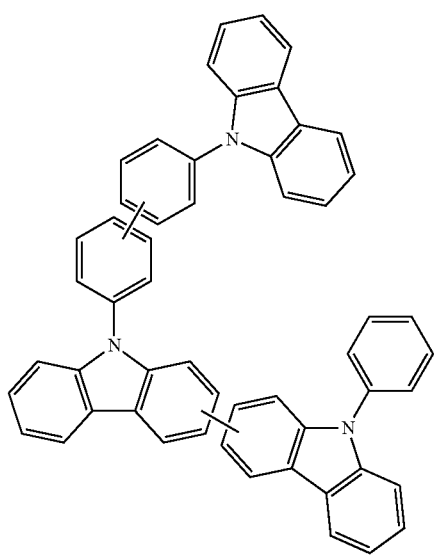

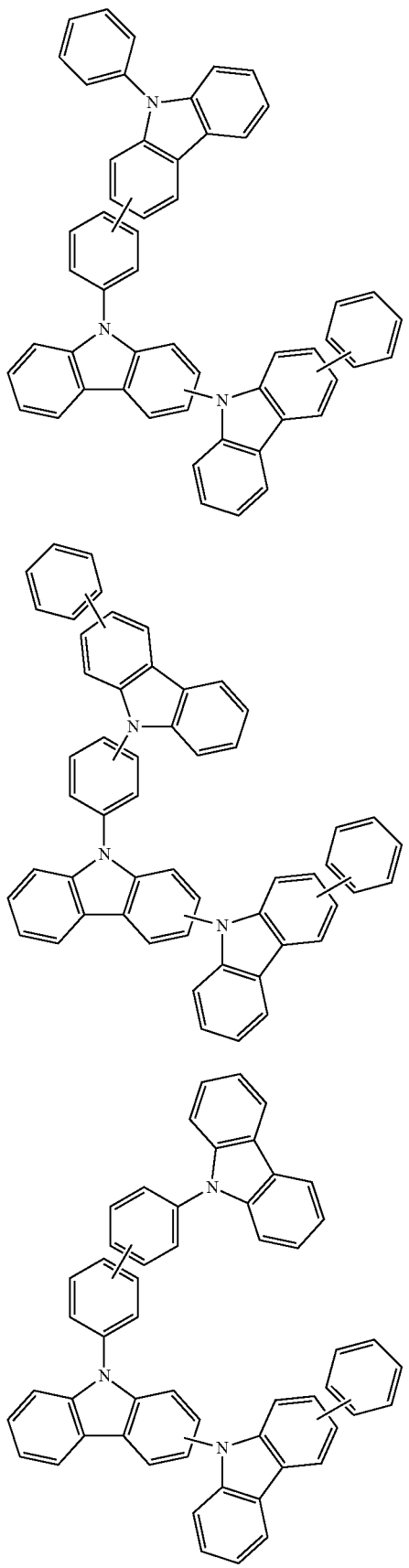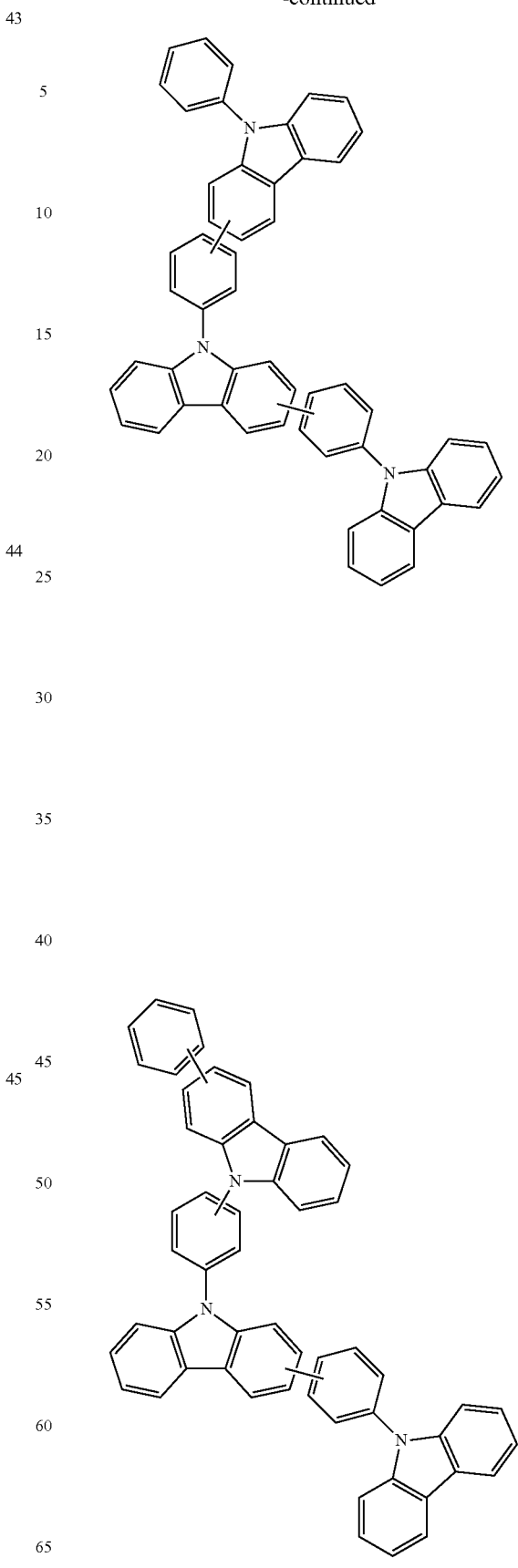

48
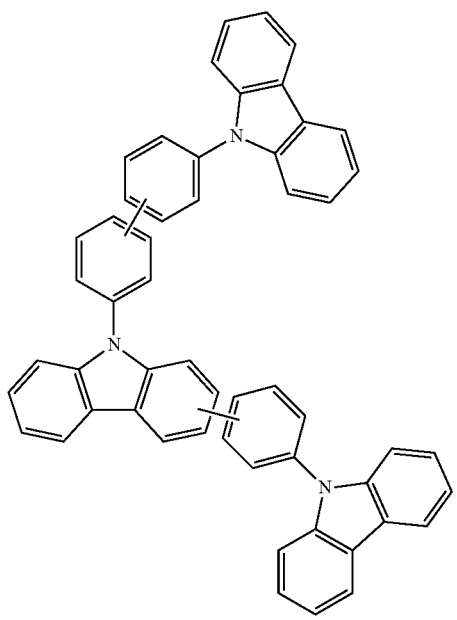
49
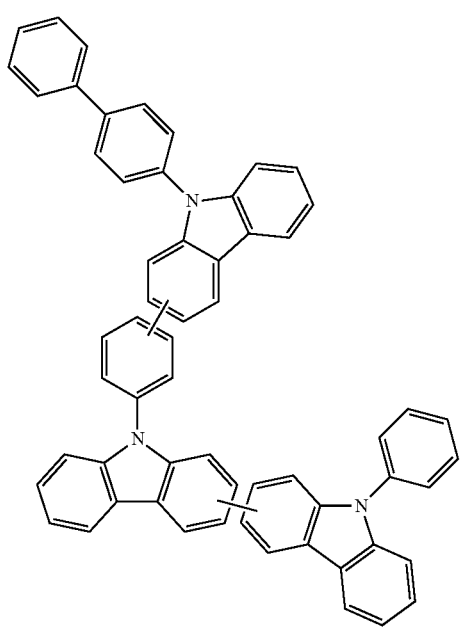
50
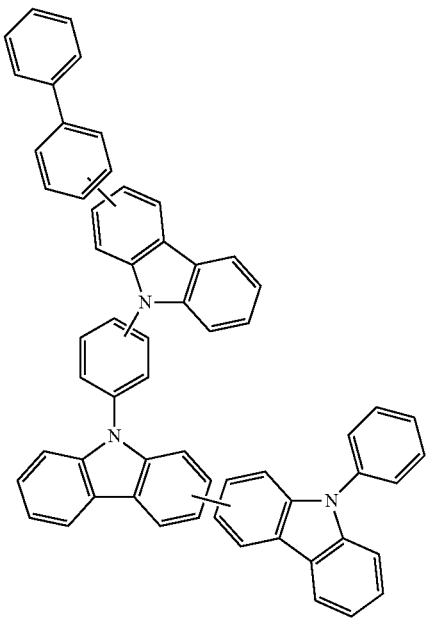
51
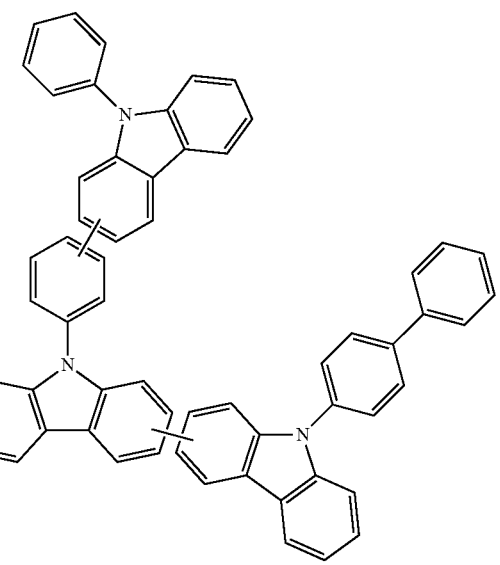

52
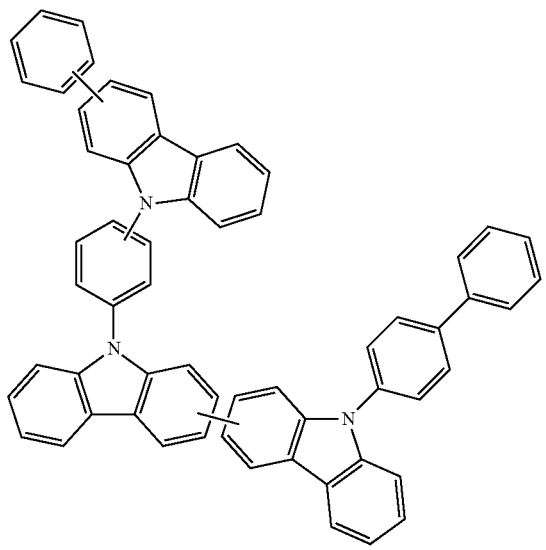
53
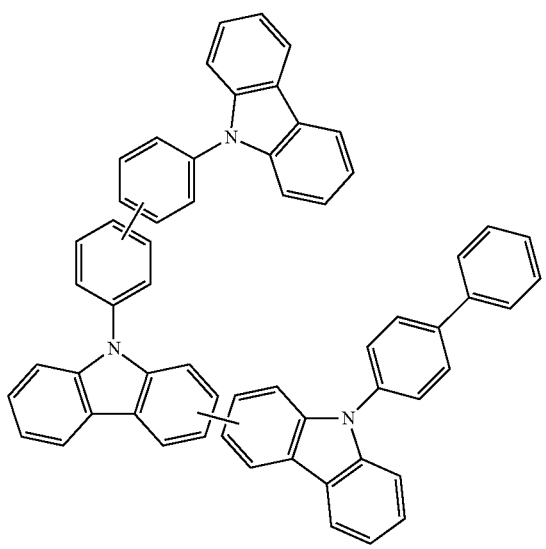
54
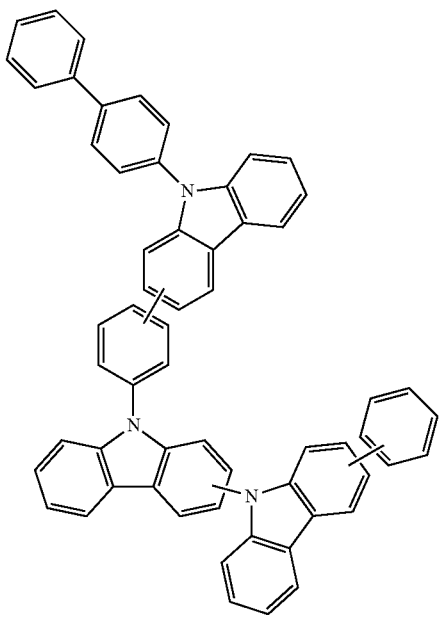
55
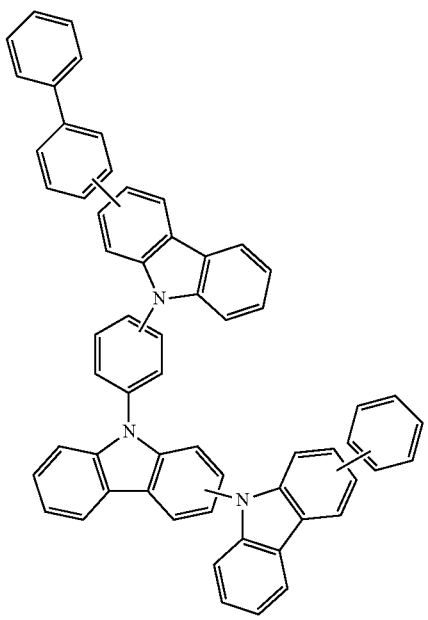

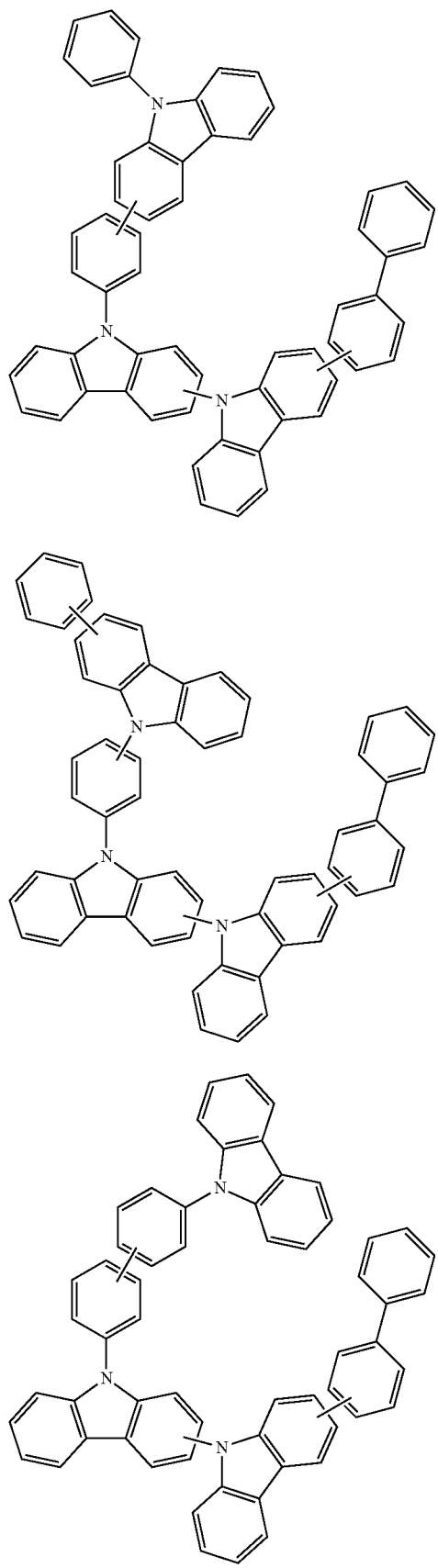

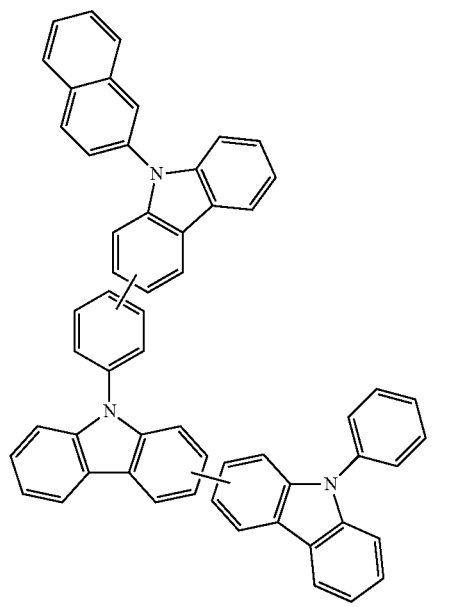
61
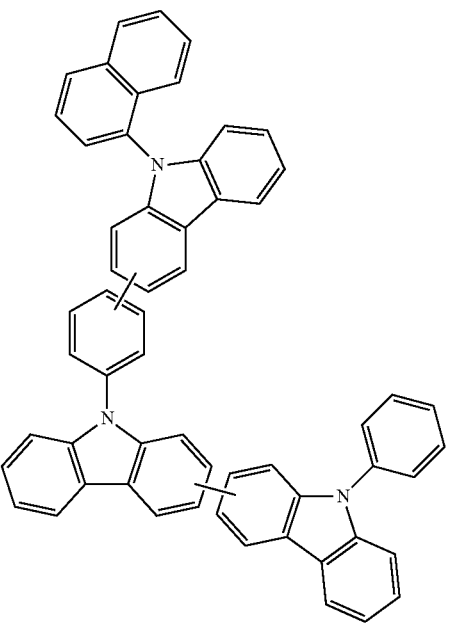
63
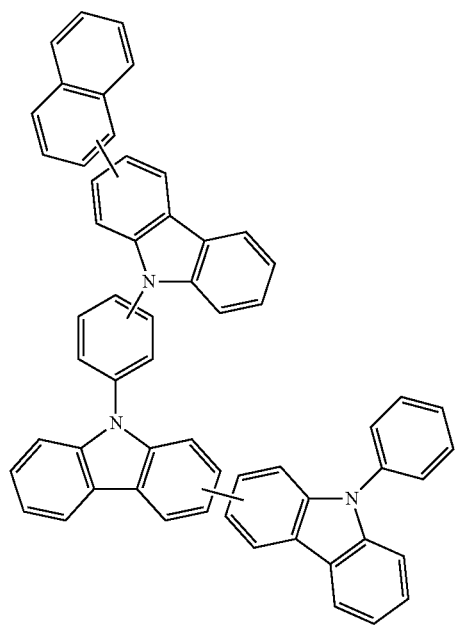
62
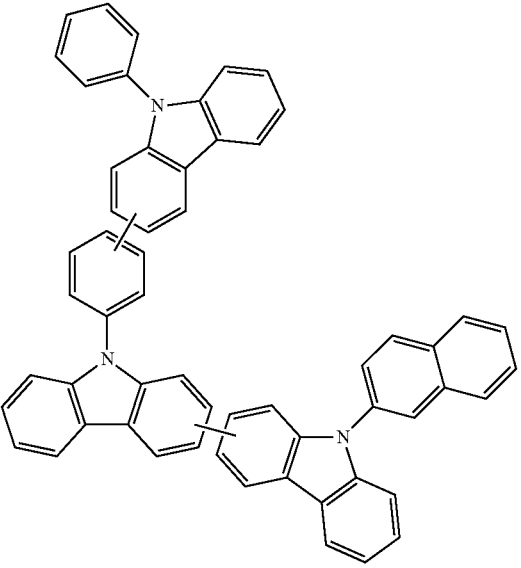
64

65
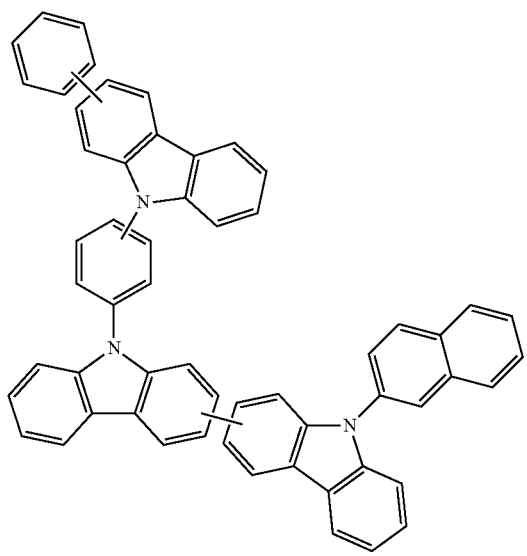
67
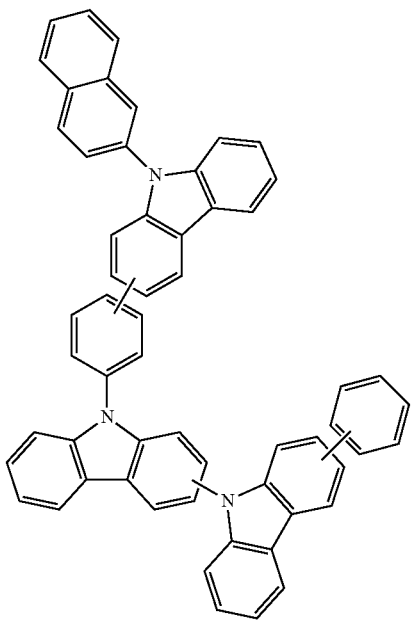
66
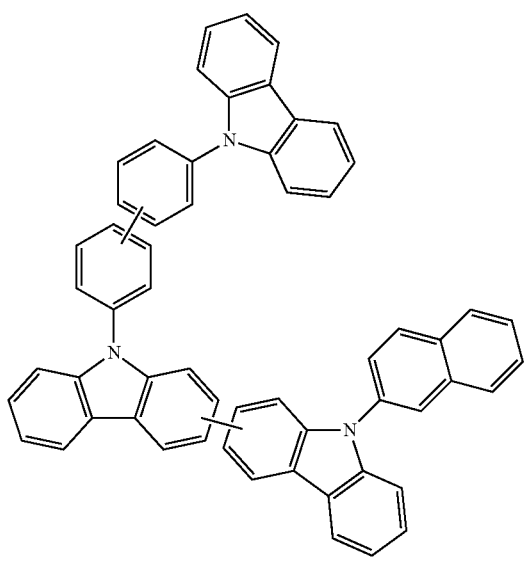
68
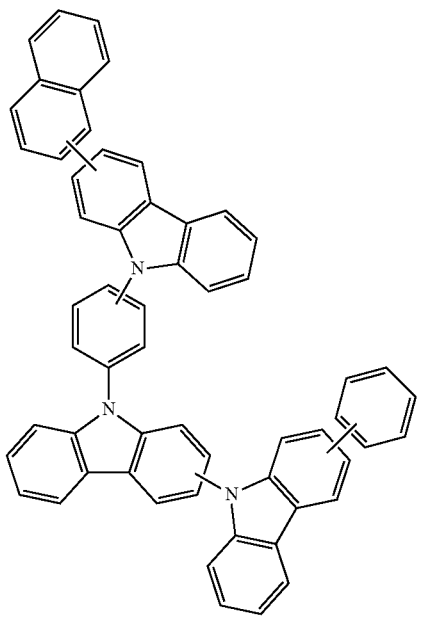

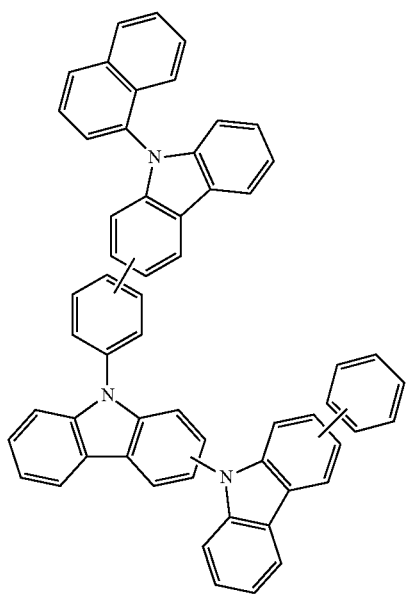
69
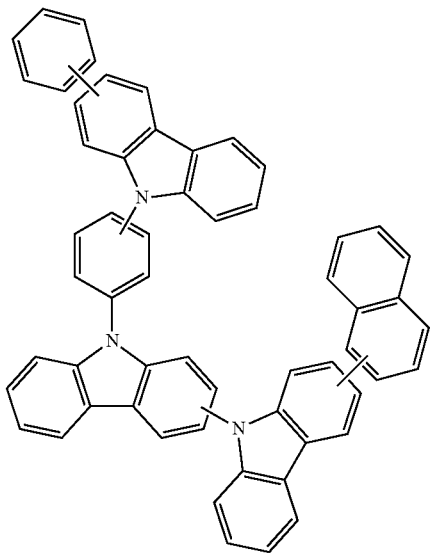
71
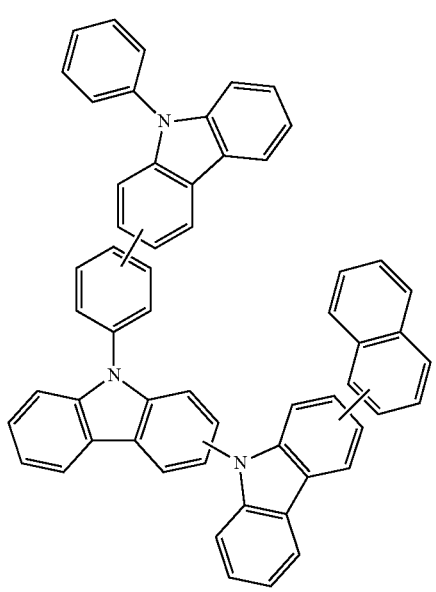
70
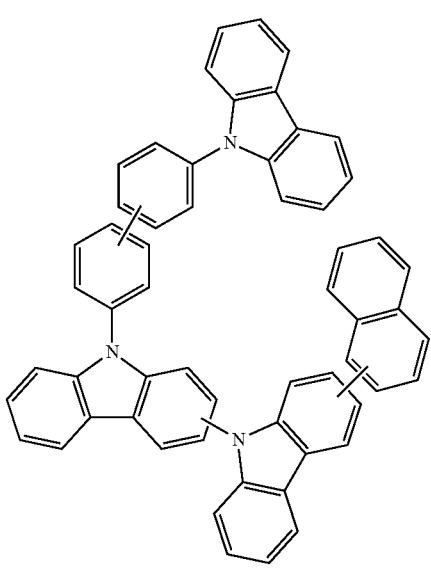
72

73
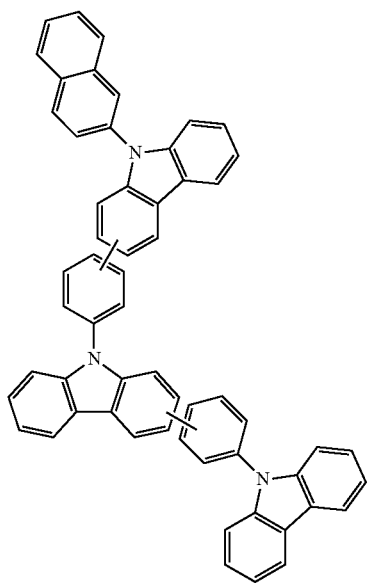
75
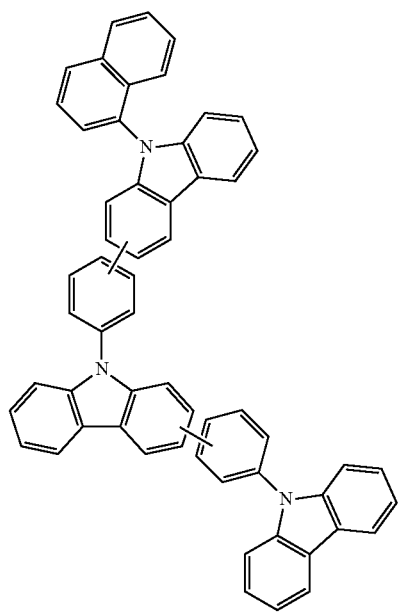
74
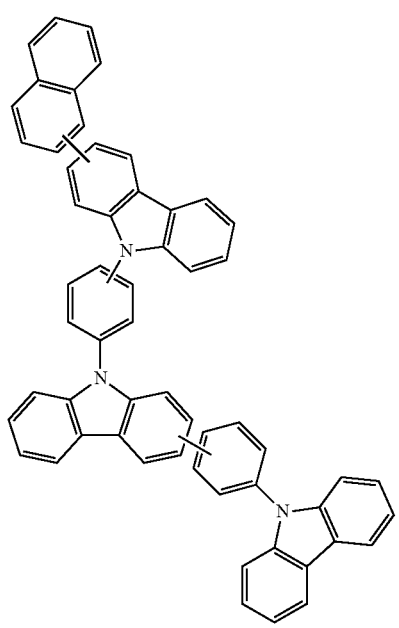
76
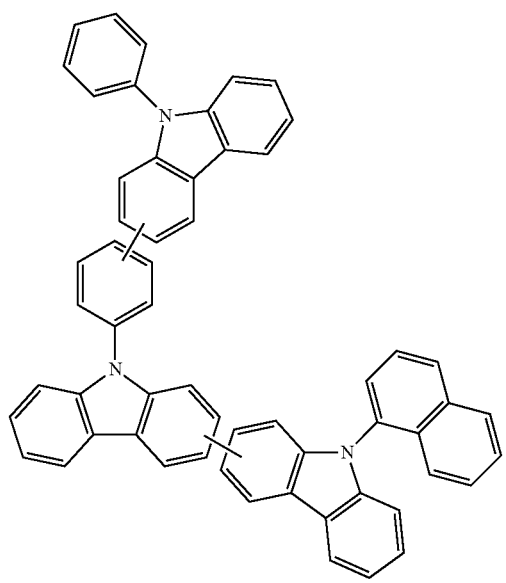

77
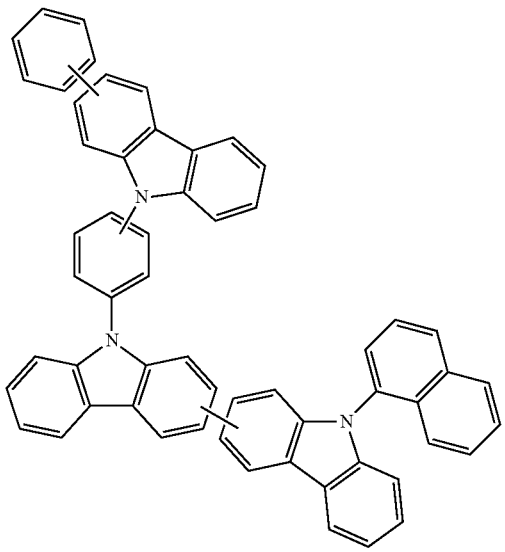
78
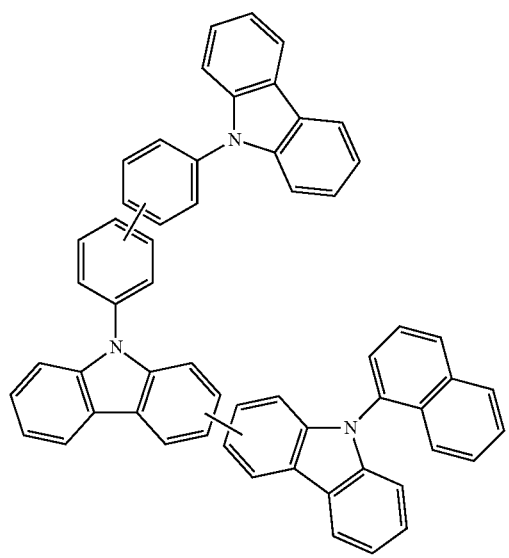
80
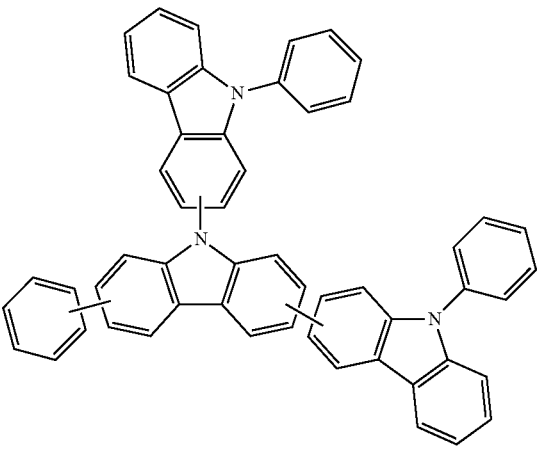
81
82
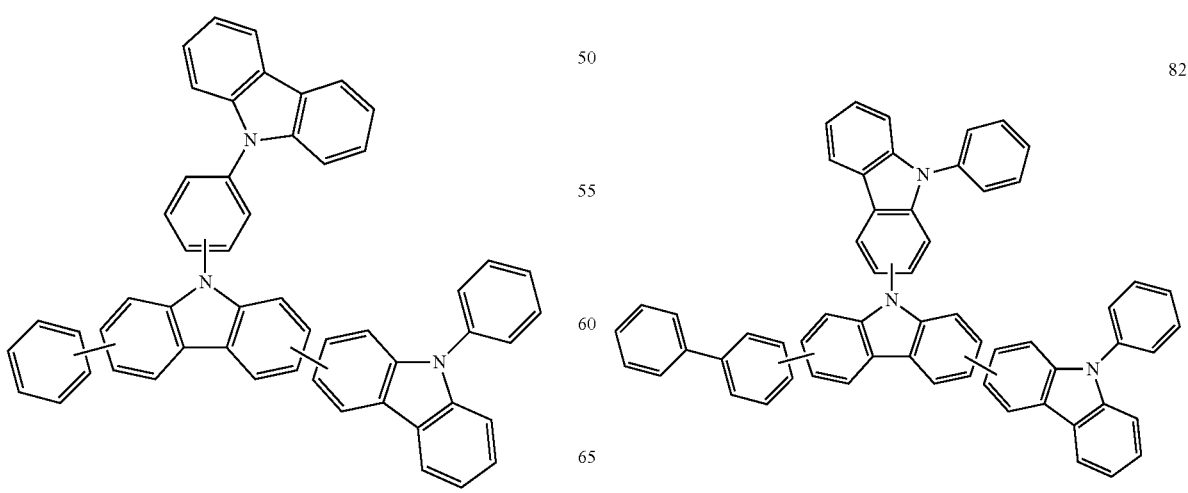

83
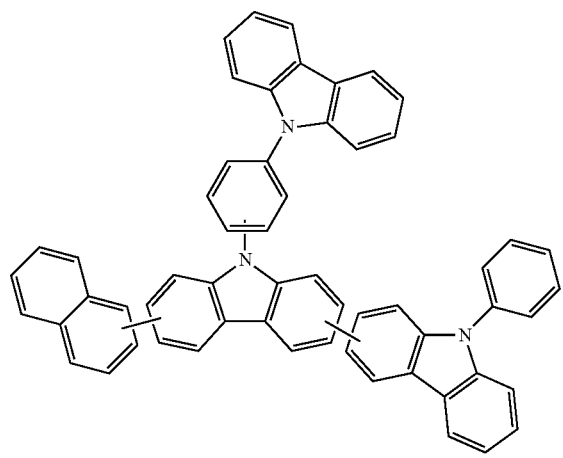
84
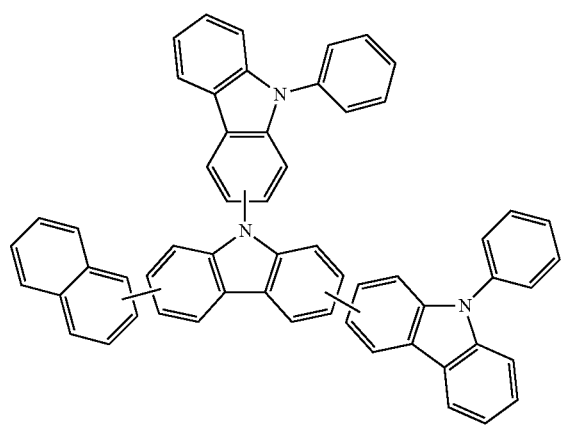
85
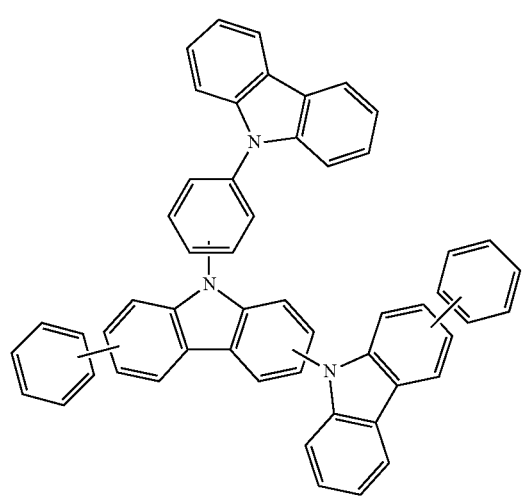
86
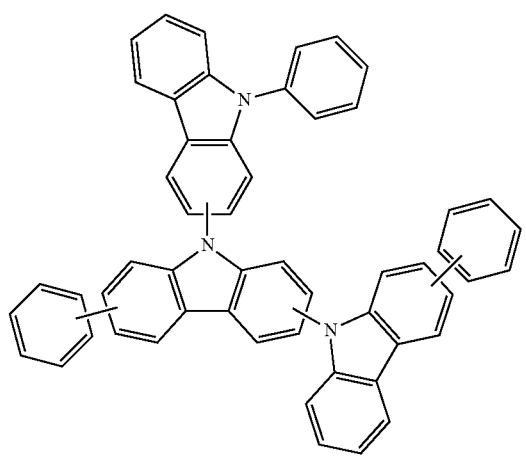
87
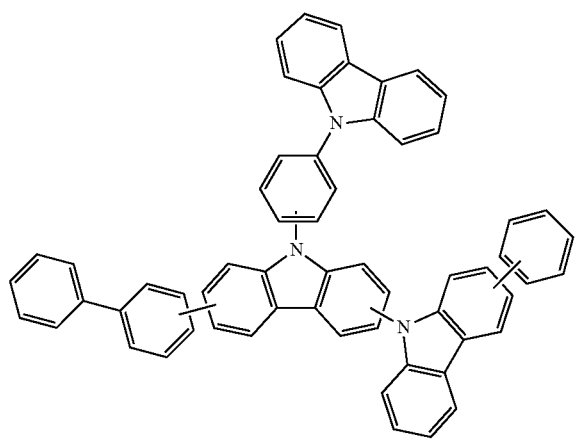
88
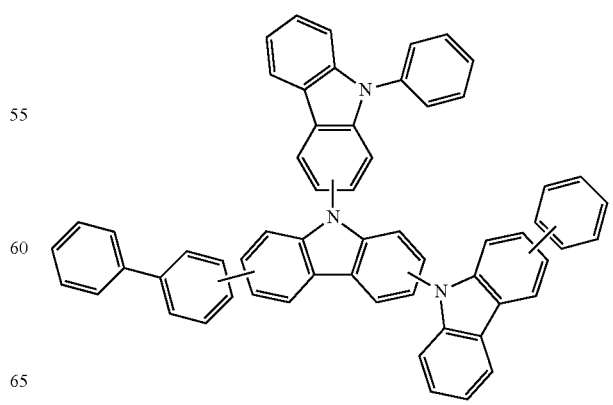

89
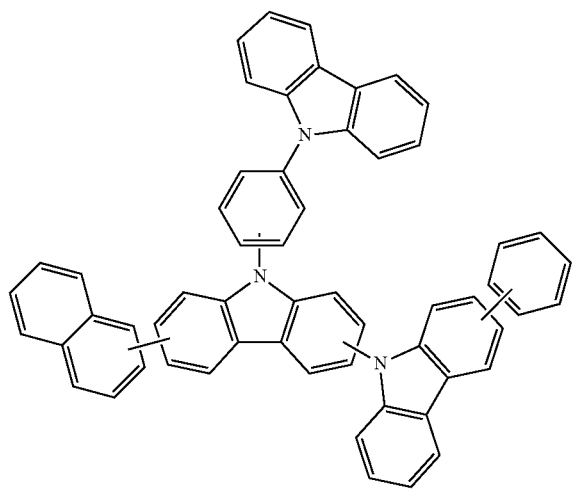
90
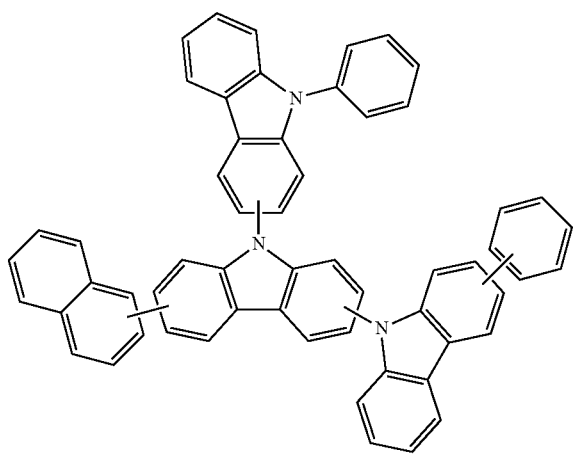
91
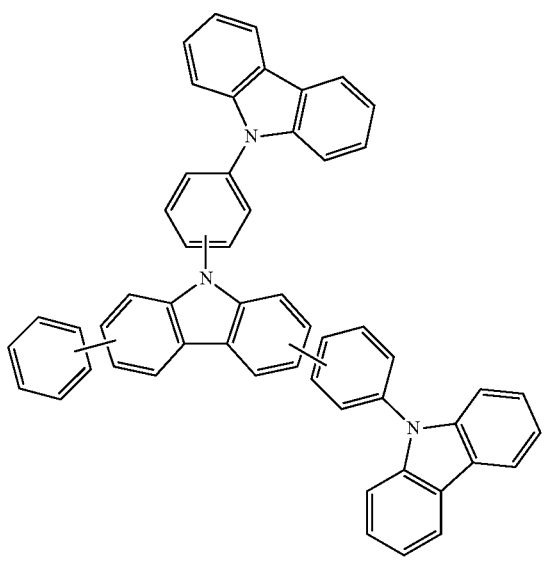
92
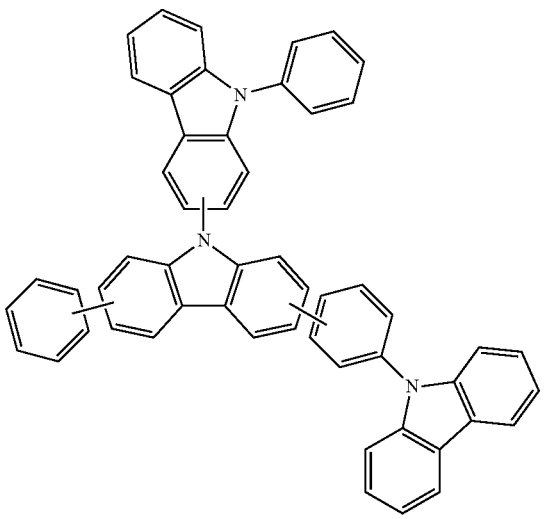
93
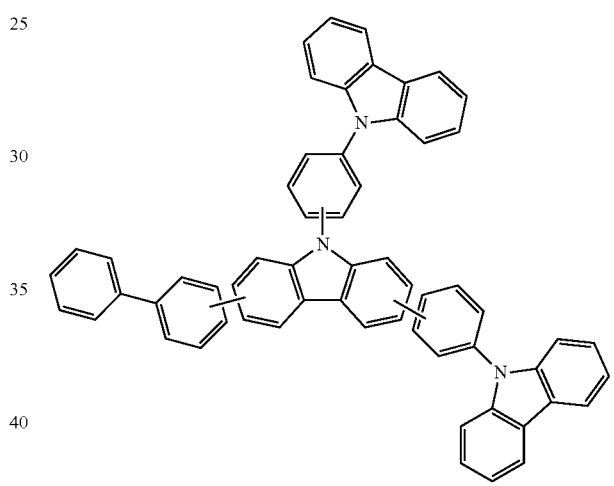
94
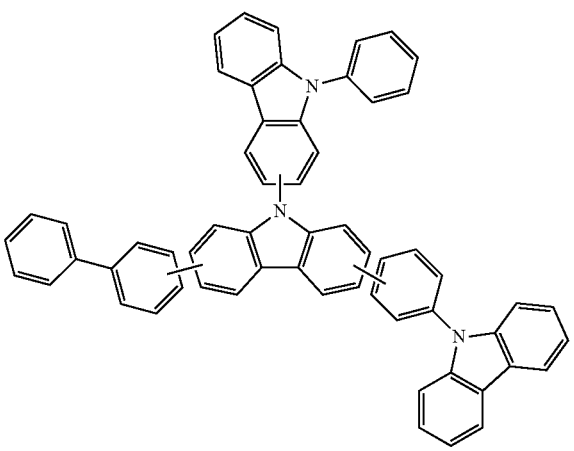

95
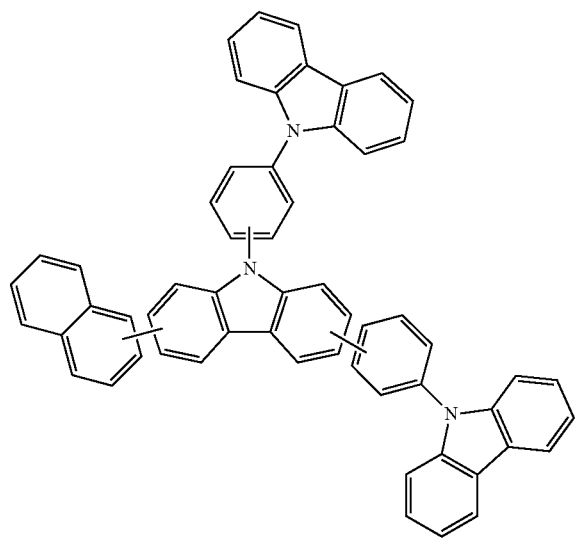
96
98
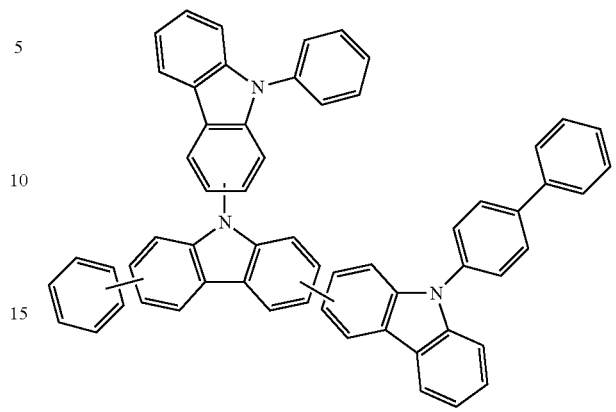
99
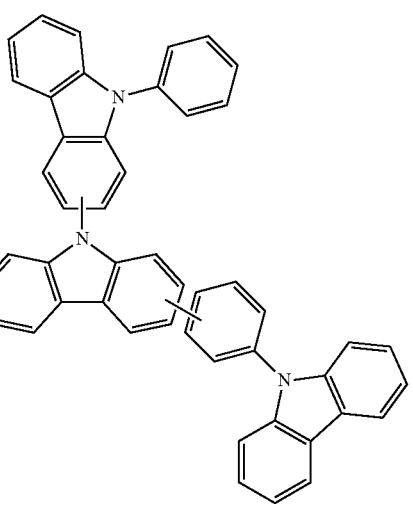
97
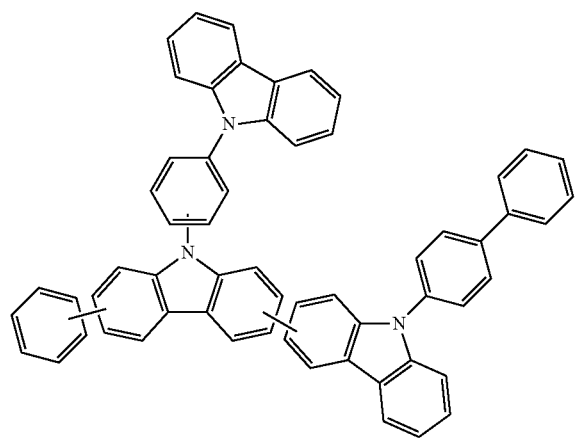
100
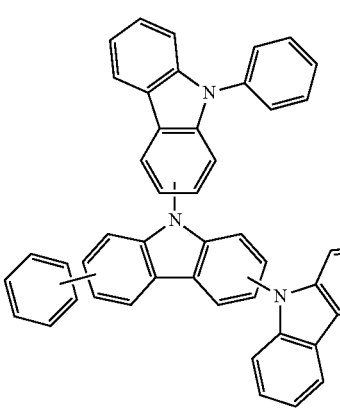

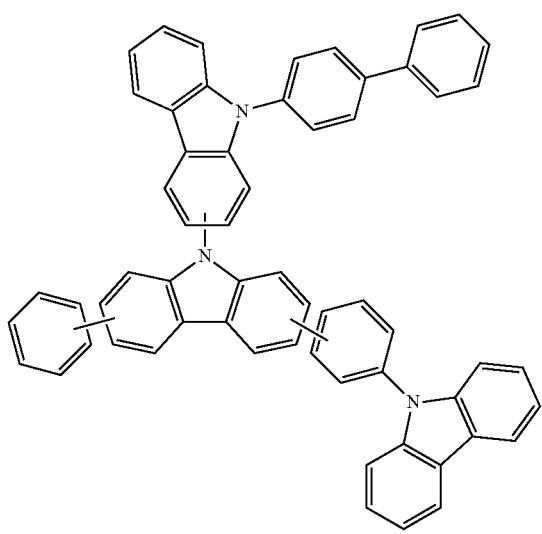
101
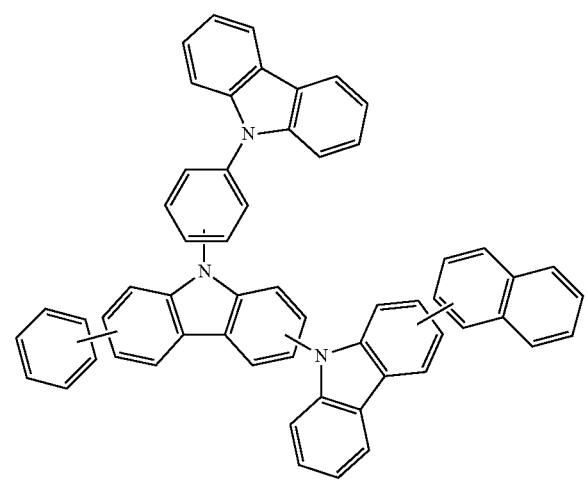
104
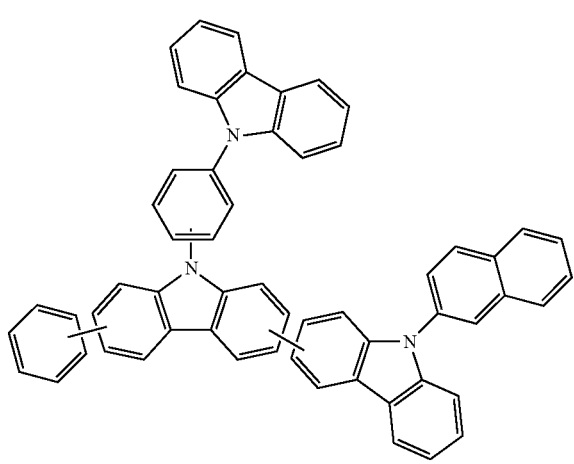
102
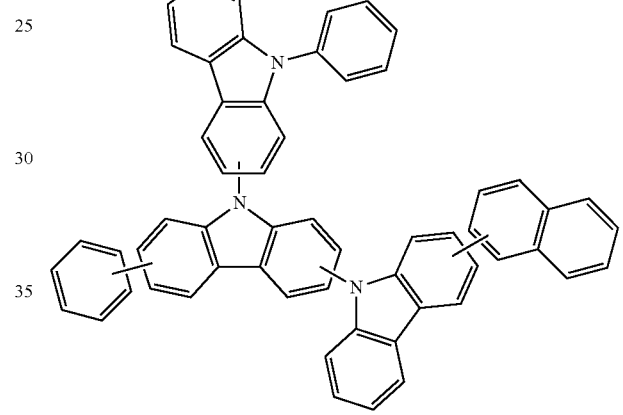
105
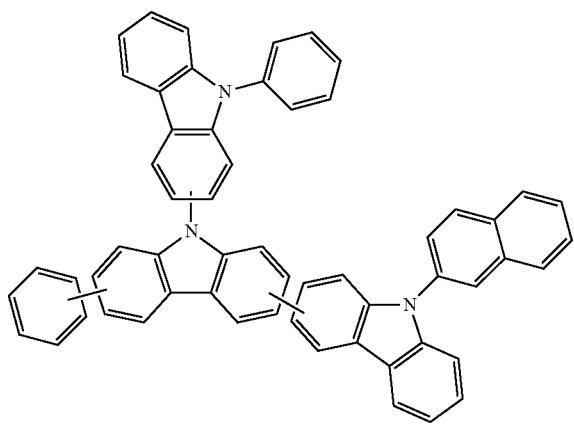
103
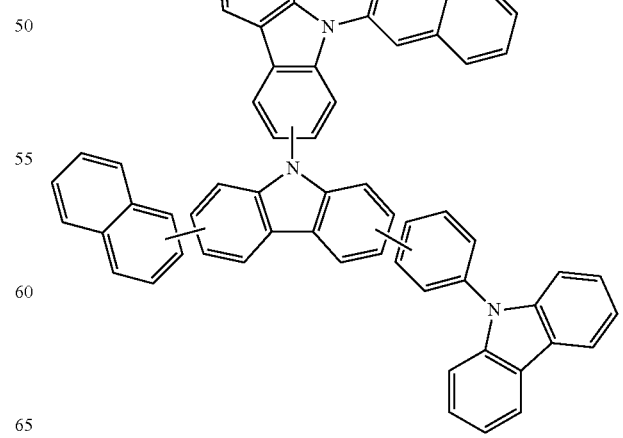
106

107
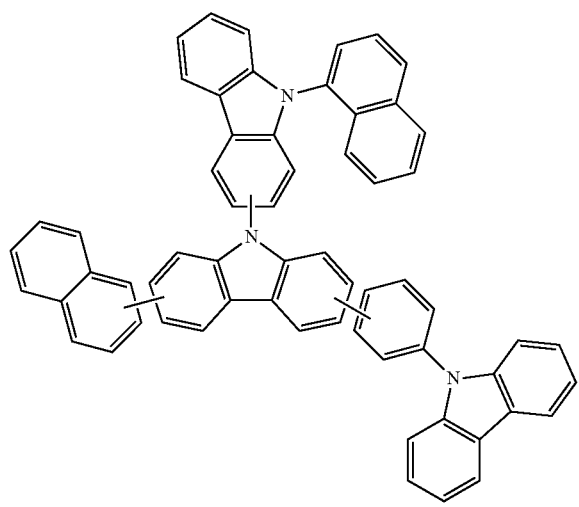
108
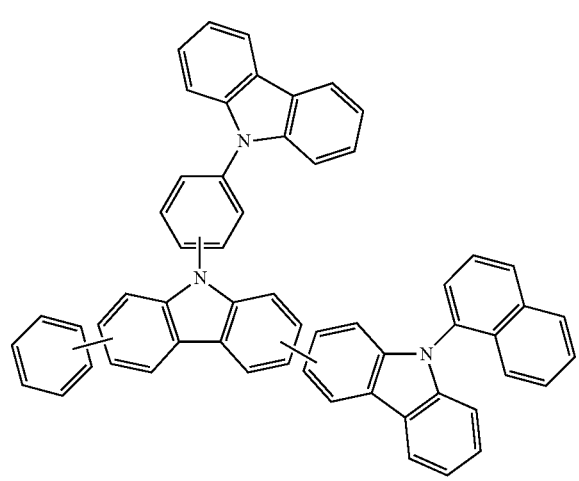
109
110
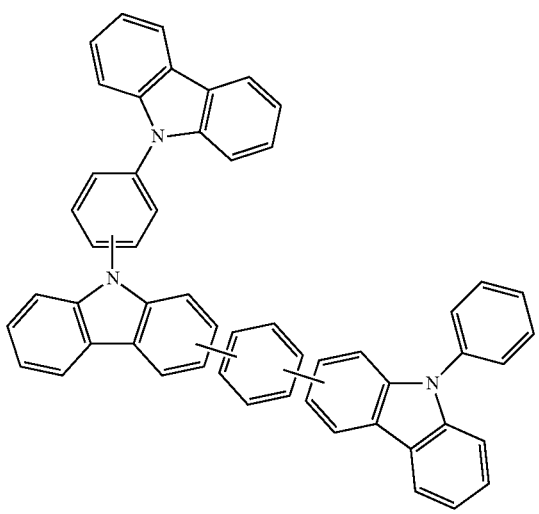
111
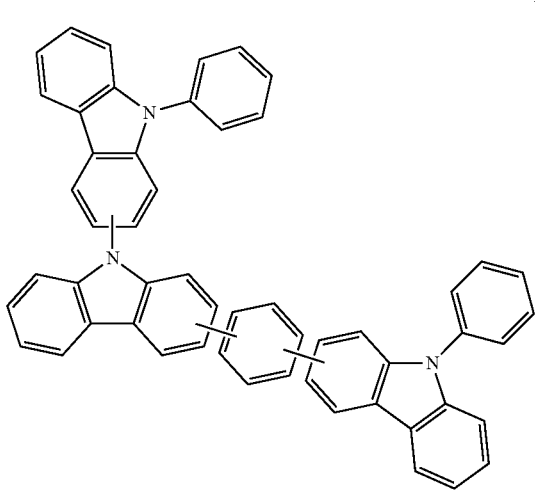
112
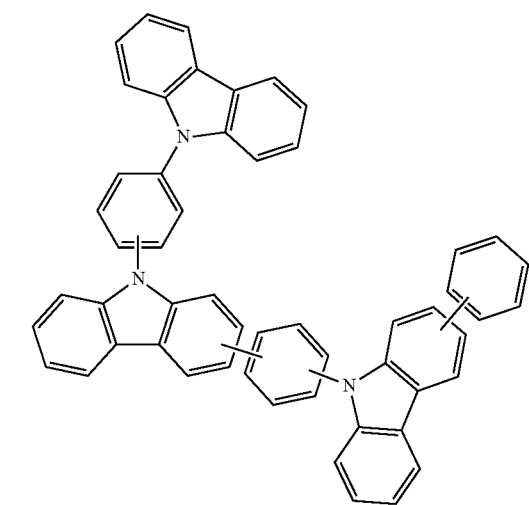

113
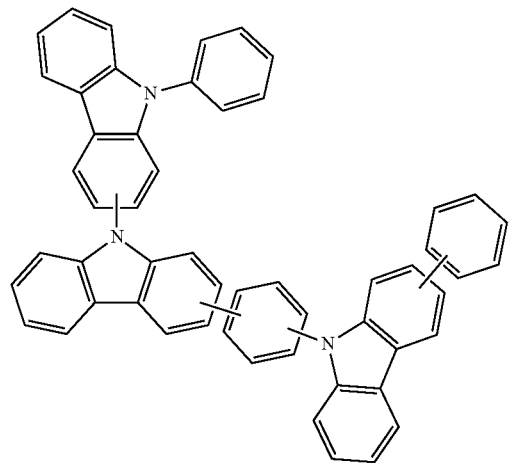
114
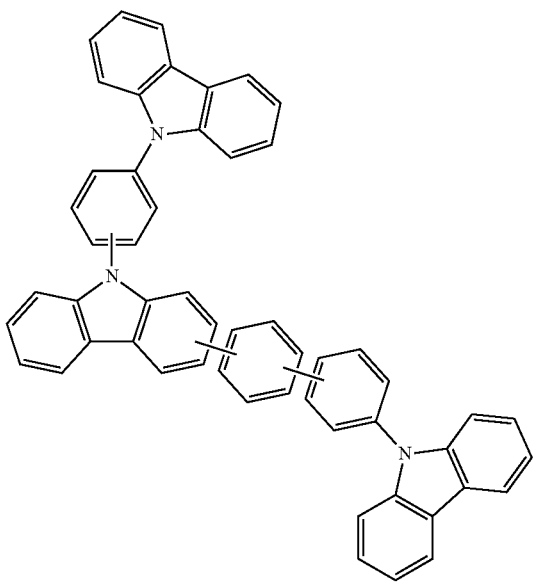
115
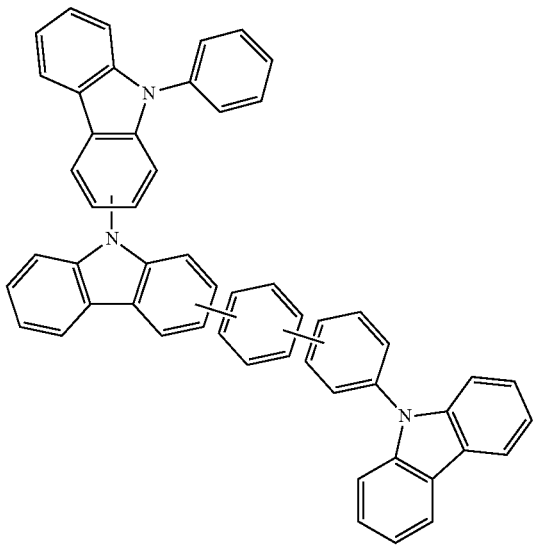
116
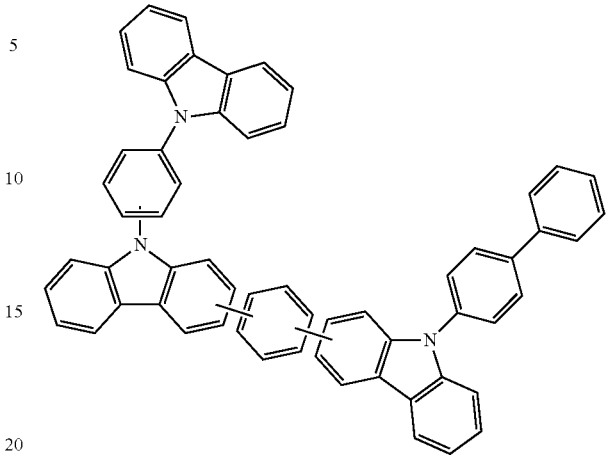
119
120
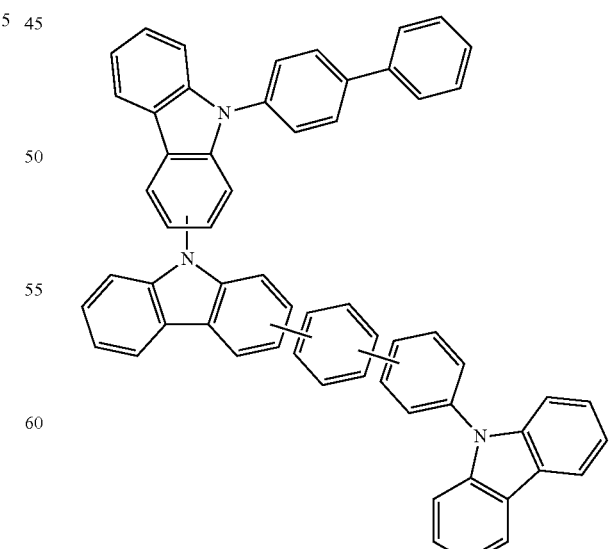

121
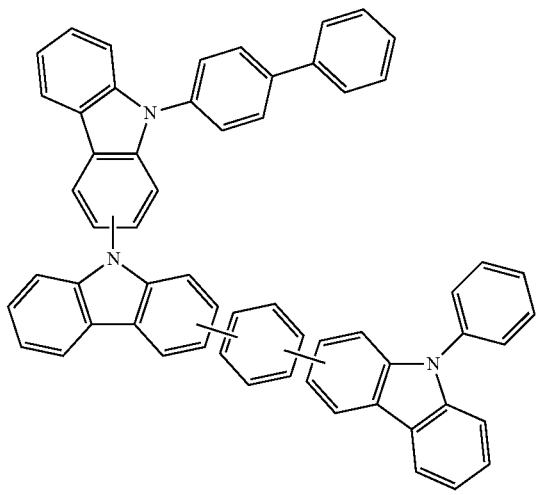
122
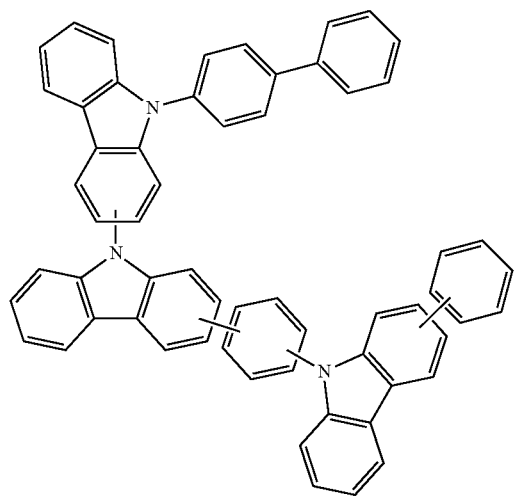
123
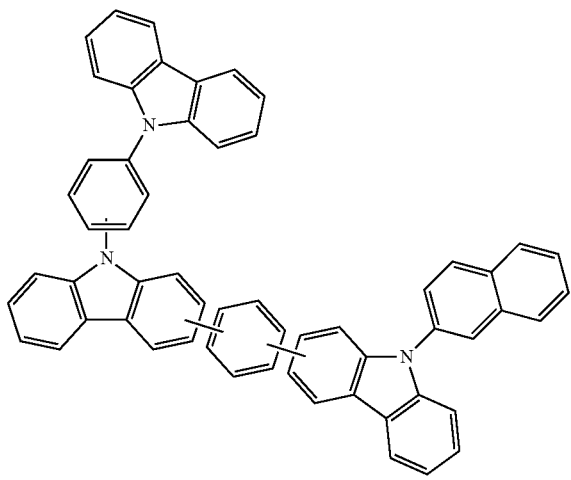
124
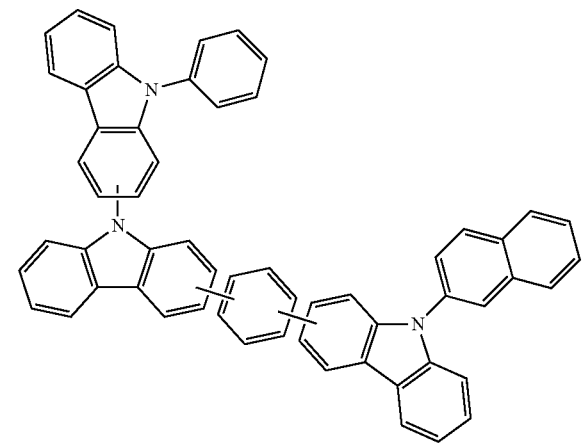
125
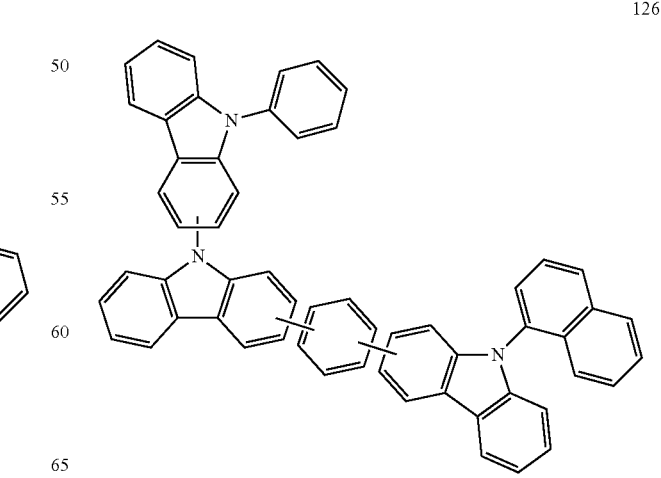
126

127
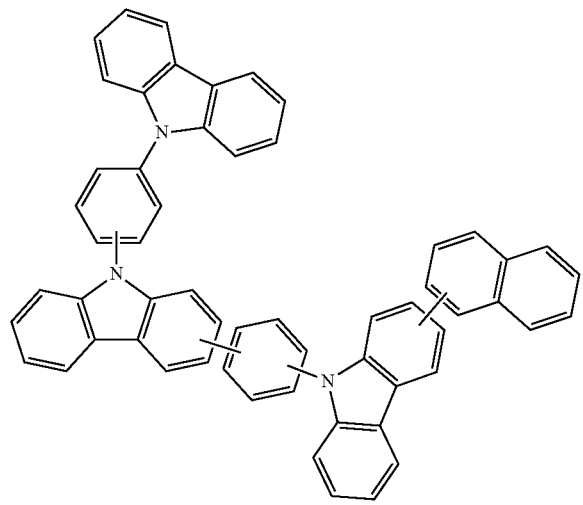
128
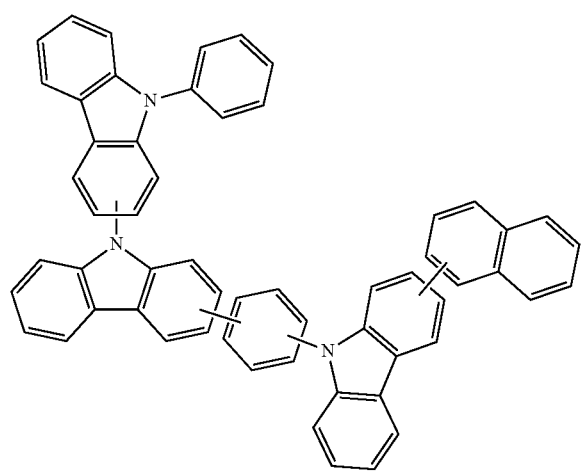
129
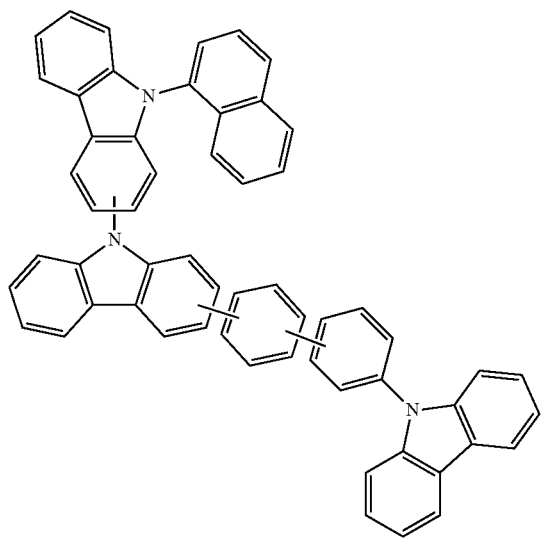
130
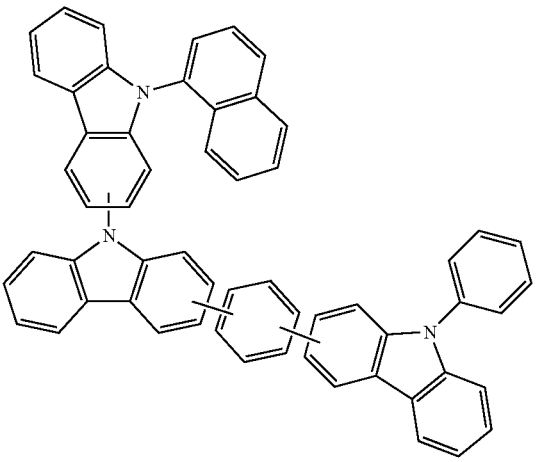
131
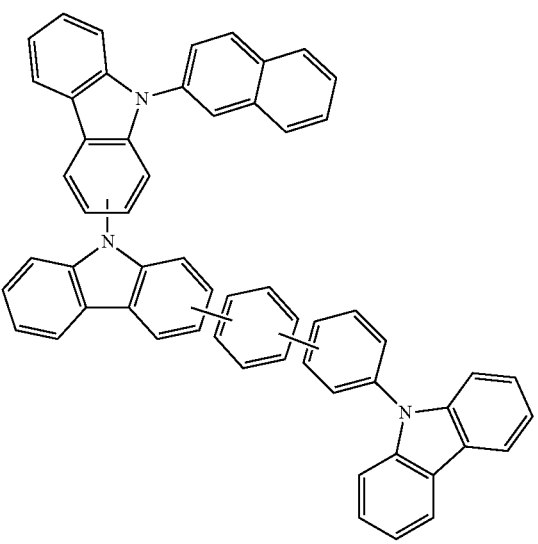
132
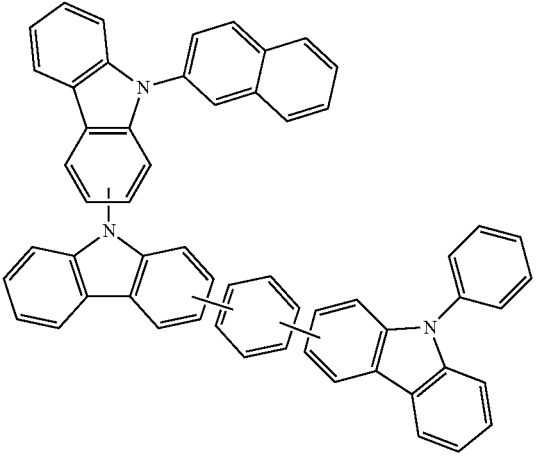

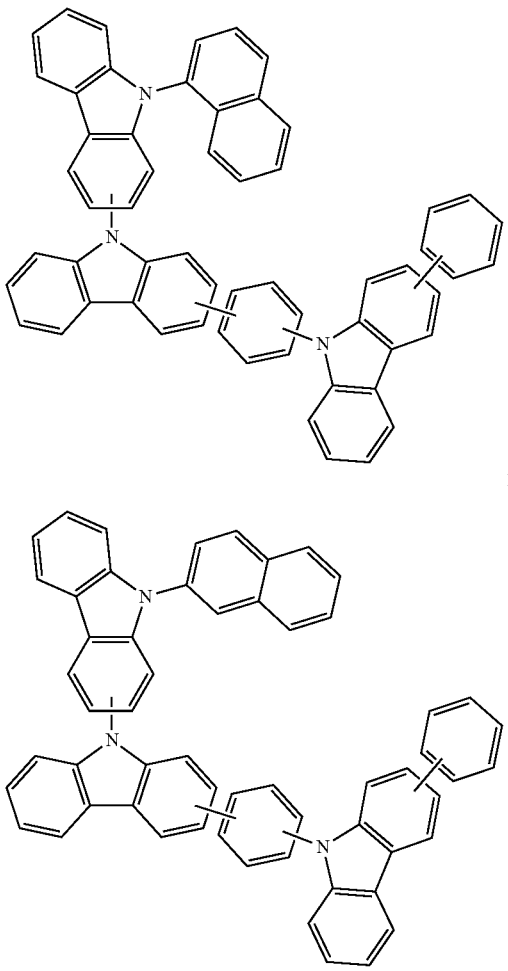

The photoelectric conversion device 100 may further include at least one auxiliary layer (not shown) between the first electrode 10 and the photoelectric conversion layer 30. The auxiliary layer may be disposed between the first electrode 10 and the organic buffer layer 40 and/or between the photoelectric conversion layer 30 and the organic buffer layer 40. The auxiliary layer may include an organic material, an inorganic material, and/or an organic/inorganic material.

The photoelectric conversion device 100 may further include an anti-reflective layer (not shown) on one surface of the first electrode 10 or the second electrode 20. The anti-reflective layer is disposed at a light incidence side and may lower reflectance of light of incident light and thereby light absorbance may be further improved. For example, when light is incident through the first electrode 10, the anti-reflective layer may be disposed on one surface of the first electrode 10, and when light is incident to the second electrode 20, anti-reflective layer may be disposed on one surface of the second electrode 20.

The anti-reflective layer may include, for example a material having a refractive index of about 1.6 to about 2.5, and may include for example at least one of metal oxide, metal sulfide, and an organic material having a refractive index within the ranges. The anti-reflective layer may include, for example a metal oxide such as aluminum-containing oxide, molybdenum-containing oxide, tungsten-containing oxide, vanadium-containing oxide, rhenium-containing oxide, niobium-containing oxide, tantalum-containing oxide, titanium-containing oxide, nickel-containing oxide, copper-containing oxide, cobalt-containing oxide, manganese-containing oxide, chromium-containing oxide, tellurium-containing oxide, or a combination thereof; a metal sulfide such as zinc sulfide; or an organic material such as an amine derivative, but is not limited thereto.

In the photoelectric conversion device 100, when light enters through the first electrode 10 or the second electrode 20 and the photoelectric conversion layer 30 may be configured to absorb light in a desired and/or alternatively predetermined wavelength region, excitons may be produced therein. The excitons may be separated into holes and electrons in the photoelectric conversion layer 30, and the separated holes may be transported to an anode that is one of the first electrode 10 and the second electrode 20 and the separated electrons may be transported to the cathode that is the other of the first electrode 10 and the second electrode 20, so as to flow a current.

Hereinafter, a photoelectric conversion device according to an embodiment is illustrated.

Figure 2:
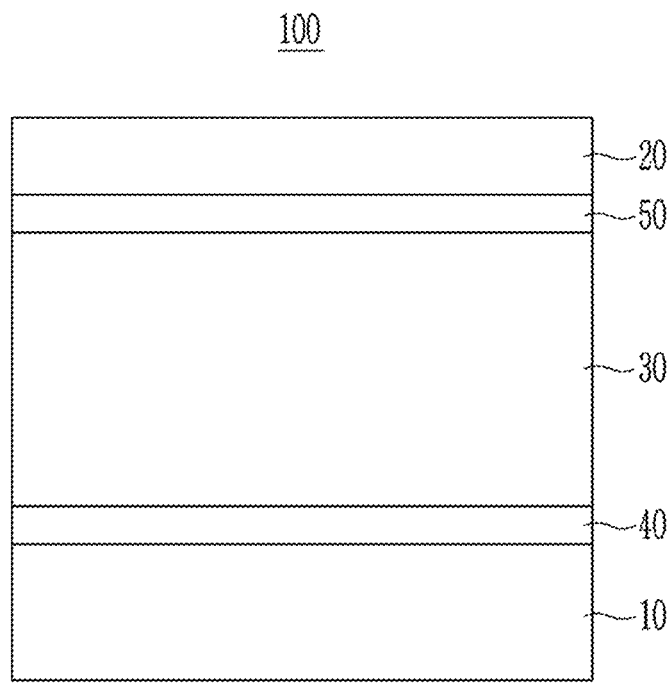
FIG. 2 is a cross-sectional view showing an example of a photoelectric conversion device according to example embodiments.

FIG. 2 is a cross-sectional view showing an example of a photoelectric conversion device according to some embodiments.

Referring to FIG. 2, the photoelectric conversion device 100 of the present embodiment, like the above embodiment, includes the first electrode 10, the second electrode 20, the photoelectric conversion layer 30, and the organic buffer layer 40.

However, the photoelectric conversion device 100 according to the present embodiment, unlike above embodiment, further includes an inorganic buffer layer 50 between the second electrode 20 and the photoelectric conversion layer 30. The inorganic buffer layer 50 may facilitate transfer of charge carriers (e.g., electrons) separated from the photoelectric conversion layer 30 and thus increase efficiency.

The inorganic buffer layer 50 may include, for example, lanthanoid, calcium (Ca), potassium (K), aluminum (Al), or an alloy thereof. The lanthanoid may include for example ytterbium (Yb). The inorganic auxiliary layer may have, for example, a thickness of less than or equal to about 5 nm.

The photoelectric conversion device 100 may further include at least one auxiliary layer (not shown) between the second electrode 20 and the photoelectric conversion layer 30. The auxiliary layer may be disposed between the second electrode 20 and the inorganic buffer layer 50 and/or between the photoelectric conversion layer 30 and the inorganic buffer layer 50. The auxiliary layer may include an organic material, an inorganic material, and/or an organic/inorganic material.

The aforementioned photoelectric conversion device 100 may be applied to, for example, a sensor, and the sensor may be, for example, an image sensor. The image sensor to which the aforementioned photoelectric conversion device 100 is applied may have optical electrical characteristics and may be suitable for high speed photographing by reducing an after-image (image-sticking) due to remaining charge carriers.

Hereinafter, an example of an image sensor to which the aforementioned device is applied is described with reference to the drawings. An organic CMOS image sensor is described as an example of the image sensor.

Figure 3:
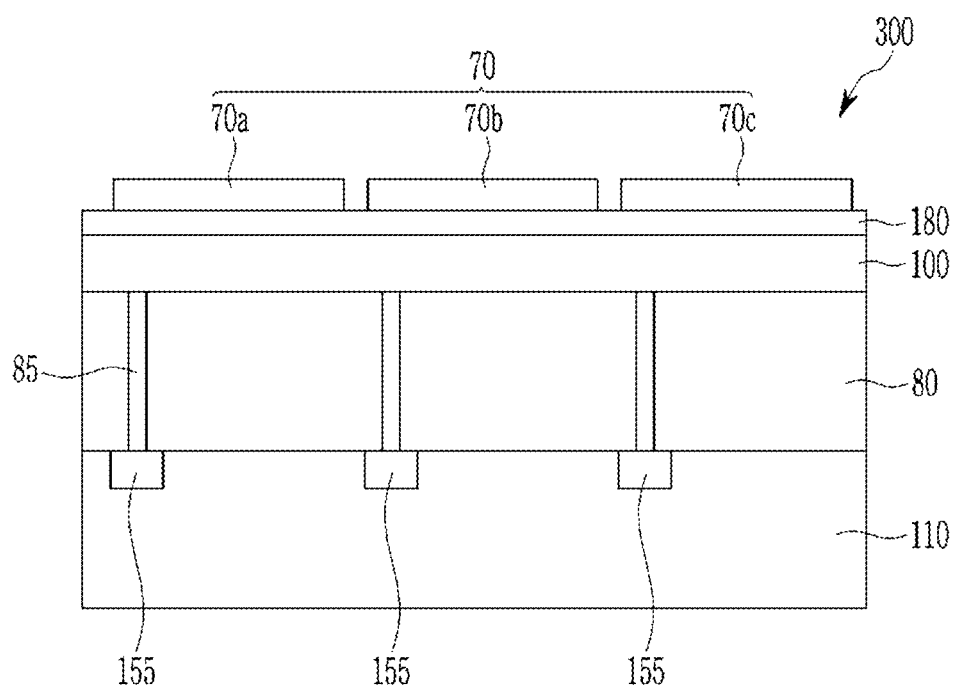
FIG. 3 is a cross-sectional view showing an example of an image sensor according to example embodiments.

FIG. 3 is a cross-sectional view showing an example of an image sensor according to some embodiments.

Referring to FIG. 3, an image sensor 300 according to an embodiment includes a semiconductor substrate 110, an insulating layer 80, a photoelectric conversion device 100, and a color filter layer 70.

The semiconductor substrate 110 may be a silicon substrate, and is integrated with the transmission transistor (not shown) and the charge storage 155. The transmission transistor and/or the charge storage 155 may be integrated in each pixel. The charge storage 155 is electrically connected to the photoelectric conversion device 100.

A metal wire (not shown) and a pad (not shown) are formed on the semiconductor substrate 110. In order to decrease signal delay, the metal wire and pad may be made of a metal having low resistivity, for example, aluminum (Al), copper (Cu), silver (Ag), or an alloy thereof, but are not limited thereto.

The insulation layer 80 is formed on the metal line and pad. The insulation layer 80 may be made of an inorganic insulating material such as a silicon oxide and/or a silicon nitride, or a low dielectric constant (low K) material such as SiC, SiCOH, SiCO, and SiOF. The insulation layer 80 has a trench 85 exposing the charge storage 155. The trench 85 may be filled with fillers.

The aforementioned photoelectric conversion device 100 is formed on the insulation layer 80. The photoelectric conversion device 100 may have the structure shown in FIG. 1 or 2, and the detailed description thereof is the same as described above. One of the first electrode 10 and the second electrode 20 of the photoelectric conversion device 100 may be a light-receiving electrode, and the other of the first electrode 10 and the second electrode 20 of the photoelectric conversion device 100 may be connected to the charge storage 155.

The color filter layer 70 is formed on the photoelectric conversion device 100. The color filter layer 70 includes a blue filter 70a formed in a blue pixel, a red filter 70b formed in a red pixel, and a green filter 70c formed in a green pixel. However, the color filter layer 70 may include a cyan filter, a magenta filter, and/or a yellow filter instead of the blue filter 70a, the red filter 70b and/or the green filter 70c or may further include them in addition to the blue filter 70a, the red filter 70b and/or the green filter 70c.

An insulating layer 180 is formed between the photoelectric conversion device 100 and the color filter layer 70. The insulation layer 180 may be omitted.

Focusing lens (not shown) may be further formed on the color filter layer 70. The focusing lens may control a direction of incident light and gather the light in one region. The focusing lens may have a shape of, for example, a cylinder or a hemisphere, but is not limited thereto.

Figure 4:
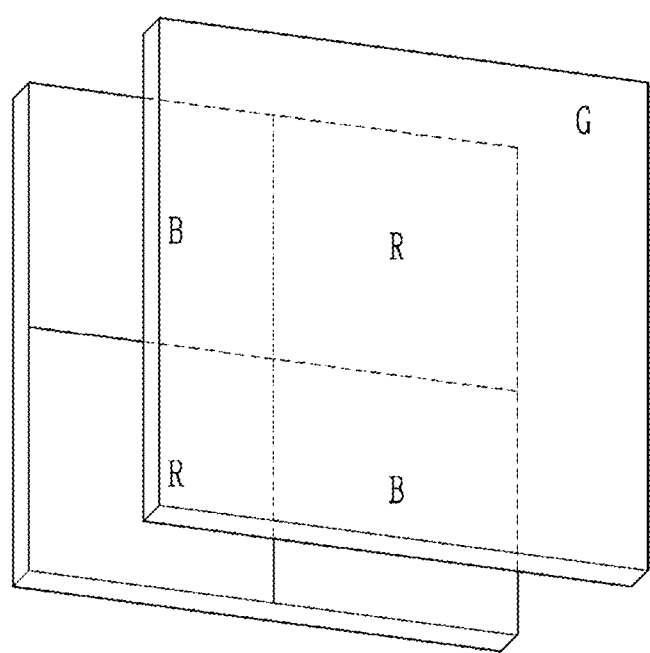
FIG. 4 is a plan view showing an example of an image sensor according to example embodiments.
Figure 5:
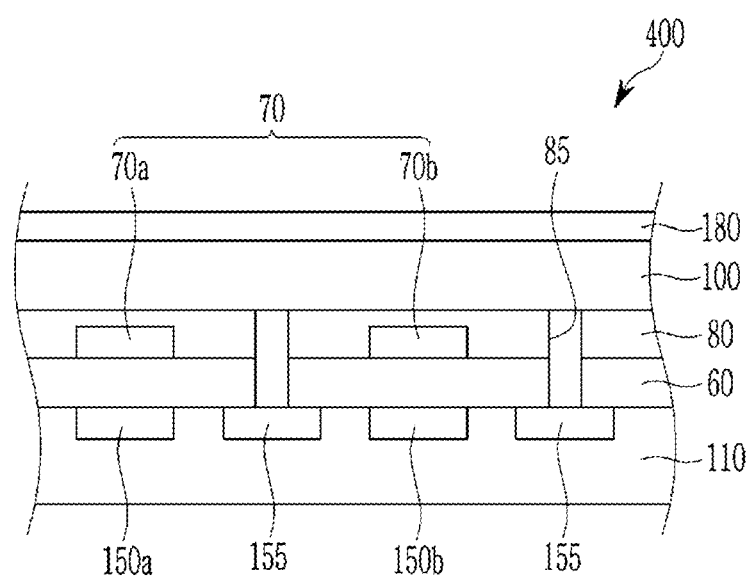
FIG. 5 is a cross-sectional view showing an example of the image sensor of FIG. 4.

FIG. 4 is a plan view showing an example of an image sensor according to some embodiments and FIG. 5 is a cross-sectional view showing an example of the image sensor of FIG. 4.

Referring to FIGS. 4 and 5, an image sensor 400 according to some embodiments includes a semiconductor substrate 110 integrated with photo-sensing devices 150a and 150b, a transmission transistor (not shown), and a charge storage 155; a lower insulation layer 60; a color filter layer 70; an upper insulation layer 80; and the aforementioned photoelectric conversion device 100.

The semiconductor substrate 110 may be a silicon substrate, and is integrated with the photo-sensing devices 150a and 150b, the transmission transistor (not shown), and the charge storage 155. The photo-sensing devices 150a and 150b may be photodiodes.

The photo-sensing devices 150a and 150b, the transmission transistor, and/or the charge storage 155 may be integrated in each pixel, and as shown in the drawing, the photo-sensing devices 150a and 150b may be respectively included in a blue pixel and a red pixel and the charge storage 155 may be included in a green pixel.

The photo-sensing devices 150a and 150b sense light, the information sensed by the photo-sensing devices may be transferred by the transmission transistor, the charge storage 155 is electrically connected to the photoelectric conversion device 100 that will be described later, and the information of the charge storage 155 may be transferred by the transmission transistor.

A metal wire (not shown) and a pad (not shown) are formed on the semiconductor substrate 110. In order to decrease signal delay, the metal wire and pad may be made of a metal having low resistivity, for example, aluminum (Al), copper (Cu), silver (Ag), and alloys thereof, but are not limited thereto. However, it is not limited to the structure, and the metal wire and pad may be disposed under the photo-sensing devices 150a and 150b.

The lower insulation layer 60 is formed on the metal wire and the pad. The lower insulation layer 60 may be made of an inorganic insulating material such as a silicon oxide and/or a silicon nitride, or a low dielectric constant (low K) material such as SiC, SiCOH, SiCO, and SiOF. The lower insulation layer 60 has a trench exposing the charge storage 155. The trench may be filled with fillers.

A color filter layer 70 is formed on the lower insulation layer 60. The color filter layer 70 includes a blue filter 70a formed in a blue pixel and a red filter 70b in a red pixel. However, the present disclosure is not limited thereto and may include a cyan filter, a magenta filter and/or a yellow filter instead or additionally. In the present embodiment, a green filter is not included, but a green filter may be further included.

The upper insulation layer 80 is formed on the color filter layer 70. The upper insulation layer 80 eliminates a step caused by the color filter layer 70 and smoothens the surface. The upper insulation layer 80 and the lower insulation layer 60 may include a contact hole (not shown) exposing a pad, and a trench 85 exposing a charge storage 155 of a green pixel.

The aforementioned photoelectric conversion device 100 is formed on the upper insulating layer 80. The photoelectric conversion device 100 may have the structure shown in FIG. 1 or 2, and the detailed description thereof is the same as described above. One of the first electrode 10 and the second electrode 20 of the photoelectric conversion device 100 may be a light-receiving electrode, and the other of the first electrode 10 and the second electrode 20 of the photoelectric conversion device 100 may be connected to the charge storage 155.

Focusing lens (not shown) may be further formed on the photoelectric conversion device 100. The focusing lens may control a direction of incident light and gather the light in one region. The focusing lens may have a shape of, for example, a cylinder or a hemisphere, but is not limited thereto.

Figure 6:
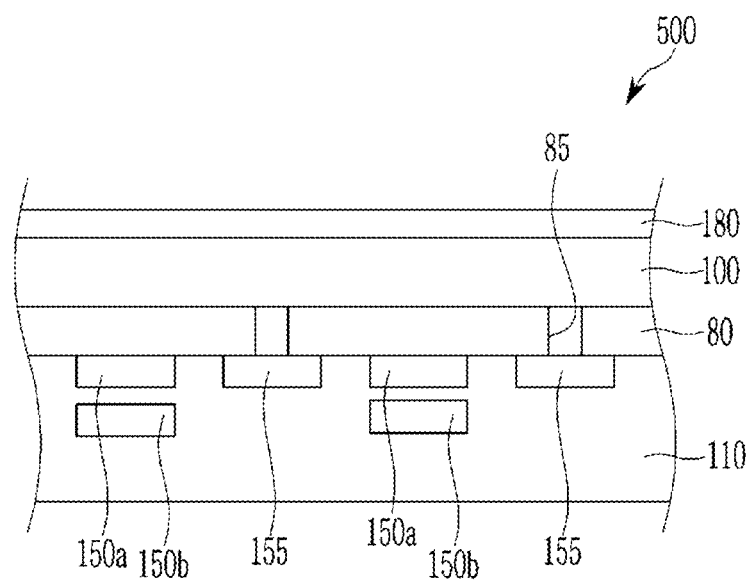
FIG. 6 is a cross-sectional view showing an example of the image sensor of FIG. 4.

FIG. 6 is a cross-sectional view showing another example of the image sensor of FIG. 4.

Referring to FIG. 6, an image sensor 500 according to the present embodiment includes a semiconductor substrate 110 integrated with photo-sensing devices 150a and 150b, a transmission transistor (not shown), and a charge storage 155, a lower insulation layer 60, a color filter layer 70, an upper insulation layer 80, and a photoelectric conversion device 100.

However, in the image sensor 500 according to the present embodiment, unlike the aforementioned embodiment, the photo-sensing devices 150a and 150b are stacked in the vertical direction and the color filter layer 70 is omitted. The photo-sensing devices 150a and 150b are electrically connected to a charge storage (not shown) and may be transferred by a transfer transistor. The photo-sensing devices 150a and 150b may selectively absorb light in each wavelength region according to the stacking depth.

The photoelectric conversion device 100 may have the structure shown in FIG. 1 or 2, and the detailed description thereof is the same as described above. One of the first electrode 10 and the second electrode 20 of the photoelectric conversion device 100 may be a light-receiving electrode, and the other of the first electrode 10 and the second electrode 20 of the photoelectric conversion device 100 may be connected to the charge storage 155.

Figure 7:
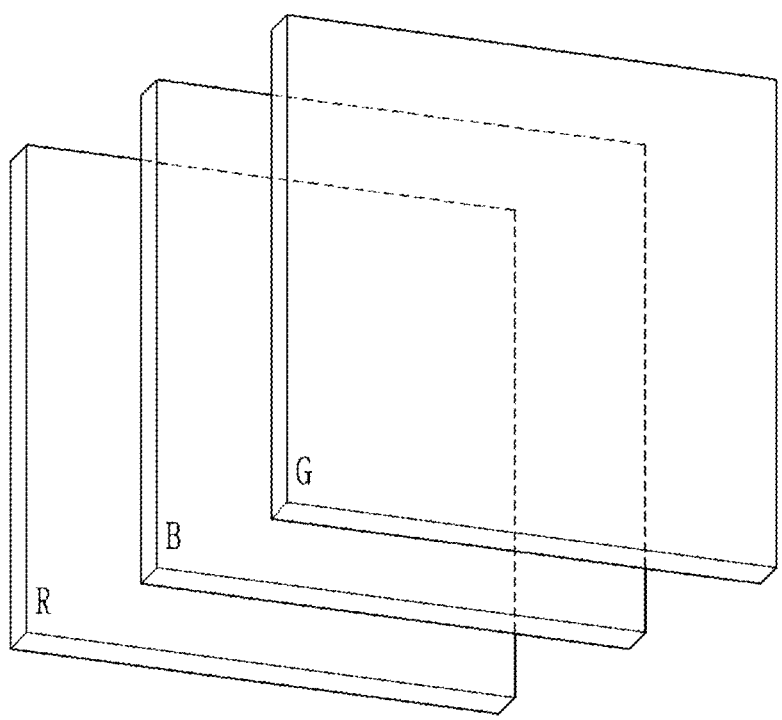
FIG. 7 is a plan view showing an example of an image sensor according to example embodiments.
Figure 8:
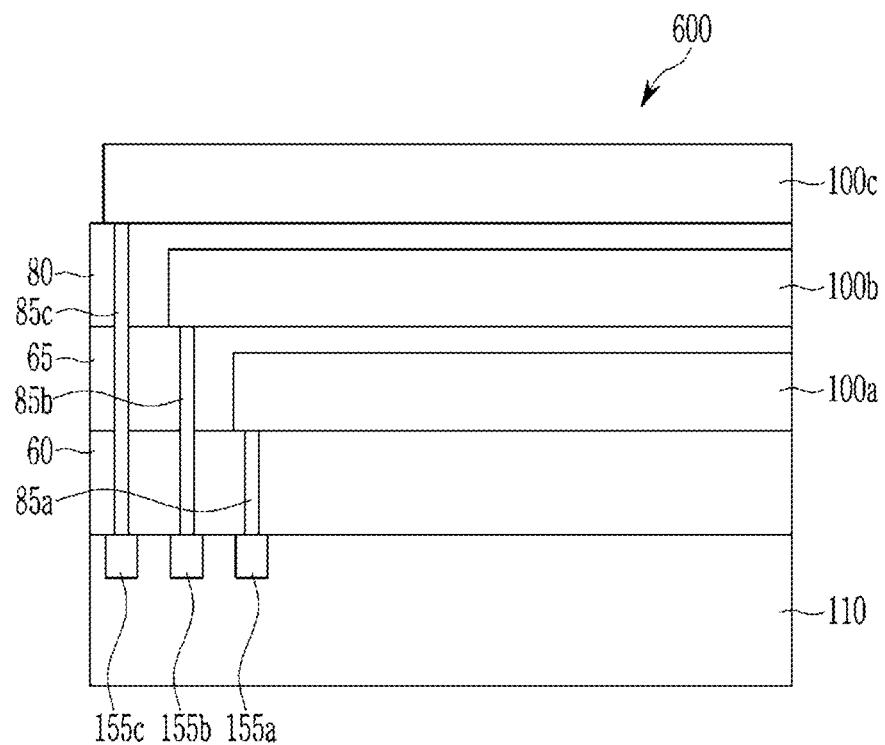
FIG. 8 is a cross-sectional view showing an example of the image sensor of FIG. 7.

FIG. 7 is a plan view showing another example of an image sensor according to some embodiments, and FIG. 8 is a cross-sectional view showing an example of the image sensor of FIG. 7.

An image sensor 600 according to the present embodiment has a structure in which a green device configured to selectively absorb light in a green wavelength region, a blue device configured to selectively absorb light in a blue wavelength region, and a red device configured to selectively absorb light in a red wavelength region are stacked.

The image sensor 600 according to the present embodiment includes a semiconductor substrate 110, a lower insulation layer 60, an intermediate insulation layer 65, an upper insulation layer 80, a first photoelectric conversion device 100a, a second photoelectric conversion device 100b, and a third photoelectric conversion device 100c.

The semiconductor substrate 110 may be a silicon substrate, and is integrated with the transmission transistor (not shown) and the charge storages 155a, 155b, and 155c.

A metal wire (not shown) and a pad (not shown) are formed on the semiconductor substrate 110, and the lower insulation layer 60 is formed on the metal wire and the pad.

The first photoelectric conversion device 100a, the second photoelectric conversion device 100b, and the third photoelectric conversion device 100c are sequentially formed on the lower insulation layer 60.

The first, second, and third photoelectric conversion devices 100a, 100b, and 100c may each independently have the structure shown in FIG. 1 or 2, and the detailed descriptions thereof are the same as described above. One of the first electrode 10 and the second electrode 20 of the first, second and third photoelectric conversion devices 100a, 100b, and 100c may be a light-receiving electrode, and the other of the first electrode 10 and the second electrode 20 of the first, second and third photoelectric conversion devices 100a, 100b, and 100c may be connected to the charge storages 155a, 155b, and 155c.

The first photoelectric conversion device 100a may selectively absorb light in one of red, blue, and green wavelength regions and may photoelectrically convert it. For example, the first photoelectric conversion device 100a may be a red photoelectric conversion device. The intermediate insulation layer 65 is formed on the first photoelectric conversion device 100a.

A second photoelectric conversion device 100b is formed on the intermediate insulation layer 65.

The second photoelectric conversion device 100b may selectively absorb light in one of red, blue, and green wavelength regions and may photoelectrically convert it. For example, the second photoelectric conversion device 100b may be a blue photoelectric conversion device.

The upper insulation layer 80 is formed on the second photoelectric conversion device 100b. The lower insulation layer 60, the intermediate insulation layer 65, and the upper insulation layer 80 have a plurality of trenches 85a, 85b, and 85c exposing charge storages 155a, 155b, and 155c.

The third photoelectric conversion device 100c is formed on the upper insulation layer 80. The third photoelectric conversion device 100c may selectively absorb light in one of red, blue, and green wavelength regions and may photoelectrically convert it. For example, the third photoelectric conversion device 100c may be a green photoelectric conversion device.

Focusing lens (not shown) may be further formed on the third photoelectric conversion device 100c. The focusing lens may control a direction of incident light and gather the light in one region. The focusing lens may have a shape of, for example, a cylinder or a hemisphere, but is not limited thereto.

In the drawing, the first photoelectric conversion device 100a, the second photoelectric conversion device 100b, and the third photoelectric conversion device 100c are sequentially stacked, but the present disclosure is not limited thereto, and they may be stacked in various orders.

As described above, the first photoelectric conversion device 100a, the second photoelectric conversion device 100b, and the third photoelectric conversion device 100c are stacked, and thus the size of an image sensor may be reduced to realize a down-sized image sensor.

Figure 9:
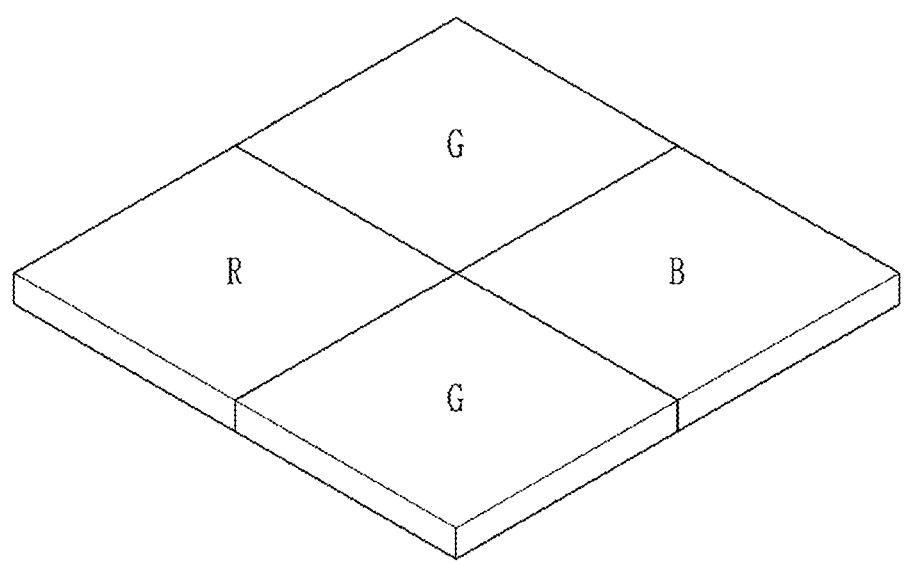
FIG. 9 is a plan view showing another example of an image sensor according to example embodiments.
Figure 10:
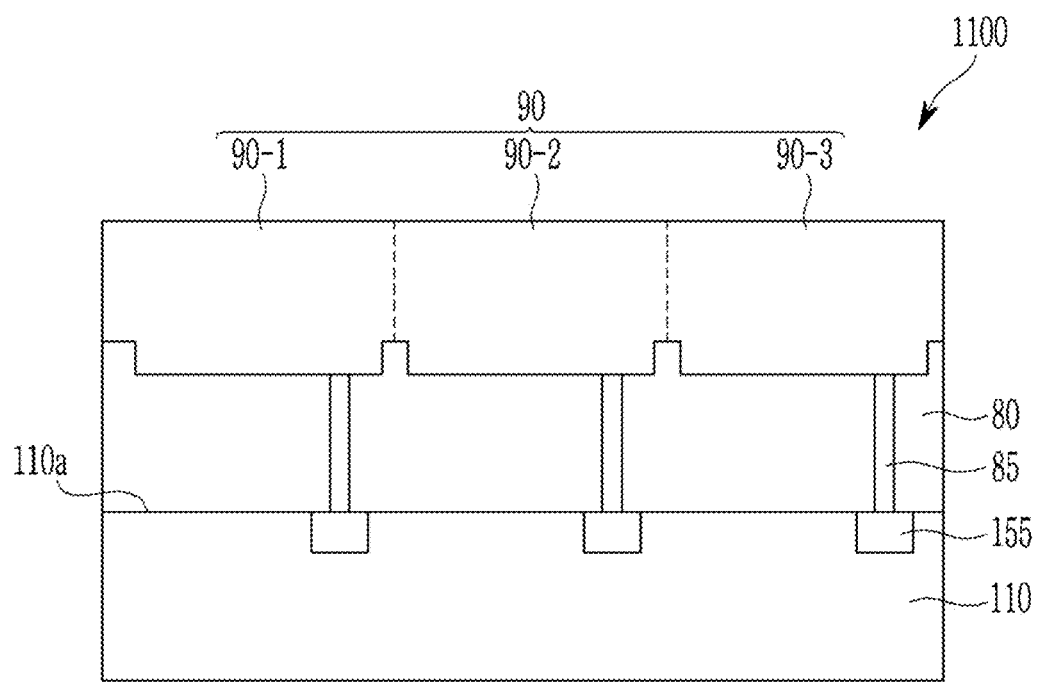
FIG. 10 is a cross-sectional view showing an example of the image sensor of FIG. 9.

FIG. 9 is a plan view showing another example of an image sensor according to an embodiment and FIG. 10 is a cross-sectional view showing an example of the image sensor of FIG. 9.

Referring to FIGS. 9 and 10, an image sensor 1100 includes a photoelectric conversion device 90 disposed on a semiconductor substrate 110, and the photoelectric conversion device 90 includes a plurality of photoelectric conversion devices 90-1, 90-2, and 90-3. The plurality of the photoelectric conversion devices 90-1, 90-2, and 90-3 may convert light (e.g., blue light, green light, or red light) in different wavelength regions into an electrical signal. Referring to FIG. 10, a plurality of the photoelectric conversion devices 90-1, 90-2, and 90-3 may be arranged on the semiconductor substrate 110 in a horizontal direction such that the photoelectric conversion devices 90-1, 90-2, and 90-3 may be partially or entirely overlapped with each other in a direction extending in parallel with the surface 110a of the semiconductor substrate 110. Each photoelectric conversion device 90-1, 90-2, and 90-3 is connected to a charge storage 155 integrated in the semiconductor substrate 110 through a trench 85.

Each photoelectric conversion device 90-1, 90-2, and 90-3 may be one of the aforementioned photoelectric conversion devices 100 and 200. For example, two or more photoelectric conversion devices 90-1, 90-2, and 90-3 may include different portions of a common, continuous layer that extends continuously between the photoelectric conversion devices 90-1, 90-2, and 90-3. For example, the plurality of photoelectric conversion devices 90-1, 90-2, and 90-3 may share a common first electrode 10 and/or a common second electrode 20. For example, two or more of the photoelectric conversion devices 90-2, 90-2, and 90-3 may have different photoelectric conversion layer 30 configured to absorb different wavelength regions of incident light. Other configurations of the image sensor 1100 may be the same as one or more of the image sensors described with reference to FIGS. 3 to 8.

Figure 11:
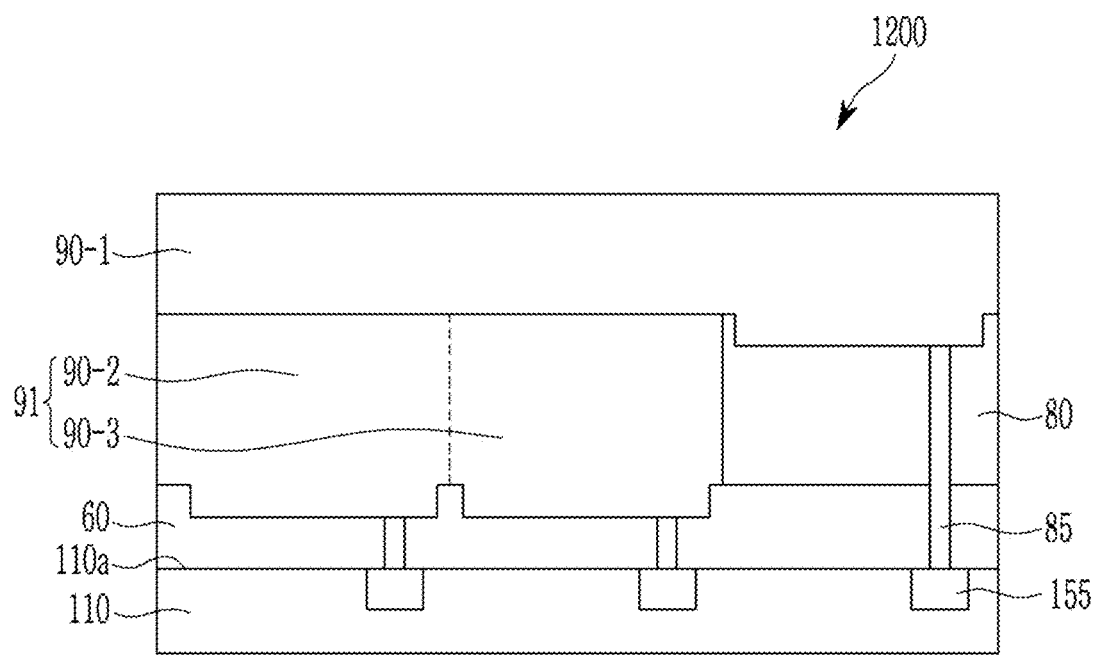
FIG. 11 is a cross-sectional view showing an example of an image sensor according to example embodiments.

FIG. 11 is a cross-sectional view showing an example of an image sensor according to some embodiments.

Referring to FIG. 11, an image sensor 1200 includes a semiconductor substrate 110 and photoelectric conversion devices 90-1 and 91 which are stacked on the semiconductor substrate 110. The photoelectric conversion device 91 includes a plurality of photoelectric conversion devices 90-2 and 90-3 and the plurality of photoelectric conversion devices 90-2 and 90-3 may be arranged to be overlapped with each other in a direction extending in parallel with the surface 110a of the semiconductor substrate 110. The plurality of the photoelectric conversion devices 90-1, 90-2, and 90-3 may convert light (e.g., blue light, green light, or red light) in different wavelength regions into an electrical signal.

As an example, the photoelectric conversion device 90-1 may include horizontally-arranged, plurality of photoelectric conversion devices configured to absorb light in different wavelength regions. As an example, the photoelectric conversion device 91 may photoelectrically convert light of one wavelength region selected from blue light, green light, and red light. As an example, the photoelectric conversion device 91 may be partially or entirely overlapped with the photoelectric conversion device 90-1. Other configurations of the image sensor 1200 may be the same as one or more of the image sensors described with reference to FIGS. 3 to 8.

Figure 12:
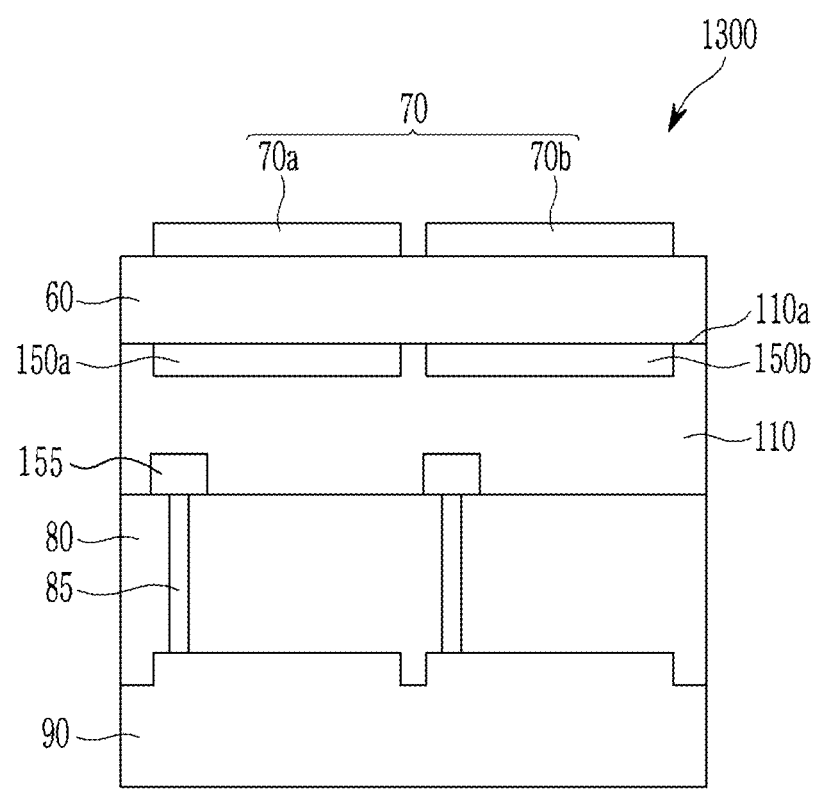
FIG. 12 is a cross-sectional view showing another example of an image sensor according to example embodiments.

FIG. 12 is a cross-sectional view showing another example of an image sensor according to some embodiments.

Referring to FIG. 12, an image sensor 1300 includes a semiconductor substrate 110 integrated with photo-sensing devices 150a and 150b, a transmission transistor (not shown), and a charge storage 155; an upper insulation layer 80 and a color filter layer 70 which are disposed on the semiconductor substrate 110; a lower insulation layer 60 and a photoelectric conversion device 90 which are disposed under the semiconductor substrate 110. The photoelectric conversion device 90 may be the aforementioned photoelectric conversion devices 100 and 200. As shown in FIG. 12, the photoelectric conversion device 90 is disposed under the semiconductor substrate 110 and thereby the photoelectric conversion device 90 and the color filter layer 70 are separated with respect to the photo-sensing devices 150a and 150b. Other configurations of the image sensor 1300 may be the same as one or more of the image sensors described with reference to FIGS. 3 to 8.

The aforementioned photoelectric conversion device and sensor may be applied to various electronic devices, for example a mobile phone, a camera (see e.g., FIG. 14), a biometric device, and/or automotive electronic parts, but is not limited thereto.

Figure 13:
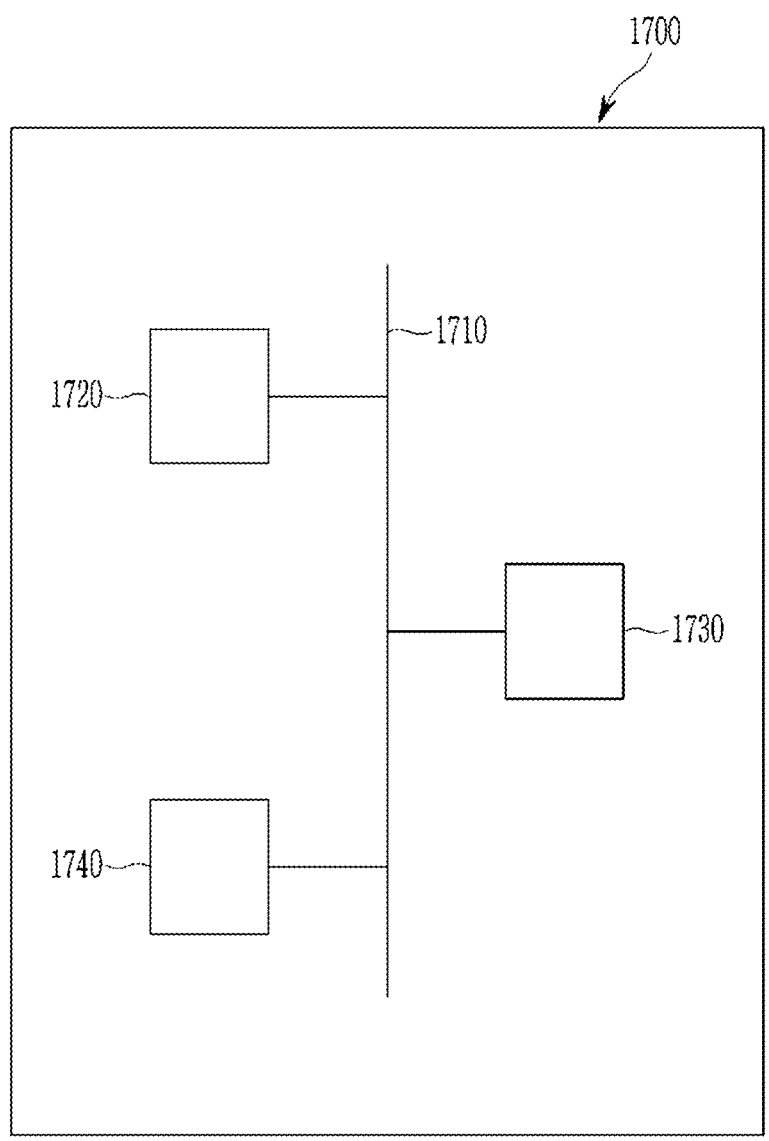
FIG. 13 is a schematic diagram of an electronic device according to example embodiments.

FIG. 13 is a schematic diagram showing an electronic device according to some embodiments.

Referring to FIG. 13, an electronic device 1700 may include a processor 1720, a memory 1730, and an image sensor 1740 that are electrically coupled together via a bus 1710. The image sensor 1740 may be one according to one of the aforementioned embodiments. The memory 1730, which may be a non-transitory computer readable medium and may store a program of instructions. The memory 1730 may be a nonvolatile memory, such as a flash memory, a phase-change random access memory (PRAM), a magneto-resistive RAM (MRAM), a resistive RAM (ReRAM), or a ferro-electric RAM (FRAM), or a volatile memory, such as a static RAM (SRAM), a dynamic RAM (DRAM), or a synchronous DRAM (SDRAM). The processor 1720 may execute the stored program of instructions to perform one or more functions. For example, the processor 1720 may be configured to process electrical signals generated by the organic sensor 1740. The processor 1720 may include processing circuitry such as hardware including logic circuits; a hardware/software combination such as a processor executing software; or a combination thereof. For example, the processing circuitry more specifically may include, but is not limited to, a central processing unit (CPU), an arithmetic logic unit (ALU), a digital signal processor, a microcomputer, a field programmable gate array (FPGA), a System-on-Chip (SoC), a programmable logic unit, a microprocessor, application-specific integrated circuit (ASIC), etc. The processor 1720 may be configured to generate an output (e.g., an image to be displayed on a display interface) based on such as processing.

Figure 14:
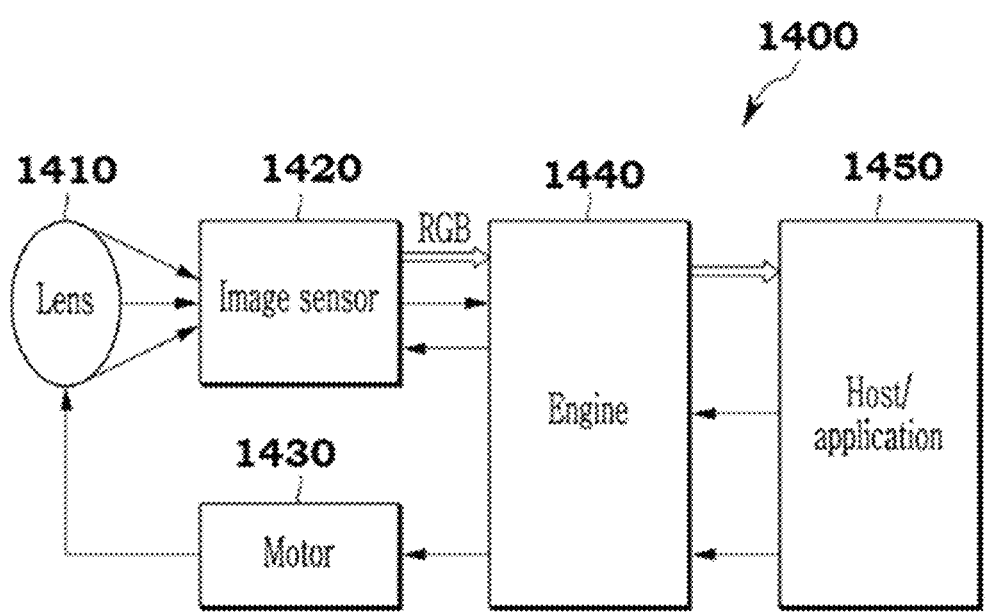
FIG. 14 is a block diagram of a digital camera including an image sensor according to an embodiment.

FIG. 14 is a block diagram of a digital camera including an image sensor according to an embodiment.

Referring to FIG. 14, a digital camera 1400 includes a lens 1410, an image sensor 1420, a motor 1430, and an engine 1440. The image sensor 1420 may be one according to one of the aforementioned embodiments.

The lens 1410 concentrates incident light on the image sensor 1420. The image sensor 1420 generates RGB data for received light through the lens 1410. In some embodiments, the image sensor 1420 may interface with the engine 1440. The motor 1430 may adjust the focus of the lens 1410 or perform shuttering in response to a control signal received from the engine 1440. The engine 1440 may control the image sensor 1420 and the motor 1430. The engine 1440 may be connected to a host/application 1050.

In example embodiments, the motor 1430, engine 1440, and host/application 1050 may include processing circuitry such as hardware including logic circuits; a hardware/software combination such as a processor executing software; or a combination thereof. For example, the processing circuitry more specifically may include, but is not limited to, a central processing unit (CPU), an arithmetic logic unit (ALU), a digital signal processor, a microcomputer, a field programmable gate array (FPGA), a System-on-Chip (SoC), a programmable logic unit, a microprocessor, application-specific integrated circuit (ASIC), etc.

Hereinafter, the embodiments are illustrated in more detail with reference to examples. However, these examples are non-limiting, and the present scope is not limited thereto.

SYNTHESIS EXAMPLES

Synthesis Example 1: Synthesis of Compound 1-1

[Compound 1-1]

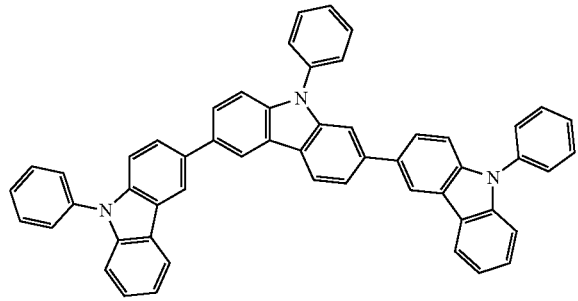

1-1

[Reaction Scheme 1]

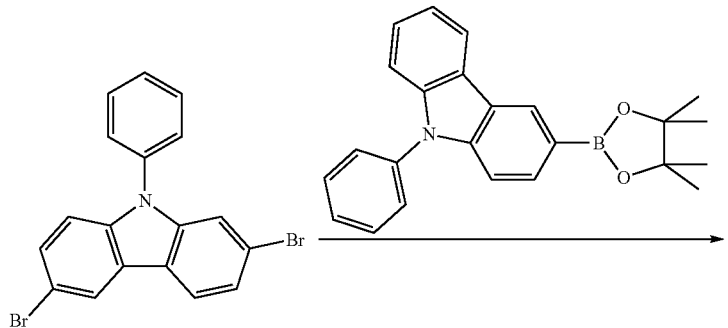

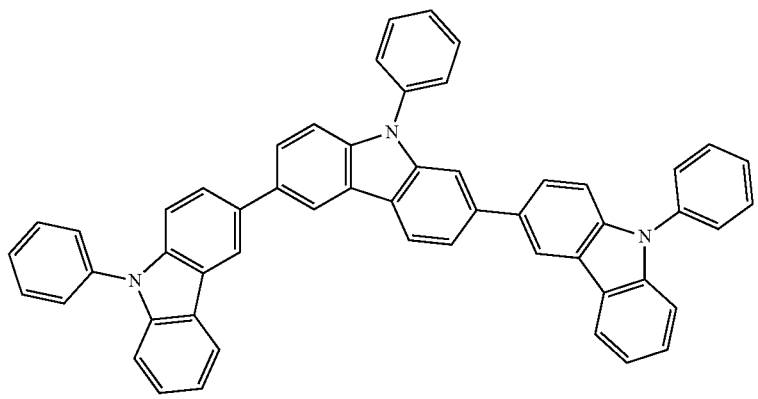

1-1

10.06 g (25.1 mmol) of 2,6-dibromo-9-phenyl-9H-carbazole, 18.52 g (50.1 mmol) of 9-phenyl-3-(4,4,5,5-tetramethyl-1,3,2-dioxaborolan-2-yl)-9H-carbazole, and 3 mol % of tetrakis(triphenylphosphine)palladium (0) ($Pd(PPh_3)_4$) are dissolved in 50 ml of a toluene solvent, and a solution prepared by dissolving 13.86 g (100.3 mmol) of $K_2CO_3$ in 25 ml of water is added thereto and then, heated and refluxed at 100° C. for 12 hours. After removing a solvent from an organic layer, a product therefrom is separated and purified through silica gel column chromatography to obtain 13.5 g (a yield of 74%) of 9,9',9"-triphenyl-9H,9'H,9"H-3,2':6',3"-tercarbazole (Compound 1-1). A molecular weight of Compound 1-1 is 725.90 g/mol.

$^1$H-NMR (300 MHz, Methylene Chloride-d2): δ 8.49 (s. 2H), 8.41 (s, 1H), 8.31 (d, 1H), 8.26 (d, 1H), 8.21 (d, 1H), 7.80 (t, 2H) 7.74-7.57 (m, 15H), 7.54-7.41 (m, 10H), 7.42-7.28 (m, 2H).

Synthesis Example 2: Synthesis of Compound 1-2

[Compound 1-2]

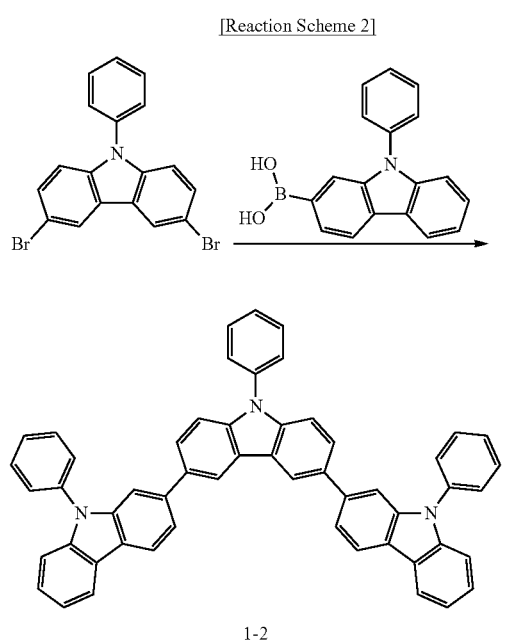

1-2

[Reaction Scheme 2]

10.00 g (24.9 mmol) of 3,6-dibromo-9-phenyl-9H-carbazole, 15.04 g (52.4 mmol) of (9-phenyl-9H-carbazol-2-yl)boronic acid, and 3 mol % of Pd(PPh$_3$)$_4$ are dissolved in 50 ml of a toluene solvent, and a solution prepared by dissolving 13.78 g (99.7 mmol) of K$_2$CO$_3$ in 25 ml of water is added thereto and then, heated and refluxed at 100° C. for 12 hours. After removing a solvent from an organic layer, a product therefrom is separated and purified through silica gel column chromatography to obtain 13.5 g (a yield of 76%) of 9,9',9"-triphenyl-9H,9'H,9"H-3,2':6',3"-tercarbazole (Compound 1-2). A molecular weight of Compound 1-2 is 725.90 g/mol.

$^1$H-NMR (500 MHz, Methylene Chloride-d2): δ 8.55 (s, 2H), 8.48 (s, 2H), 8.24 (d, 2H), 7.80-7.78 (m, 4H), 7.66-7.61 (m, 12H), 7.54-7.41 (m, 11H), 7.30 (t, 2H).

Synthesis Example 3: Synthesis of Compound 80-1

[Compound 80-1]

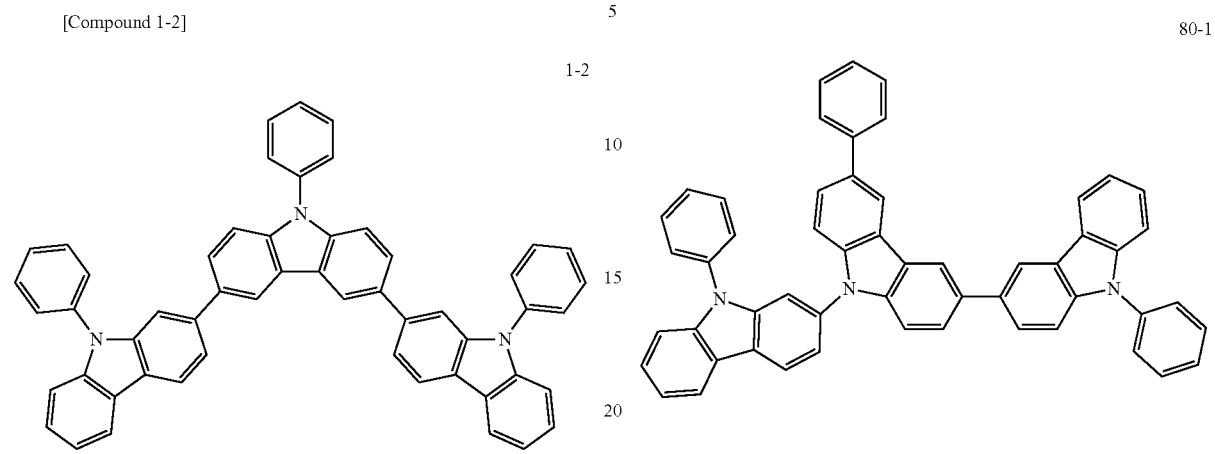

80-1

[Reaction Scheme 3]

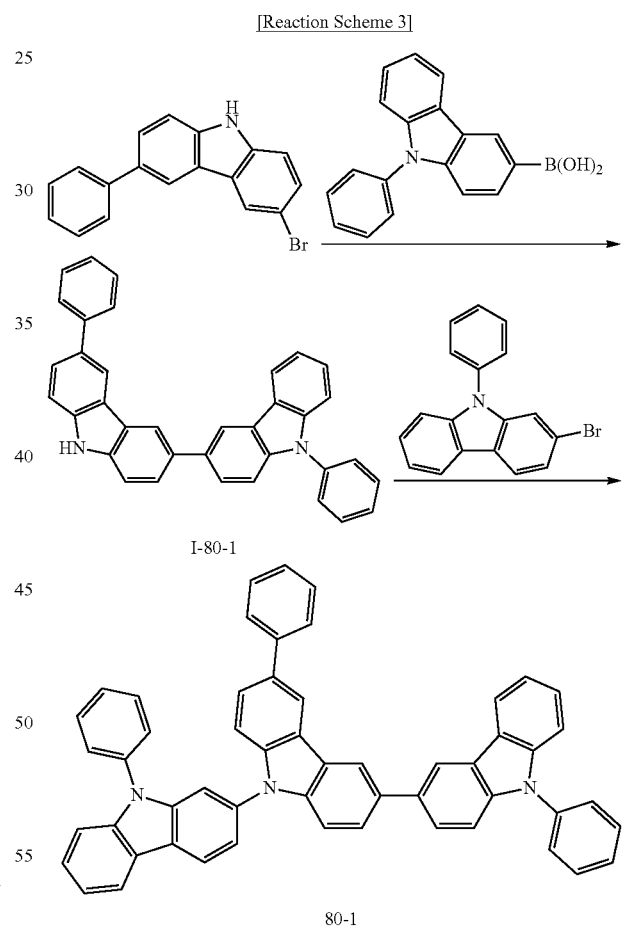

(1) Synthesis of Compound I-80-1

10.04 g (31.2 mmol) of 3-bromo-6-phenyl-9H-carbazole, 9.84 g (34.3 mmol) of (9-phenyl-9H-carbazol-3-yl)boronic acid, and 3 mol % of Pd(PPh$_3$)$_4$ are dissolved in 50 ml of a toluene solvent, and a solution prepared by dissolving 8.61 g (62.3 mmol) of K$_2$CO$_3$ in 25 ml of water is added thereto and then, heated and refluxed at 100° C. for 12 hours. After removing a solvent from an organic layer, a product therefrom is separated and purified through silica gel column chromatography to obtain 11.2 g (a yield of 74%) of 6,9'-diphenyl-9H,9'H-3,3'-bicarbazole (Compound I-80-1).

(2) Synthesis of Compound 80-1

11.20 g (23.1 mmol) of Compound I-80-1 and 8.19 g (25.4 mmol) of 2-bromo-9-phenyl-9H-carbazole are heated and refluxed in 100 ml of anhydrous toluene under the presence of 10 mol % of bis(dibenzylideneacetone)palladium (0) (Pd(dba)$_2$), 20 mol % of tri-t-butylphosphine (P(t-Bu)$_3$), and 6.66 g (69.4 mmol) of sodium t-butoxide (NaOtBu) for 4 hours. A product therefrom is separated and purified through silica gel column chromatography to obtain 13.10 g (a yield of 78%) of 6',9,9''-triphenyl-9H,9''H-2,9': 3',3''-tercarbazole (Compound 80-1). A molecular weight of Compound 80-1 is 725.90 g/mol.

$^1$H-NMR (500 MHz, Methylene Chloride-d2): δ 8.58 (s, 1H), 8.54 (s, 1H), 8.52 (s, 1H), 8.43 (d, 1H), 8.28 (t, 2H), 7.85 (d, 2H), 7.80 (d, 2H), 7.72 (d, 1H), 7.70-7.63 (m, 9H), 7.59-7.48 (m, 12H), 7.37-7.32 (m, 3H).

Synthesis Example 4: Synthesis of Compound 2-1

[Compound 2-1]

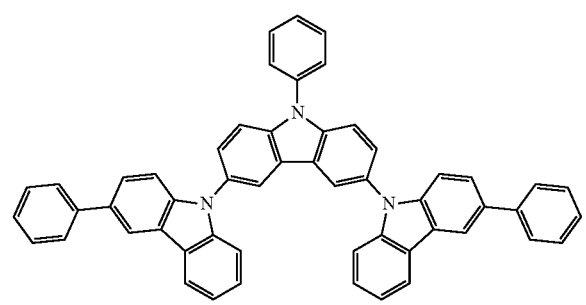

2-1

[Reaction Scheme 4]

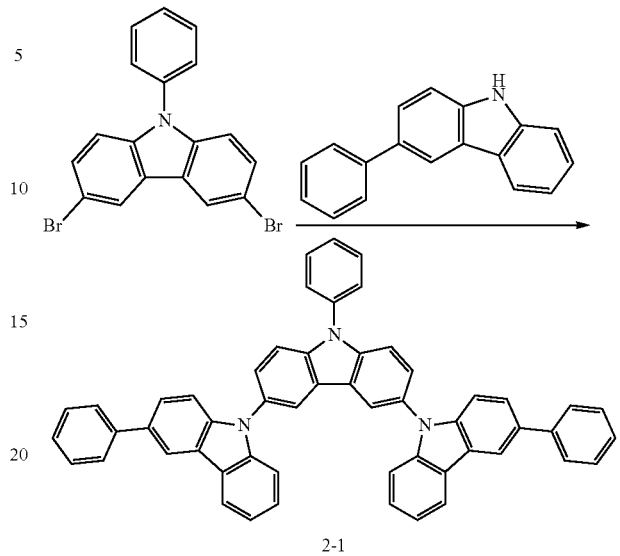

10.00 g (24.9 mmol) of 3,6-dibromo-9-phenyl-9H-carbazole and 12.74 g (52.4 mmol) of 3-phenyl-9H-carbazole are heated and refluxed in 100 ml of anhydrous toluene under the presence of 10 mol % of Pd(dba)$_2$, 20 mol % of P(t-Bu)$_3$, and 14.38 g (149.6 mmol) of NaOtBu for 4 hours. A product therefrom is separated and purified through silica gel column chromatography to obtain 13.9 g (a yield of 77%) of 3,3'',9'-triphenyl-9'H-9,3':6',9''-tercarbazole (Compound 2-1). A molecular weight of Compound 2-1 is 725.90 g/mol.

$^1$H-NMR (500 MHz, Methylene Chloride-d2): δ 8.40 (s, 2H), 8.35 (s, 2H), 8.23 (d, 2H) 7.79-7.60 (m, 15H), 7.50-7.43 (m, 10H), 7.35-7.30 (m, 4H).

Synthesis Example 5: Synthesis of Compound 48-1

[Compound 48-1]

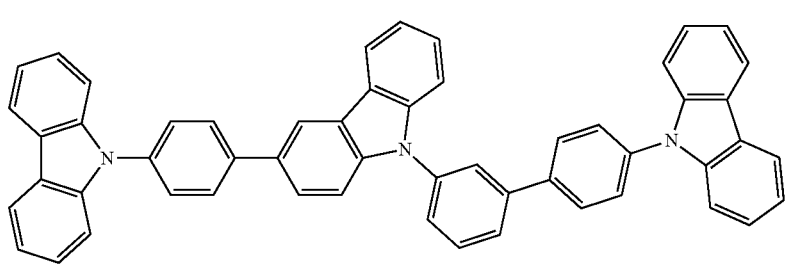

48-1

[Reaction Scheme 5]

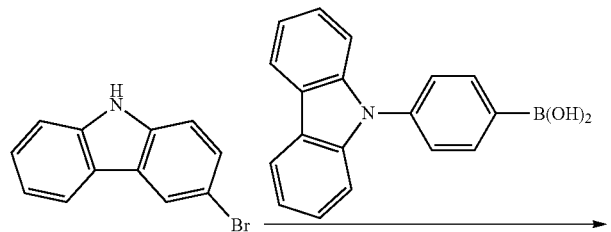

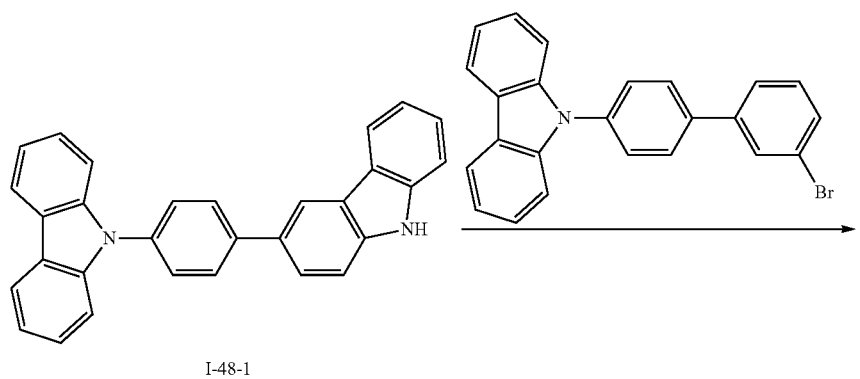

I-48-1

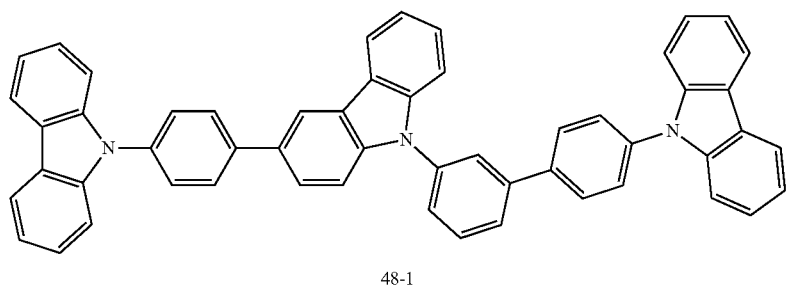

48-1

(1) Synthesis of Compound I-48-1

10.00 g (40.6 mmol) of 3-bromo-9H-carbazole, 12.84 g (44.7 mmol) of (4-(9H-carbazol-9-yl)phenyl)boronic acid, and 3 mol % of Pd(PPh$_3$)$_4$ are dissolved in 50 ml of a toluene solvent, and then, a solution obtained by dissolving 11.23 g (81.3 mmol) of K$_2$CO$_3$ in 25 ml of water is added thereto and then, heated and refluxed at 100° C. for 12 hours. After removing a solvent from an organic layer, a product therefrom is separated and purified through silica gel column chromatography to obtain 9.6 g (a yield of 58%) of 3-(4-(9H-carbazol-9-yl)phenyl)-9H-carbazole (Compound I-48-1).

(2) Synthesis of Compound 48-1

9.61 g (23.5 mmol) of Compound I-48-1 and 10.30 g (25.9 mmol) of 9-(3'-bromo-[1,1'-biphenyl]-4-yl)-9H-carbazole are dissolved in 100 ml of anhydrous toluene and then, heated and refluxed under the presence of 10 mol % of Pd(dba)$_2$, 20 mol % of P(t-Bu)$_3$, and 6.78 g (70.6 mmol) of NaOtBu for 4 hours. A product therefrom is separated and purified through silica gel column chromatography to obtain 10.2 g (a yield of 60%) of 9-(4'-(9H-carbazol-9-yl)-[1,1'-biphenyl]-3-yl)-3-(4-(9H-carbazol-9-yl)phenyl)-9H-carbazole (Compound 48-1). A molecular weight of Compound 48-1 is 725.90 g/mol.

$^1$H-NMR (300 MHz, Methylene Chloride-d2): δ 8.53 (s, 1H), 8.29 (d, 1H), 8.18-8.16 (m, 4H), 8.02-7.94 (m, 5H), 7.89-7.79 (m, 3H), 7.73-7.66 (m, 6H), 7.61-7.25 (m, 15H).

Synthesis Example 6: Synthesis of Compound 6-1

[Compound 6-1]

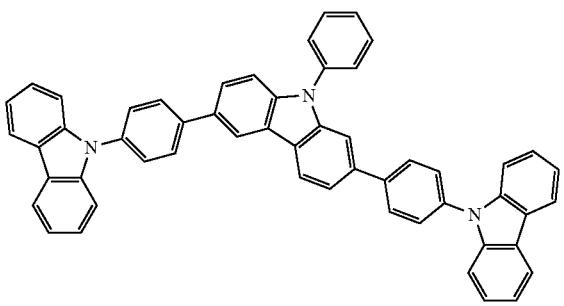

6-1

[Reaction Scheme 6]

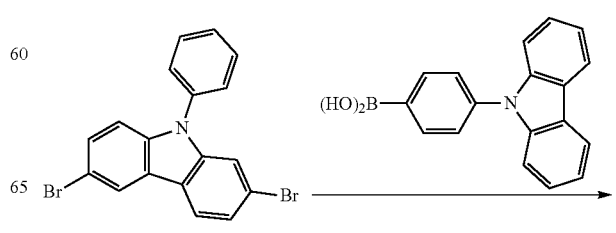

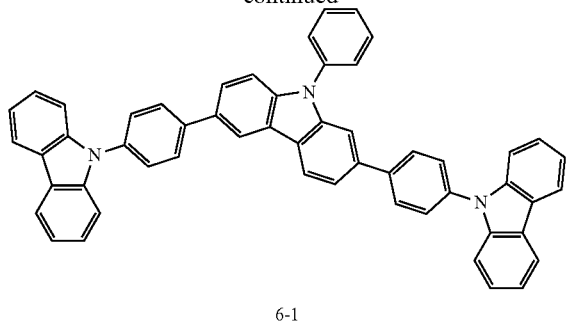

6-1

10.00 g (24.9 mmol) of 2,6-dibromo-9-phenyl-9H-carbazole, 15.04 g (52.4 mmol) of (4-(9H-carbazol-9-yl)phenyl)boronic acid, and 3 mol % of Pd(PPh₃)₄ are dissolved in 50 ml of a toluene solvent, and a solution prepared by dissolving 13.78 g (99.7 mmol) of K₂CO₃ in 25 ml of water is added thereto and then, heated and refluxed at 100° C. for 12 hours.

After removing a solvent from an organic layer, a product therefrom is separated and purified through silica gel column chromatography to obtain 10.3 g (a yield of 57%) of 9,9'-((9-phenyl-9H-carbazole-2,6-diyl)bis(4,1-phenylene))bis(9H-carbazole) (Compound 6-1). A molecular weight of Compound 6-1 is 725.90 g/mol.

¹H-NMR (500 MHz, Methylene Chloride-d2): δ 8.51 (s. 1H), 8.35 (d, 1H), 8.18 (t, 4H) 7.98 (d, 2H), 7.90 (d, 2H), 7.79 (d, 1H), 7.73-7.67 (m, 8H), 7.67-7.63 (d, 2H), 7.58-7.51 (m, 4H), 7.51-7.40 (m, 6H), 7.37-7.27 (m, 4H).

Synthesis Example 7: Synthesis of Compound 3-1

[Compound 3-1]

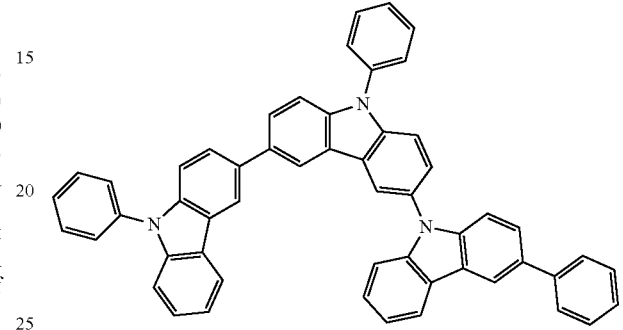

3-1

[Reaction Scheme 7]

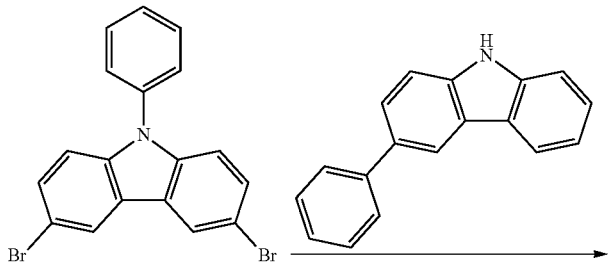

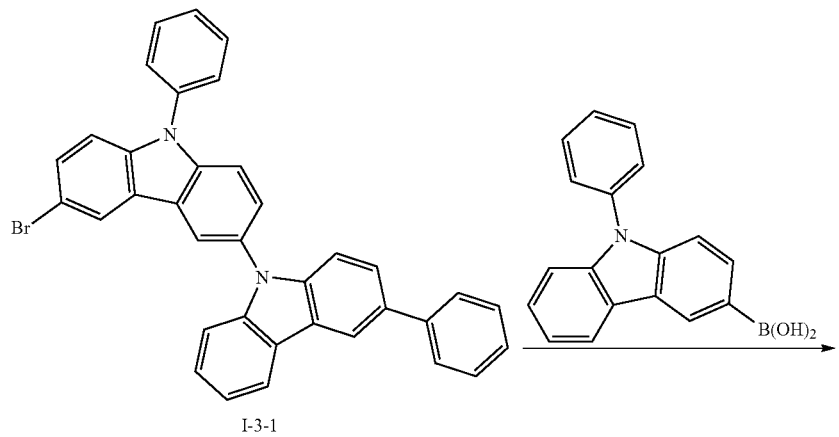

I-3-1

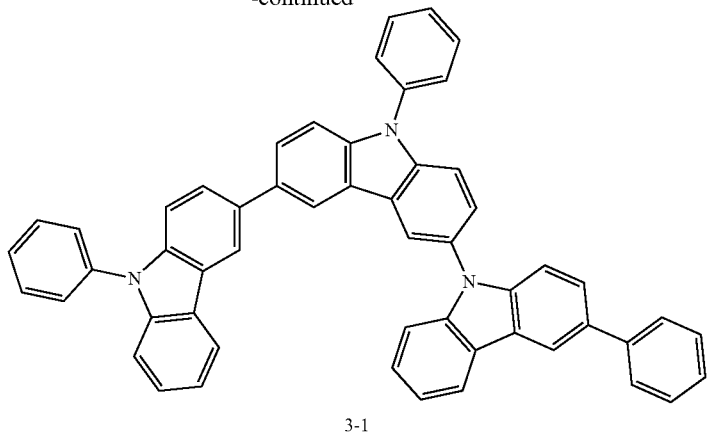

3-1

(1) Synthesis of Compound I-3-1

10.03 g (22.0 mmol) of 3,6-dibromo-9-phenyl-9H-carbazole and 5.35 g (22.0 mmol) of 3-phenyl-9H-carbazole are dissolved in 100 ml of anhydrous toluene and then, heated and refluxed under the presence of 10 mol % of Pd(dba)$_2$, 20 mol % of P(tBu)$_3$, and 6.34 g (66.0 mmol) of NaOtBu for 4 hours. A product therefrom is separated and purified through silica gel column chromatography to obtain 8.9 g (a yield of 72%) of 6-bromo-3',9-diphenyl-9H-3,9'-bicarbazole (Compound I-3-1).

(2) Synthesis of Compound 3-1

8.90 g (15.8 mmol) of Compound I-3-1, 4.54 g (15.8 mmol) of (9-phenyl-9H-carbazol-3-yl)boronic acid, and 3 mol % of Pd(PPh$_3$)$_4$ are dissolved in 50 ml of a toluene solvent, and a solution prepared by dissolving 4.37 g (31.6 mmol) of K$_2$CO$_3$ in 25 ml of water is added thereto and then, heated and refluxed at 100° C. for 12 hours. After removing a solvent from an organic layer, a product therefrom is separated and purified through silica gel column chromatography to obtain 6.8 g (a yield of 59%) of 3'',9,9'-triphenyl-9H,9'H-3,3':6',9''-tercarbazole (Compound 3-1). A molecular weight of Compound 3-1 is 725.90 g/mol.

$^1$H-NMR (300 MHz, Methylene Chloride-d2): δ 8.46 (s, 2H), 8.42 (d, 2H), 8.23 (t, 2H), 7.87 (d, 1H) 7.78-7.67 (m, 8H), 7.64-7.56 (m, 8H), 7.52-7.42 (m, 7H), 7.37-7.30 (m, 5H).

Synthesis Example 8: Synthesis of Compound 86-1

[Compound 86-1]

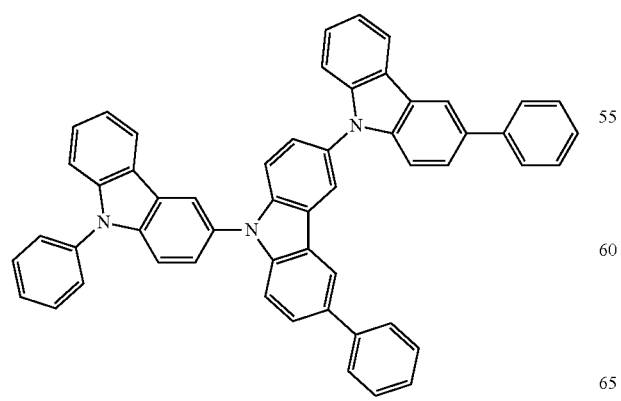

86-1

[Reaction Scheme 8]

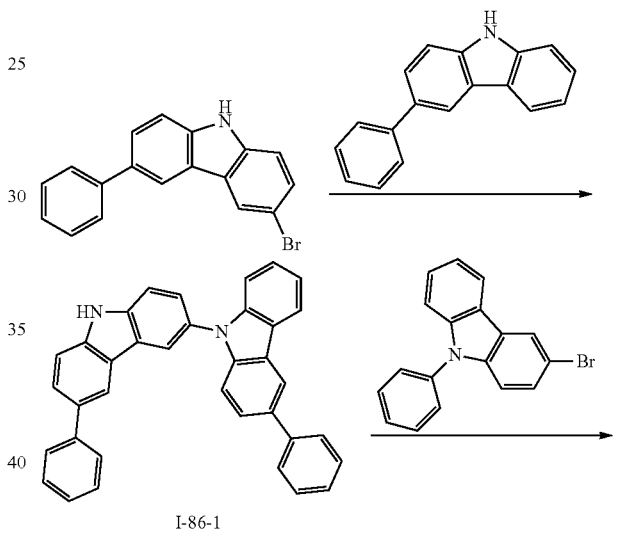

I-86-1

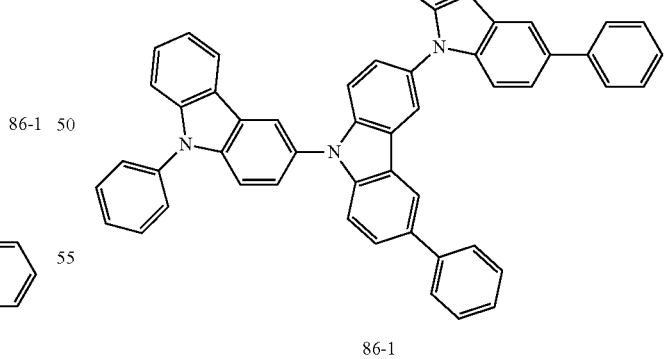

86-1

(1) Synthesis of Compound I-86-1

10.04 g (31.2 mmol) of 3-bromo-6-phenyl-9H-carbazole and 8.34 g (34.3 mmol) of 3-phenyl-9H-carbazole are heated and refluxed in 100 ml of anhydrous toluene under the presence of 10 mol % of Pd(dba)$_2$, 20 mol % of P(tBu)$_3$, and 8.98 g (93.5 mmol) of NaOtBu for 4 hours. A product therefrom is separated and purified through silica gel column chromatography to obtain 8.7 g (a yield of 58%) of 3',6-diphenyl-9H-3,9'-bicarbazole (Compound I-86-1).

(2) Synthesis of Compound 86-1

8.71 g (18.0 mmol) of Compound I-86-1 and 6.37 g (19.8 mmol) of 3-bromo-9-phenyl-9H-carbazole are heated and refluxed in 100 ml of anhydrous toluene under the presence of 10 mol % of Pd(dba)$_2$, 20 mol % of P(t-Bu)$_3$, and 5.18 g (54.0 mmol) of NaOtBu for 4 hours. A product therefrom is separated and purified through silica gel column chromatography to obtain 8.8 g (a yield of 67%) of 3",6',9-triphenyl-9H-3,9':3',9"-tercarbazole (Compound 86-1). A molecular weight of Compound 86-1 is 725.90 g/mol.

$^1$H-NMR (300 MHz, Methylene Chloride-d2): δ 8.55 (d, 2H), 8.30 (d, 1H), 8.13 (d, 1H), 7.99-7.89 (m, 5H) 7.77-7.72 (m, 7H), 7.67-7.58 (m, 5H), 7.50-7.48 (m, 6H), 7.41-7.35 (m, 6H), 7.16-7.15 (m, 2H).

Evaluation I

Energy levels of the compounds obtained by Synthesis Examples are evaluated.

HOMO energy levels are evaluated by irradiating thin films with UV light and then, measuring an amount of photoelectrons emitted therefrom depending on energy with AC-3 (Riken Keiki Co., Ltd.), and LUMO energy levels are evaluated by obtaining an energy bandgap with a UV-Vis spectrometer (Shimadzu Corporation) and then, calculated using the energy bandgap and the measured HOMO energy levels.

The results are shown in Table 1.

TABLE 1

|  | Compound Nos. | HOMO (eV) | LUMO (eV) |
| --- | --- | --- | --- |
| Synthesis Example 1 | 1-1 | 5.60 | 2.37 |
| Synthesis Example 2 | 1-2 | 5.48 | 2.48 |
| Synthesis Example 3 | 80-1 | 5.55 | 2.30 |
| Synthesis Example 4 | 2-1 | 5.73 | 2.16 |
| Synthesis Example 5 | 48-1 | 5.88 | 2.50 |
| Synthesis Example 6 | 6-1 | 5.82 | 2.55 |
| Synthesis Example 7 | 3-1 | 5.63 | 2.06 |
| Synthesis Example 8 | 86-1 | 5.47 | 1.44 |

* HOMO, LUMO: expressed as absolute values

Evaluation II

Heat resistance properties of the compounds obtained by Synthesis Examples are evaluated.

The heat resistance properties are evaluated from a weight loss according to a temperature increase under high vacuum of less than or equal to 10 Pa, and each temperature where 10 wt % and 50 wt % of a weight loss relative to an initial weight occurs is described as Ts$_{10}$, Ts$_{50}$.

The results are shown in Table 2.

TABLE 2

|  | Compound Nos. | Ts$_{10}$ (° C.) | Ts$_{50}$ (° C.) |
| --- | --- | --- | --- |
| Synthesis Example 1 | 1-1 | 340 | 370 |
| Synthesis Example 2 | 1-2 | 222 | 250 |
| Synthesis Example 3 | 80-1 | 331 | 362 |
| Synthesis Example 4 | 2-1 | 330 | 360 |
| Synthesis Example 5 | 48-1 | 342 | 375 |
| Synthesis Example 6 | 6-1 | 342 | 371 |
| Synthesis Example 7 | 3-1 | 335 | 365 |
| Synthesis Example 8 | 86-1 | 331 | 365 |

Referring to Table 2, the compounds obtained by Synthesis Examples have sufficient heat resistance properties.

Manufacture of Photoelectric Conversion Device

Example 1-1

An ITO (WF: 4.9 eV) is sputtered on a glass substrate to form a 150 nm-thick anode. On the anode, Compound 1-1 of Synthesis Example 1 is deposited to form a 5 nm-thick organic buffer layer. On the organic buffer layer, a p-type semiconductor represented by Chemical Formula A-3-1 ($\lambda_{max}$: 545 nm) (HOMO: 5.55 eV, LUMO: 3.54 eV) and fullerene C60 (HOMO: 6.40 eV, LUMO: 4.23 eV) as an n-type semiconductor are co-deposited in a volume ratio (a thickness ratio) of 1:1 to form a 100 nm-thick photoelectric conversion layer. On the photoelectric conversion layer, Yb is thermally deposited to form a 1.5 nm-thick inorganic buffer layer. On the inorganic buffer layer, ITO is sputtered to form a 7 nm-thick cathode (WF: 4.7 eV). On the cathode, aluminum oxide (Al$_2$O$_3$) is deposited to form a 50 nm-thick anti-reflective layer and then, encapsulated with a glass plate to manufacture a photoelectric conversion device.

[Chemical Formula A-3-1]

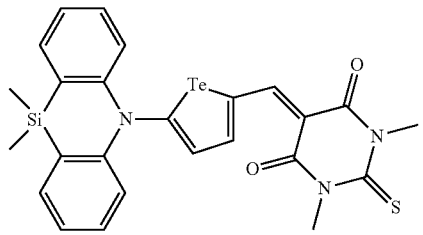

Example 1-2

A photoelectric conversion device is manufactured according to the same method as Example 1-1 except that a 10 nm-thick organic buffer layer is formed.

Example 1-3

A photoelectric conversion device is manufactured according to the same method as Example 1-1 except that a 30 nm-thick organic buffer layer is formed.

Example 2-1

A photoelectric conversion device is manufactured according to the same method as Example 1-1 except that the photoelectric conversion layer is formed by co-depositing a p-type semiconductor and an n-type semiconductor in a volume ratio of 1.25:1, and the organic buffer layer is formed by using Compound 1-2 obtained by Synthesis Example 2 instead of Compound 1-1 obtained by Synthesis Example 1.

Example 2-2

A photoelectric conversion device is manufactured according to the same method as Example 2-1 except that a 10 nm-thick organic buffer layer is formed.

Example 2-3

A photoelectric conversion device is manufactured according to the same method as Example 2-1 except that a 30 nm-thick organic buffer layer is formed.

Example 3-1

A photoelectric conversion device is manufactured according to the same method as Example 1-1 except that the organic buffer layer is formed by using Compound 80-1 obtained by Synthesis Example 3 instead of Compound 1-1 obtained by Synthesis Example 1.

Example 3-2

A photoelectric conversion device is manufactured according to the same method as Example 3-1 except that a 10 nm-thick organic buffer layer is formed.

Example 3-3

A photoelectric conversion device is manufactured according to the same method as Example 3-1 except that a 30 nm-thick organic buffer layer is formed.

Example 4-1

A photoelectric conversion device is manufactured according to the same method as Example 1-1 except that the organic buffer layer is formed by using Compound 2-1 obtained by Synthesis Example 4 instead of Compound 1-1 obtained by Synthesis Example 1.

Example 4-2

A photoelectric conversion device is manufactured according to the same method as Example 4-1 except that a 10 nm-thick organic buffer layer is formed.

Example 4-3

A photoelectric conversion device is manufactured according to the same method as Example 4-1 except that a 30 nm-thick organic buffer layer is formed.

Example 5-1

A photoelectric conversion device is manufactured according to the same method as Example 1-1 except that the organic buffer layer is formed by using Compound 48-1 obtained by Synthesis Example 5 instead of Compound 1-1 obtained by Synthesis Example 1.

Example 5-2

A photoelectric conversion device is manufactured according to the same method as Example 5-1 except that a 10 nm-thick organic buffer layer is formed.

Example 5-3

A photoelectric conversion device is manufactured according to the same method as Example 5-1 except that a 30 nm-thick organic buffer layer is formed.

Example 6-1

A photoelectric conversion device is manufactured according to the same method as Example 1-1 except that the organic buffer layer is formed by using Compound 6-1 obtained by Synthesis Example 6 instead of Compound 1-1 obtained by Synthesis Example 1.

Example 6-2

A photoelectric conversion device is manufactured according to the same method as Example 6-1 except that a 10 nm-thick organic buffer layer is formed.

Example 6-3

A photoelectric conversion device is manufactured according to the same method as Example 6-1 except that a 30 nm-thick organic buffer layer is formed.

Example 7-1

A photoelectric conversion device is manufactured according to the same method as Example 1-1 except that the organic buffer layer is formed by using Compound 3-1 obtained by Synthesis Example 7 instead of Compound 1-1 obtained by Synthesis Example 1.

Example 7-2

A photoelectric conversion device is manufactured according to the same method as Example 7-1 except that a 10 nm-thick organic buffer layer is formed.

Example 7-3

A photoelectric conversion device is manufactured according to the same method as Example 7-1 except that a 30 nm-thick organic buffer layer is formed.

Comparative Example 1

A photoelectric conversion device is manufactured according to the same method as Example 1-1 except that the organic buffer layer is not formed.

Evaluation III

Heat resistance properties of the photoelectric conversion devices according to Examples and Comparative Examples are evaluated.

The heat resistance properties are evaluated by annealing the photoelectric conversions according to Examples and Comparative Examples at 180° C. for 3 hours, and then by confirming changes of each photoelectric conversion efficiency, dark currents, and remaining charge carriers.

The photoelectric conversion efficiency is evaluated by using external quantum efficiency (EQE) at a peak absorption wavelength ($\lambda_{max}$) in a wavelength region of 400 nm to 720 nm using an Incident Photon to Current Efficiency (IPCE) method.

The dark current is evaluated by measuring a current flowing in the devices when −3 V reverse bias is applied thereto.

The remaining charge carrier characteristics indicate an amount of charge carriers photoelectrically converted in one frame but not used in a signal treatment but remaining and read in the next frame and are evaluated by irradiating the devices of Examples and Comparative Examples with photoelectrically convertible light of a green wavelength region and turning it off and then, measuring a current amount measured by a $10^{-6}$ second unit with a Keithley 2400 equipment. The number of remaining electrons are evaluated at 5000 lux by a h+/s/μm² unit.

The results are shown in Tables 3 to 5.

TABLE 3

|  | $EQE_0$ (%) | $EQE_1$ (%) | ΔEQE (%) |
|---|---|---|---|
| Example 1-1 | 70.8 | 68.0 | −4.0 |
| Example 1-2 | 70.2 | 66.7 | −5.0 |
| Example 2-1 | 73.0 | 68.6 | −3.3 |
| Example 2-2 | 72.7 | 67.7 | −3.7 |
| Example 3-1 | 70.5 | 67.2 | −4.7 |
| Example 3-2 | 69.6 | 65.8 | −5.5 |
| Example 4-1 | 69.1 | 67.9 | −1.7 |
| Example 4-2 | 69.1 | 67.5 | −2.3 |
| Example 4-3 | 68.7 | 66.6 | −3.1 |
| Example 5-1 | 69.3 | 66.5 | −4.0 |
| Example 6-1 | 69.5 | 67.6 | −2.7 |
| Example 6-2 | 69.6 | 67.8 | −2.6 |
| Example 6-3 | 69.1 | 66.2 | −4.2 |
| Example 7-1 | 70.4 | 67.2 | −4.5 |
| Example 7-2 | 70.3 | 67.4 | −4.1 |
| Comparative Example 1 | 71.3 | 66.7 | −6.4 |

\* $EQE_0$: EQE before annealing,
\* $EQE_1$: EQE after the annealing at 180° C. for 3 hours
\*ΔEQE: $EQE_1$ - $EQE_0$

TABLE 4

|  | Dark current (−3 V, e⁻/s/μm²) |
|---|---|
| Example 1-1 | 3 |
| Example 1-2 | 2 |
| Example 1-3 | 6 |
| Example 2-1 | 7 |
| Example 2-2 | 4 |
| Example 2-3 | 2 |
| Example 3-1 | 1 |
| Example 3-2 | 1 |
| Example 3-3 | 5 |
| Example 4-1 | 7 |
| Example 4-2 | 2 |
| Example 4-3 | 1 |
| Example 5-1 | 3 |
| Example 5-2 | 2 |
| Example 5-3 | 1 |
| Example 7-1 | 2 |
| Example 7-2 | 1 |
| Example 7-3 | 3 |
| Comparative Example 1 | 84 |

TABLE 5

|  | Remaining electrons (h+/s/μm²) |
|---|---|
| Example 1-1 | 125 |
| Example 1-2 | 146 |
| Example 1-3 | 145 |
| Example 3-1 | 150 |
| Example 6-1 | 106 |
| Example 6-2 | 121 |
| Example 7-1 | 99 |
| Example 7-2 | 95 |
| Example 7-3 | 117 |
| Comparative Example 1 | 181 |

Referring to Tables 3 to 5, the photoelectric conversion devices according to Examples exhibit high heat resistance and thus a small electrical characteristic change at a high temperature after the annealing compared with the photoelectric conversion devices according to Comparative Examples.

While this disclosure has been described in connection with what is presently considered to be practical example embodiments, it is to be understood that inventive concepts are not limited to the disclosed embodiments, but, on the contrary, are intended to cover various modifications and equivalent arrangements included within the spirit and scope of the appended claims.

What is claimed is:

1. A photoelectric conversion device, comprising
a first electrode and a second electrode;
a photoelectric conversion layer between the first electrode and the second electrode, the photoelectric conversion layer comprising a p-type semiconductor and an n-type semiconductor; and
an organic buffer layer between the first electrode and the photoelectric conversion layer, the organic buffer layer comprising an organic buffer material, wherein
the organic buffer material is represented by Chemical Formula 1,

[Chemical Formula 1]

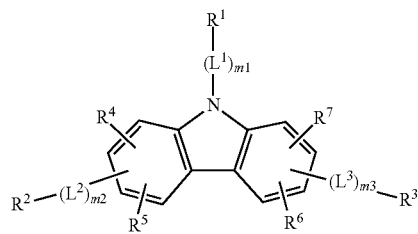

wherein, in Chemical Formula 1,
$L^1$ to $L^3$ are independently a substituted or unsubstituted phenylene group, a substituted or unsubstituted biphenylene group or a substituted or unsubstituted naphthylene group,
$R^1$ to $R^7$ are independently hydrogen, a substituted or unsubstituted C1 to C30 alkyl group, a substituted or unsubstituted C1 to C30 alkoxy group, a substituted or unsubstituted C6 to C20 aryl group, a substituted or unsubstituted C3 to C20 heteroaryl group, a substituted or unsubstituted carbazolyl group, a halogen, a cyano group, or a combination thereof,
$R^1$ is different than $R^2$,
at least two of $R^1$ to $R^3$ are a substituted or unsubstituted carbazolyl group, and
$m^1$ to $m^3$ are independently 0 or 1.

2. The photoelectric conversion device of claim 1, wherein
the LUMO energy level of the organic buffer material is about 1.2 eV to about 3.0 eV, and
the LUMO energy of the n-type semiconductor is about 3.6 eV to about 4.8 eV.

3. The photoelectric conversion device of claim 1, wherein a difference between a HOMO energy level of the organic buffer material and a HOMO energy level of the p-type semiconductor is less than or equal to about 0.5 eV.

4. The photoelectric conversion device of claim 3, wherein the HOMO energy level of the organic buffer material and the HOMO energy level of the p-type semiconductor is within about 5.0 eV to about 6.0 eV.

5. The photoelectric conversion device of claim 3, wherein
a difference between the HOMO energy level of the organic buffer material and the HOMO energy level of the p-type semiconductor is about 0 eV to about 0.5 eV, and
a difference between the LUMO energy level of the organic buffer material and the LUMO energy level of the n-type semiconductor is about 1.2 eV to about 3.6 eV.

6. The photoelectric conversion device of claim 1, wherein a difference between a LUMO energy level of the organic buffer material and a LUMO energy level of the n-type semiconductor being greater than or equal to about 1.2 eV.

7. The photoelectric conversion device of claim 1, wherein the organic buffer material is represented by one of Chemical Formulae 1A to 1C,

[Chemical Formula 1A]

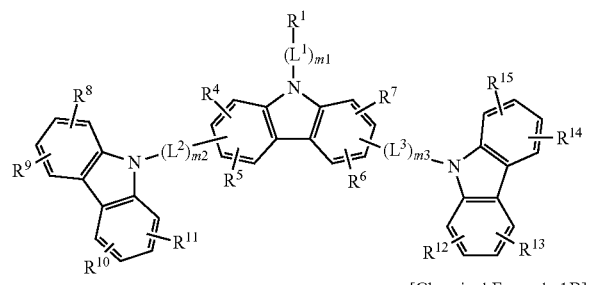

[Chemical Formula 1B]

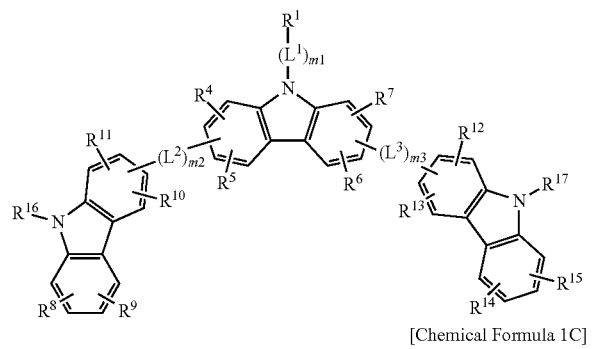

[Chemical Formula 1C]

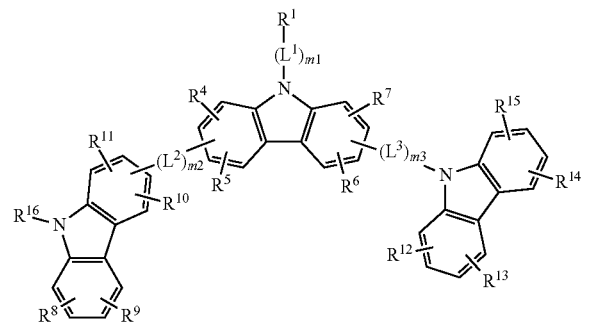

wherein, in Chemical Formulae 1A to 1C,
$L^1$ to $L^3$ are independently a substituted or unsubstituted phenylene group, a substituted or unsubstituted biphenylene group or a substituted or unsubstituted naphthylene group,
$R^1$ is hydrogen, a substituted or unsubstituted C1 to C30 alkyl group, a substituted or unsubstituted C1 to C30 alkoxy group, a substituted or unsubstituted C6 to C20 aryl group, a halogen, a cyano group, or a combination thereof,
$R^4$ to $R^{17}$ are independently hydrogen, a substituted or unsubstituted C1 to C30 alkyl group, a substituted or unsubstituted C1 to C30 alkoxy group, a substituted or unsubstituted C6 to C20 aryl group, a substituted or unsubstituted C3 to C20 heteroaryl group, a substituted or unsubstituted carbazolyl group, a halogen, a cyano group, or a combination thereof, and
$m^1$ to $m^3$ are independently 0 or 1.

8. The photoelectric conversion device of claim 7, wherein $R^1$ and $R^4$ to $R^{17}$ are independently hydrogen, a substituted or unsubstituted phenyl group, a substituted or unsubstituted biphenyl group or a substituted or unsubstituted naphthyl group.

9. The photoelectric conversion device of claim 7, wherein three of $R^1$, $R^4$ to $R^{17}$ and $L^1$ to $L^3$ are a substituted or unsubstituted phenyl group or a substituted or unsubstituted phenylene group.

10. The photoelectric conversion device of claim 1, wherein the organic buffer material is represented by one of Chemical Formulae 1D to 1G,

[Chemical Formula 1D]

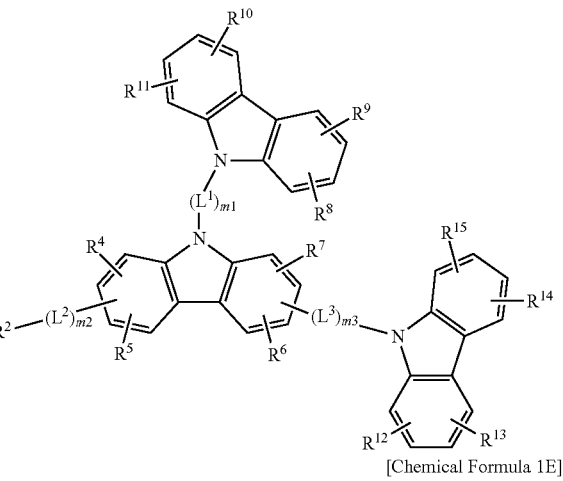

[Chemical Formula 1E]

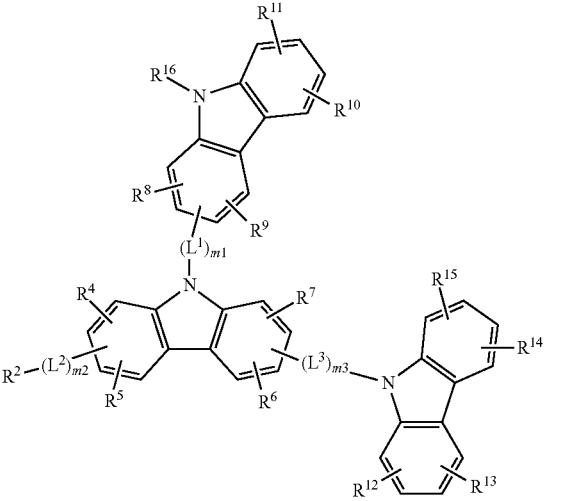

[Chemical Formula 1F]

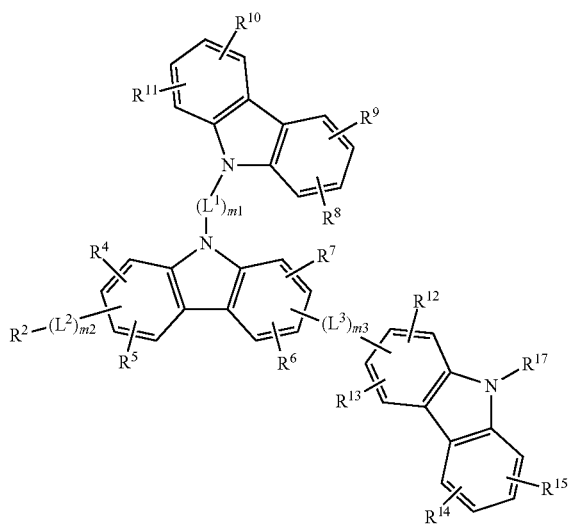

[Chemical Formula 1G]

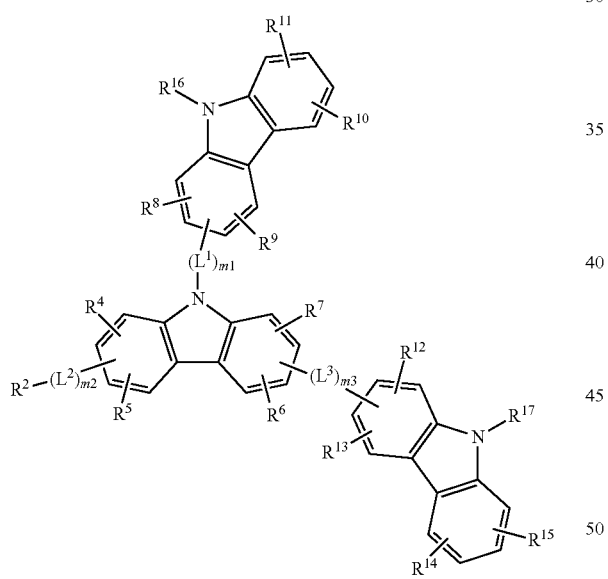

wherein, in Chemical Formulae 1D to 1G,

L$^1$ to L$^3$ are independently a substituted or unsubstituted phenylene group, a substituted or unsubstituted biphenylene group or a substituted or unsubstituted naphthylene group, R$^4$ to R$^{17}$ are independently hydrogen, a substituted or unsubstituted C1 to C30 alkyl group, a substituted or unsubstituted C1 to C30 alkoxy group, a substituted or unsubstituted C6 to C20 aryl group, a substituted or unsubstituted C3 to C20 heteroaryl group, a substituted or unsubstituted carbazolyl group, a halogen, a cyano group, or a combination thereof, R$^2$ is hydrogen, a substituted or unsubstituted C1 to C30 alkyl group, a substituted or unsubstituted C1 to C30 alkoxy group, a substituted or unsubstituted C6 to C20 aryl group, a halogen, a cyano group, or a combination thereof, and m$^1$ to m$^3$ are independently 0 or 1.

11. The photoelectric conversion device of claim 10, wherein R$^2$ and R$^4$ to R$^{17}$ are independently hydrogen, a substituted or unsubstituted phenyl group, a substituted or unsubstituted biphenyl group, or a substituted or unsubstituted naphthyl group.

12. The photoelectric conversion device of claim 10, wherein three of R$^2$, R$^4$ to R$^{17}$ and L$^1$ to L$^3$ are a substituted or unsubstituted phenyl group or a substituted or unsubstituted phenylene group.

13. The photoelectric conversion device of claim 1, wherein i) R$^1$ and R$^3$ are a substituted or unsubstituted carbazolyl group, and R$^2$ is hydrogen, a substituted or unsubstituted phenyl group, a substituted or unsubstituted biphenyl group, or a substituted or unsubstituted naphthyl group, or ii) R$^2$ and R$^3$ are a substituted or unsubstituted carbazolyl group, and R$^1$ is hydrogen, a substituted or unsubstituted phenyl group, a substituted or unsubstituted biphenyl group, or a substituted or unsubstituted naphthyl group.

14. The photoelectric conversion device of claim 1, wherein the organic buffer material comprises three carbazole moieties and three phenyl moieties.

15. The photoelectric conversion device of claim 1, wherein the organic buffer material is represented by one of Chemical Formulae 1-1 to 1-4:

[Chemical Formula 1-1]

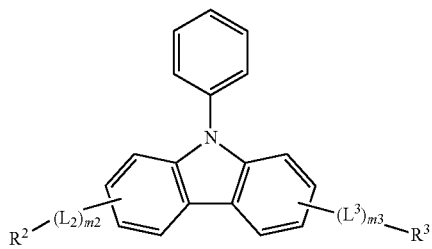

[Chemical Formula 1-2]

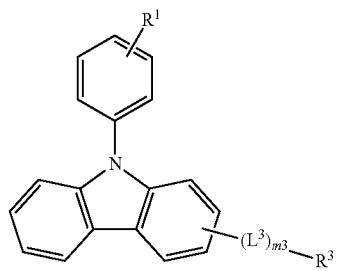

-continued

[Chemical Formula 1-3]

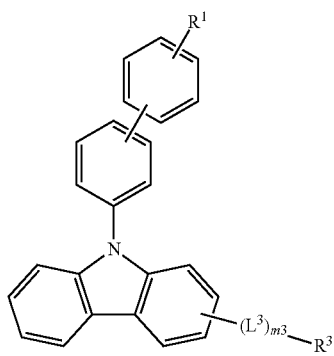

[Chemical Formula 1-4]

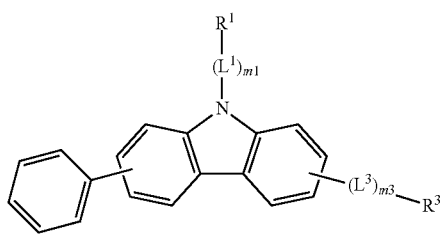

wherein, in Chemical Formulae 1-1 to 1-4, $L^1$ to $L^3$ are independently a phenylene group, $m^1$ to $m^3$ are independently 0 or 1, and $R^1$ to $R^3$ are independently a carbazolyl group or a phenyl-substituted carbazolyl group.

16. The photoelectric conversion device of claim 15, wherein $R^1$ to $R^3$ are independently one of the groups listed in Group 1,

[Group 1]

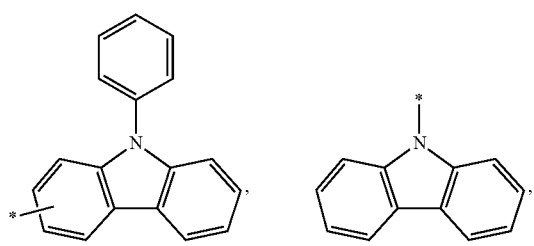

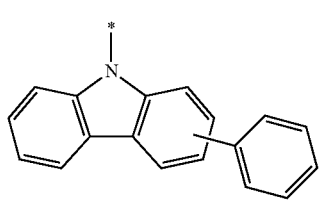

wherein, in Group 1, * is a linking point.

17. The photoelectric conversion device of claim 15, wherein the organic buffer material is represented by Chemical Formula 1-2-1 or 1-3-1:

[Chemical Formula 1-2-1]

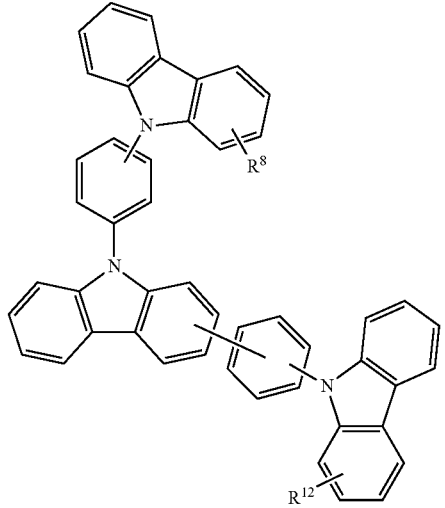

[Chemical Formula 1-3-1]

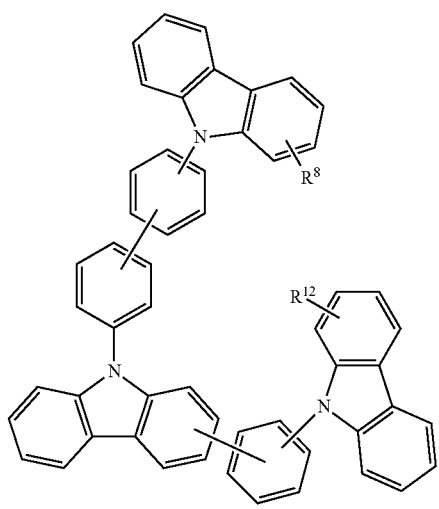

wherein, in Chemical Formulae 1-2-1 or 1-3-1, $R^8$ and $R^{12}$ are independently hydrogen or a phenyl group.

18. The photoelectric conversion device of claim 1, wherein
the p-type semiconductor, the n-type semiconductor, or both the p-type semiconductor and the n-type semiconductor independently is a light-absorbing material having a maximum absorption wavelength in one of a red wavelength region, a green wavelength region, a blue wavelength region, and an infra-red wavelength region.

19. A sensor comprising:
the photoelectric conversion device of claim 1.

20. An electronic device comprising:
the sensor of claim 19.

21. The sensor of claim 19, wherein
the sensor is an organic CMOS image sensor.

22. An electronic device comprising:
the photoelectric conversion device of claim 1.

23. A photoelectric conversion device, comprising
a photoelectric conversion layer comprising a light-absorbing material, the photoelectric conversion layer being configured to convert light absorbed by the light-absorbing material into an electrical signal, and
an organic buffer layer adjacent to the photoelectric conversion layer, the organic buffer layer comprising an organic buffer material,
an absorption spectrum of the photoelectric conversion layer having a maximum absorption wavelength in one of a red wavelength region, a green wavelength region, a blue wavelength region, and an infra-red wavelength region,
the organic buffer material is represented by Chemical Formula 1,

[Chemical Formula 1]

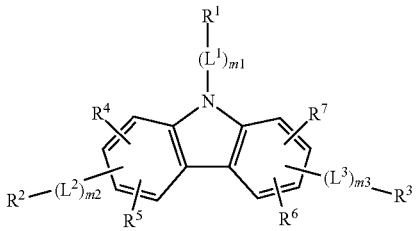

wherein, in Chemical Formula 1,
$L^1$ to $L^3$ are independently a substituted or unsubstituted phenylene group, a substituted or unsubstituted biphenylene group or a substituted or unsubstituted naphthylene group,
$R^1$ to $R^7$ are independently hydrogen, a substituted or unsubstituted C1 to C30 alkyl group, a substituted or unsubstituted C1 to C30 alkoxy group, a substituted or unsubstituted C6 to C20 aryl group, a substituted or unsubstituted C3 to C20 heteroaryl group, a substituted or unsubstituted carbazolyl group, a halogen, a cyano group, or a combination thereof,
$R^1$ is different than $R^2$,
provided that two of $R^1$ to $R^3$ are a substituted or unsubstituted carbazolyl group, and
m1 to m3 are independently 0 or 1.

24. The photoelectric conversion device of claim 23, wherein the organic buffer material comprises three carbazole moieties and three phenyl moieties.

25. A photoelectric conversion device, comprising
a first electrode;
a second electrode on the first electrode;
a photoelectric conversion layer between the first electrode and the second electrode; and
an organic buffer layer between the first electrode and the photoelectric conversion layer, the organic buffer layer including an organic buffer material represented by Chemical Formula 1,

[Chemical Formula 1]

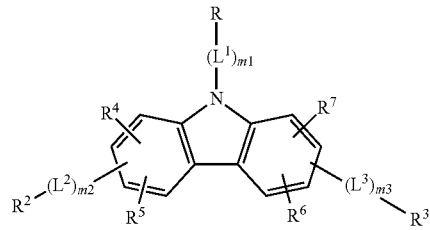

wherein, in Chemical Formula 1,
$L^1$ to $L^3$ are independently a substituted or unsubstituted phenylene group, a substituted or unsubstituted biphenylene group or a substituted or unsubstituted naphthylene group,
$R^1$ to $R^7$ are independently hydrogen, a substituted or unsubstituted C1 to C30 alkyl group, a substituted or unsubstituted C1 to C30 alkoxy group, a substituted or unsubstituted C6 to C20 aryl group, a substituted or unsubstituted C3 to C20 heteroaryl group, a substituted or unsubstituted carbazolyl group, a halogen, a cyano group, or a combination thereof,
$m^1$ to $m^3$ are independently 0 or 1,
provided that two of $R^1$ to $R^3$ are a substituted or unsubstituted carbazolyl group, and a remaining one of $R^1$ to $R^3$ is hydrogen, a substituted or unsubstituted phenyl group, a substituted or unsubstituted biphenyl group, or a substituted or unsubstituted naphthyl group.

26. The photoelectric conversion device of claim 25, wherein
the organic buffer material has a LUMO energy level in a range of about 1.2 eV to about 3.0 eV and a HOMO energy level of about 5.0 eV to about 6.0 eV,
the photoelectric conversion layer includes a p-type semiconductor and an n-type semiconductor,
the LUMO energy of the n-type semiconductor is about 3.6 eV to about 4.8 eV, and
the HOMO energy level of the p-type semiconductor is about 5.0 eV to about 6.0 eV.

27. A sensor comprising:
the photoelectric conversion device of claim 25.

28. An electronic device comprising:
the sensor of claim 27.

29. The photoelectric conversion device of claim 23, wherein $R^1$ and $R^4$ to $R^7$ are independently hydrogen, a substituted or unsubstituted phenyl group, a substituted or unsubstituted biphenyl group or a substituted or unsubstituted naphthyl group.

30. The photoelectric conversion device of claim 23, wherein three of $R^1$, $R^4$ to $R^7$ and $L^1$ to $L^3$ are a substituted or unsubstituted phenyl group-or a substituted or unsubstituted phenylene group.

31. A photoelectric conversion device, comprising
a photoelectric conversion layer comprising a light-absorbing material, the photoelectric conversion layer being configured to convert light absorbed by the light-absorbing material into an electrical signal, and
an organic buffer layer adjacent to the photoelectric conversion layer, the organic buffer layer comprising an organic buffer material,
an absorption spectrum of the photoelectric conversion layer having a maximum absorption wavelength in one of a red wavelength region, a green wavelength region, a blue wavelength region, and an infra-red wavelength region,
the organic buffer material is represented by Chemical Formula 1A,

[Chemical Formula 1A]

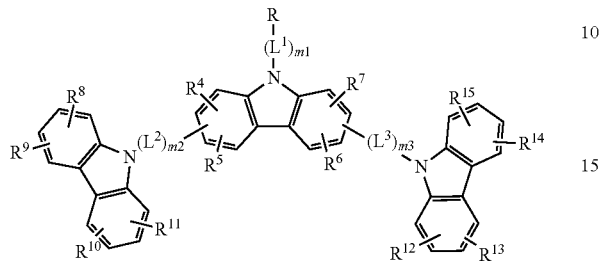

wherein, in Chemical Formula 1A,
$L^1$ to $L^3$ are independently a substituted or unsubstituted C6 to C20 arylene group,
$R^1$ and $R^4$ to $R^{15}$ are independently hydrogen, a substituted or unsubstituted C1 to C30 alkyl group, a substituted or unsubstituted C1 to C30 alkoxy group, a substituted or unsubstituted C6 to C20 aryl group, a substituted or unsubstituted C3 to C20 heteroaryl group, a substituted or unsubstituted carbazolyl group, a halogen, a cyano group, or a combination thereof, and
$m^1$ to $m^3$ are independently 0 or 1.

* * * * *